US012746390B2

(12) United States Patent
Kent et al.

(10) Patent No.: US 12,746,390 B2
(45) Date of Patent: Sep. 29, 2026

(54) PARAMETER VARIATION IN NEURAL STIMULATION

(71) Applicant: Cala Health, Inc., San Mateo, CA (US)

(72) Inventors: Alexander R. Kent, Mountain View, CA (US); Kathryn H. Rosenbluth, San Francisco, CA (US); Gregory T. Schulte, Oakland, CA (US); Jessica M. Liberatore, Burlingame, CA (US); Samuel Richard Hamner, San Francisco, CA (US)

(73) Assignee: Cala Health, Inc., San Mateo, CA (US)

( * ) Notice: Subject to any disclaimer, the term of this patent is extended or adjusted under 35 U.S.C. 154(b) by 86 days.

(21) Appl. No.: 17/926,098

(22) PCT Filed: May 19, 2021

(86) PCT No.: PCT/US2021/033231
§ 371 (c)(1),
(2) Date: Nov. 17, 2022

(87) PCT Pub. No.: WO2021/236815
PCT Pub. Date: Nov. 25, 2021

(65) Prior Publication Data

US 2023/0191126 A1 Jun. 22, 2023

Related U.S. Application Data

(60) Provisional application No. 63/027,806, filed on May 20, 2020.

(51) Int. Cl.
*A61N 1/36* (2006.01)

(52) U.S. Cl.
CPC ..... *A61N 1/36025* (2013.01); *A61N 1/36034* (2017.08)

(58) Field of Classification Search
CPC .. A61N 1/0484; A61N 1/0404; A61N 1/0408; A61N 1/0452; A61N 1/0456;
(Continued)

(56) References Cited

U.S. PATENT DOCUMENTS

| | | |
|---|---|---|
| 3,204,637 A | 9/1965 | Frank et al. |
| 3,870,051 A | 3/1975 | Brindley |

(Continued)

FOREIGN PATENT DOCUMENTS

| | | |
|---|---|---|
| CN | 1135722 | 11/1996 |
| CN | 1547483 | 11/2004 |

(Continued)

OTHER PUBLICATIONS

U.S. Appl. No. 15/277,946, filed Sep. 27, 2016, Rosenbluth et al.

(Continued)

*Primary Examiner* — Joseph D. Boecker
*Assistant Examiner* — Brian T Khong
(74) *Attorney, Agent, or Firm* — Knobbe, Martens, Olson & Bear, LLP

(57) ABSTRACT

Disclosed herein are systems, devices, and methods for stimulating nerves, including electrically stimulating peripheral nerve(s) to treat various diseases and disorders, as well as systems and methods for applying stimulation waveforms for improving the therapeutic benefit, outcomes, and/or experience relating to the same.

21 Claims, 18 Drawing Sheets

(58) Field of Classification Search
CPC .............. A61N 1/0472; A61N 1/36034; A61N 1/36003; A61N 1/36014; A61N 1/3603; A61N 1/36031; A61N 1/36067; A61N 1/36146; A61N 1/3615; A61N 1/36167; A61N 1/36171; A61N 1/36175; A61N 1/36178; A61N 1/36189; A61N 1/36192; A61N 1/36196; A61N 1/0476; A61B 5/1101; A61B 5/6824; A61B 5/6825; A61B 5/681
See application file for complete search history.

(56) References Cited

U.S. PATENT DOCUMENTS 4,103,808 A 8/1978 Hallman et al.
4,233,986 A 11/1980 Tannenbaum
4,300,575 A 11/1981 Wilson
4,313,441 A 2/1982 Buffet
4,458,696 A 7/1984 Larimore
4,461,075 A 7/1984 Bailey
4,539,996 A 9/1985 Engel
4,569,351 A 2/1986 Tang
4,582,049 A 4/1986 Ylvisaker
4,729,377 A 3/1988 Granek et al.
4,739,764 A 4/1988 Lue et al.
4,763,659 A 8/1988 Dunseath, Jr.
4,769,881 A 9/1988 Pedigo et al.
4,771,779 A 9/1988 Tanagho et al.
4,917,092 A 4/1990 Todd et al.
4,981,146 A 1/1991 Bertolucci
4,982,432 A 1/1991 Clark et al.
4,996,987 A 3/1991 Petrofsky
5,003,978 A 4/1991 Dunseath, Jr.
5,052,391 A 10/1991 Silverstone et al.
5,070,862 A 12/1991 Berlant
5,137,507 A 8/1992 Park
5,330,516 A 7/1994 Nathan
5,395,398 A 3/1995 Rogozinski
5,397,338 A 3/1995 Grey et al.
5,433,735 A 7/1995 Zanakis et al.
5,514,175 A 5/1996 Kim et al.
5,540,235 A 7/1996 Wilson
5,562,707 A 10/1996 Prochazka et al.
5,562,717 A 10/1996 Tippey et al.
5,573,011 A 11/1996 Felsing
5,575,294 A 11/1996 Perry et al.
5,606,968 A 3/1997 Mang
5,643,173 A 7/1997 Welles
5,775,331 A 7/1998 Raymond et al.
5,833,709 A 11/1998 Rise et al.
5,833,716 A 11/1998 Bar-Or et al.
5,899,922 A 5/1999 Loos
5,961,542 A 10/1999 Agarwala
6,016,449 A 1/2000 Fischell et al.
6,076,018 A 6/2000 Sturman et al.
6,081,744 A 6/2000 Loos
6,161,044 A 12/2000 Silverstone
6,178,352 B1 1/2001 Gruzdowich et al.
6,351,674 B2 2/2002 Silverstone
6,364,841 B1 4/2002 White et al.
6,366,813 B1 4/2002 DiLorenzo
6,366,814 B1 4/2002 Boveja et al.
6,419,644 B1 7/2002 White et al.
6,445,955 B1 9/2002 Michelson et al.
6,449,512 B1 9/2002 Boveja
6,453,204 B1 9/2002 Rhoads
6,505,074 B2 1/2003 Boveja et al.
6,546,290 B1 4/2003 Shloznikov
6,564,103 B2 5/2003 Fischer et al.
6,572,555 B2 6/2003 White et al.
6,579,270 B2 6/2003 Sussman et al.
6,641,546 B2 11/2003 White et al.
6,652,449 B1 11/2003 Gross et al.
6,662,052 B1 12/2003 Sarwal et al.
6,678,548 B1 1/2004 Echauz et al.
6,701,185 B2 3/2004 Burnett et al.
6,704,603 B1 3/2004 Gesotti
6,731,987 B1 5/2004 McAdams et al.
6,735,474 B1 5/2004 Loeb et al.
6,735,480 B2 5/2004 Giuntoli et al.
6,788,976 B2 9/2004 Gesotti
6,819,956 B2 11/2004 DiLorenzo
6,827,693 B2 12/2004 White et al.
6,829,510 B2 12/2004 Nathan et al.
6,836,684 B1 12/2004 Rijkhoff et al.
6,862,480 B2 3/2005 Cohen et al.
6,892,098 B2 5/2005 Ayal et al.
6,937,905 B2 8/2005 Carroll et al.
6,959,215 B2 10/2005 Gliner et al.
6,959,216 B2 10/2005 Faghri
6,988,005 B2 1/2006 McGraw et al.
7,010,352 B2 3/2006 Hogan
7,089,061 B2 8/2006 Grey
7,146,220 B2 12/2006 Dar et al.
7,162,305 B2 1/2007 Tong et al.
7,171,266 B2 1/2007 Gruzdowich et al.
7,177,694 B2 2/2007 Elbaum
7,177,703 B2 2/2007 Boveja et al.
7,209,787 B2 4/2007 DiLorenzo
7,228,178 B2 6/2007 Carroll et al.
7,231,254 B2 6/2007 DiLorenzo
7,236,830 B2 6/2007 Gliner
7,254,444 B2 8/2007 Moore et al.
7,277,758 B2 10/2007 DiLorenzo
7,283,866 B2 10/2007 Mumford et al.
7,324,851 B1 1/2008 DiLorenzo
7,326,235 B2 2/2008 Edwards
7,328,068 B2 2/2008 Spinelli et al.
7,349,739 B2 3/2008 Harry et al.
7,353,064 B2 4/2008 Gliner et al.
7,369,896 B2 5/2008 Gesotti
7,499,747 B2 3/2009 Kieval et al.
7,529,582 B1 5/2009 DiLorenzo
7,558,610 B1 7/2009 Odderson
7,636,602 B2 12/2009 Baru Fassio et al.
7,640,052 B2 12/2009 Weinstock
7,643,880 B2 1/2010 Tanagho et al.
7,643,882 B2 1/2010 Boston
7,647,112 B2 1/2010 Tracey et al.
7,650,190 B2 1/2010 Zhou et al.
7,657,317 B2 2/2010 Thacker et al.
7,742,820 B2 6/2010 Wyler et al.
7,761,166 B2 7/2010 Giftakis et al.
7,769,464 B2 8/2010 Gerber et al.
7,801,585 B1 9/2010 Weinstock
7,857,771 B2 12/2010 Alwan et al.
7,899,527 B2 3/2011 Yun et al.
7,899,556 B2 3/2011 Nathan et al.
7,917,201 B2 3/2011 Gozani et al.
7,930,034 B2 4/2011 Gerber
7,949,403 B2 5/2011 Palermo et al.
7,957,814 B2 6/2011 Goetz et al.
7,974,696 B1 7/2011 DiLorenzo
7,974,698 B2 7/2011 Tass et al.
7,991,476 B2 8/2011 Nachum
7,996,088 B2 8/2011 Marrosu et al.
7,998,092 B2 8/2011 Avni et al.
8,000,796 B2 8/2011 Tass et al.
8,025,632 B2 9/2011 Einarsson
8,046,083 B2 10/2011 Tegenthoff et al.
8,064,988 B2 11/2011 Weinstock
8,075,499 B2 12/2011 Nathan et al.
8,086,318 B2 12/2011 Strother et al.
8,108,047 B2 1/2012 Schumann
8,121,694 B2 2/2012 Molnar et al.
8,145,316 B2 3/2012 Deem et al.
8,165,668 B2 4/2012 Dacey, Jr. et al.
8,165,685 B1 4/2012 Knutson et al.
8,170,658 B2 5/2012 Dacey, Jr. et al.
8,175,718 B2 5/2012 Wahlgren et al.
8,187,209 B1 5/2012 Guiffrida et al.
8,190,249 B1 5/2012 Gharieb et al.
8,195,287 B2 6/2012 Dacey, Jr. et al.
8,209,036 B2 6/2012 Nathan et al.

(56) References Cited

U.S. PATENT DOCUMENTS

| | | | |
|---|---|---|---|
| 8,219,188 | B2 | 7/2012 | Craig |
| 8,233,988 | B2 | 7/2012 | Errico et al. |
| 8,260,439 | B2 | 9/2012 | Diubaldi et al. |
| 8,265,763 | B2 | 9/2012 | Fahey |
| 8,301,215 | B2 | 10/2012 | Lee |
| 8,306,624 | B2 | 11/2012 | Gerber et al. |
| 8,308,665 | B2 | 11/2012 | Harry et al. |
| 8,313,443 | B2 | 11/2012 | Tom |
| 8,326,398 | B2 | 12/2012 | Weinstock |
| 8,326,432 | B2 | 12/2012 | Kalisek |
| 8,343,026 | B2 | 1/2013 | Gardiner et al. |
| 8,364,257 | B2 | 1/2013 | Van Den Eerenbeemd et al. |
| 8,374,701 | B2 | 2/2013 | Hyde et al. |
| 8,380,314 | B2 | 2/2013 | Pankan et al. |
| 8,382,688 | B2 | 2/2013 | Dar et al. |
| 8,391,970 | B2 | 3/2013 | Tracey et al. |
| 8,396,556 | B2 | 3/2013 | Libbus et al. |
| 8,406,841 | B2 | 3/2013 | Lin et al. |
| 8,409,116 | B2 | 4/2013 | Wang et al. |
| 8,412,338 | B2 | 4/2013 | Faltys |
| 8,414,507 | B2 | 4/2013 | Asada |
| 8,417,351 | B2 | 4/2013 | Kilger |
| 8,428,719 | B2 | 4/2013 | Napadow |
| 8,430,805 | B2 | 4/2013 | Burnett et al. |
| 8,435,166 | B2 | 5/2013 | Burnett et al. |
| 8,447,411 | B2 | 5/2013 | Skelton et al. |
| 8,452,410 | B2 | 5/2013 | Emborg et al. |
| 8,463,374 | B2 | 6/2013 | Hudson et al. |
| 8,473,064 | B2 | 6/2013 | Castel et al. |
| 8,538,512 | B1 | 9/2013 | Bibian et al. |
| 8,548,594 | B2 | 10/2013 | Thimineur et al. |
| 8,571,687 | B2 | 10/2013 | Libbus et al. |
| 8,581,731 | B2 | 11/2013 | Purks et al. |
| 8,583,238 | B1 | 11/2013 | Heldman et al. |
| 8,588,884 | B2 | 11/2013 | Hegde et al. |
| 8,588,917 | B2 | 11/2013 | Whitehurst et al. |
| 8,608,671 | B2 | 12/2013 | Kinoshita et al. |
| 8,626,305 | B2 | 1/2014 | Nielsen et al. |
| 8,639,342 | B2 | 1/2014 | Possover |
| 8,644,904 | B2 | 2/2014 | Chang et al. |
| 8,644,938 | B2 | 2/2014 | Craggs |
| 8,660,644 | B2 | 2/2014 | Jaxx et al. |
| 8,660,653 | B2 | 2/2014 | Kothandaraman et al. |
| 8,660,656 | B2 | 2/2014 | Moser et al. |
| 8,666,496 | B2 | 3/2014 | Simon et al. |
| 8,679,038 | B1 | 3/2014 | Giuffrida |
| 8,682,441 | B2 | 3/2014 | De Ridder |
| 8,688,220 | B2 | 4/2014 | Degiorgio et al. |
| 8,694,104 | B2 | 4/2014 | Libbus et al. |
| 8,694,110 | B2 | 4/2014 | Nathan et al. |
| 8,702,584 | B2 | 4/2014 | Rigaux et al. |
| 8,702,629 | B2 | 4/2014 | Giuffrida et al. |
| 8,706,241 | B2 | 4/2014 | Firlik et al. |
| 8,718,780 | B2 | 5/2014 | Lee |
| 8,738,143 | B2 | 5/2014 | Tucker et al. |
| 8,740,825 | B2 | 6/2014 | Ehrenreich et al. |
| 8,744,587 | B2 | 6/2014 | Miesel et al. |
| 8,755,892 | B2 | 6/2014 | Amurthur et al. |
| D709,874 | S | 7/2014 | Aumiller et al. |
| 8,768,452 | B2 | 7/2014 | Gerber |
| 8,788,045 | B2 | 7/2014 | Gross et al. |
| 8,788,049 | B2 | 7/2014 | Lasko et al. |
| 8,792,977 | B2 | 7/2014 | Kakei et al. |
| 8,798,698 | B2 | 8/2014 | Kim et al. |
| 8,821,416 | B2 | 9/2014 | Johansson et al. |
| 8,825,163 | B2 | 9/2014 | Grill et al. |
| 8,825,165 | B2 | 9/2014 | Possover |
| 8,825,166 | B2 | 9/2014 | John |
| 8,843,201 | B1 | 9/2014 | Heldman et al. |
| 8,845,494 | B2 | 9/2014 | Whitall et al. |
| 8,845,557 | B1 | 9/2014 | Giuffrida et al. |
| 8,849,371 | B2 | 9/2014 | Weinstock |
| 8,855,775 | B2 | 10/2014 | Leyde |
| 8,862,238 | B2 | 10/2014 | Rahimi et al. |
| 8,862,247 | B2 | 10/2014 | Schoendorf et al. |
| 8,868,177 | B2 | 10/2014 | Simon et al. |
| 8,874,227 | B2 | 10/2014 | Simon et al. |
| 8,880,175 | B2 | 11/2014 | Simon |
| 8,886,321 | B2 | 11/2014 | Rohrer et al. |
| 8,892,200 | B2 | 11/2014 | Wagner et al. |
| 8,897,870 | B2 | 11/2014 | De Ridder |
| 8,903,494 | B2 | 12/2014 | Goldwasser et al. |
| 8,920,345 | B2 | 12/2014 | Greenberg et al. |
| 8,923,970 | B2 | 12/2014 | Bar-Yoseph et al. |
| 8,948,876 | B2 | 2/2015 | Gozani et al. |
| 8,958,884 | B2 | 2/2015 | Kothandaraman et al. |
| 8,961,439 | B2 | 2/2015 | Yang et al. |
| 8,972,017 | B2 | 3/2015 | Dar et al. |
| 8,989,861 | B2 | 3/2015 | Su et al. |
| 9,002,477 | B2 | 4/2015 | Burnett |
| 9,005,102 | B2 | 4/2015 | Burnett et al. |
| 9,008,781 | B2 | 4/2015 | Ahmed |
| 9,011,310 | B2 | 4/2015 | Ahmed |
| 9,017,273 | B2 | 4/2015 | Burbank et al. |
| 9,026,216 | B2 | 5/2015 | Rossi et al. |
| 9,042,988 | B2 | 5/2015 | Dilorenzo |
| 9,044,587 | B2 | 6/2015 | Bachinski et al. |
| 9,060,747 | B2 | 6/2015 | Salorio |
| 9,079,029 | B2 | 7/2015 | Weinstock |
| 9,089,691 | B2 | 7/2015 | Libbus et al. |
| 9,095,351 | B2 | 8/2015 | Sachs et al. |
| 9,095,417 | B2 | 8/2015 | Dar et al. |
| 9,107,614 | B2 | 8/2015 | Halkias et al. |
| 9,119,964 | B2 | 9/2015 | Marnfeldt |
| 9,155,885 | B2 | 10/2015 | Wei et al. |
| 9,155,890 | B2 | 10/2015 | Guntinas-Lichius et al. |
| 9,162,059 | B1 | 10/2015 | Lindenthaler |
| 9,168,374 | B2 | 10/2015 | Su |
| 9,174,045 | B2 | 11/2015 | Simon et al. |
| 9,186,095 | B2 | 11/2015 | Machado et al. |
| 9,192,763 | B2 | 11/2015 | Gerber et al. |
| 9,211,417 | B2 | 12/2015 | Giuffrida et al. |
| 9,220,431 | B2 | 12/2015 | Holzhacker |
| 9,220,895 | B2 | 12/2015 | Siff et al. |
| 9,227,056 | B1 | 1/2016 | Heldman et al. |
| 9,238,137 | B2 | 1/2016 | Einav et al. |
| 9,238,142 | B2 | 1/2016 | Heldman et al. |
| 9,242,085 | B2 | 1/2016 | Hershey et al. |
| 9,242,091 | B2 | 1/2016 | Bachinski et al. |
| 9,248,285 | B2 | 2/2016 | Haessler |
| 9,248,286 | B2 | 2/2016 | Simon et al. |
| 9,248,297 | B2 | 2/2016 | Hoyer et al. |
| 9,254,382 | B2 | 2/2016 | Ahmad et al. |
| 9,259,577 | B2 | 2/2016 | Kaula et al. |
| 9,265,927 | B2 | 2/2016 | Yonce et al. |
| 9,282,928 | B1 | 3/2016 | Giffrida |
| 9,289,603 | B1 | 3/2016 | Giuffrida et al. |
| 9,289,607 | B2 | 3/2016 | Su et al. |
| 9,301,712 | B2 | 4/2016 | McNames et al. |
| 9,302,046 | B1 | 4/2016 | Giuffrida et al. |
| 9,302,117 | B2 | 4/2016 | De Vincentiis |
| 9,311,686 | B2 | 4/2016 | Roush et al. |
| 9,314,190 | B1 | 4/2016 | Giuffrida et al. |
| 9,314,622 | B2 | 4/2016 | Embrey et al. |
| 9,332,918 | B1 | 5/2016 | Buckley et al. |
| 9,339,213 | B2 | 5/2016 | Otsamo et al. |
| 9,339,641 | B2 | 5/2016 | Rajguru et al. |
| 9,345,872 | B2 | 5/2016 | Groteke |
| 9,364,657 | B2 | 6/2016 | Kiani et al. |
| 9,364,672 | B2 | 6/2016 | Marnfeldt |
| 9,375,570 | B2 | 6/2016 | Kiani et al. |
| 9,387,338 | B2 | 7/2016 | Burnett |
| 9,393,418 | B2 | 7/2016 | Giuffrida et al. |
| 9,393,430 | B2 | 7/2016 | Demers et al. |
| 9,403,013 | B2 | 8/2016 | Walker et al. |
| 9,408,683 | B2 | 8/2016 | St. Anne et al. |
| 9,414,776 | B2 | 8/2016 | Sillay et al. |
| 9,415,205 | B2 | 8/2016 | Lasko et al. |
| D767,436 | S | 9/2016 | Goodner et al. |
| 9,452,287 | B2 | 9/2016 | Rosenbluth et al. |
| 9,468,753 | B2 | 10/2016 | Fisher et al. |
| 9,474,898 | B2 | 10/2016 | Gozani et al. |
| 9,522,278 | B1 | 12/2016 | Giuffrida et al. |
| 9,533,154 | B2 | 1/2017 | Kothandaraman et al. |

(56) References Cited

U.S. PATENT DOCUMENTS

| | | | |
|---|---|---|---|
| 9,549,872 | B2 | 1/2017 | Chen et al. |
| 9,550,068 | B2 | 1/2017 | Weinstock |
| 9,581,972 | B1 | 2/2017 | Arrow et al. |
| 9,586,038 | B1 | 3/2017 | Kosierkiewicz |
| 9,589,698 | B2 | 3/2017 | Anhalt et al. |
| 9,597,509 | B2 | 3/2017 | Hoffer et al. |
| 9,610,442 | B2 | 4/2017 | Yoo et al. |
| 9,610,459 | B2 | 4/2017 | Burnett et al. |
| 9,615,797 | B2 | 4/2017 | John |
| 9,630,004 | B2 | 4/2017 | Rajguru et al. |
| 9,649,486 | B2 | 5/2017 | Holzhacker |
| 9,656,070 | B2 | 5/2017 | Gozani et al. |
| 9,662,502 | B2 | 5/2017 | Giuffrida et al. |
| 9,669,211 | B2 | 6/2017 | Wijting et al. |
| 9,675,800 | B2 | 6/2017 | Li et al. |
| 9,675,801 | B2 | 6/2017 | Kong et al. |
| 9,707,393 | B2 | 7/2017 | Hsueh et al. |
| 9,717,920 | B1 | 8/2017 | Giuffrida et al. |
| 9,731,126 | B2 | 8/2017 | Ferree et al. |
| 9,757,584 | B2 | 9/2017 | Burnett |
| 9,782,122 | B1 | 10/2017 | Giuffrida et al. |
| 9,782,584 | B2 | 10/2017 | Cartledge et al. |
| 9,802,041 | B2 | 10/2017 | Wong et al. |
| 9,802,046 | B2 | 10/2017 | Grill et al. |
| 9,826,921 | B2 | 11/2017 | Griffiths et al. |
| 9,861,283 | B1 | 1/2018 | Giuffrida |
| 9,877,679 | B1 | 1/2018 | Giuffrida |
| 9,877,680 | B1 | 1/2018 | Giuffrida et al. |
| 9,878,158 | B2 | 1/2018 | Hershey et al. |
| 9,884,179 | B2 | 2/2018 | Bouton et al. |
| 9,924,899 | B2 | 3/2018 | Pracar et al. |
| 9,956,395 | B2 | 5/2018 | Bikson et al. |
| 9,962,549 | B2 | 5/2018 | Kothandaraman et al. |
| 9,974,478 | B1 | 5/2018 | Brokaw et al. |
| 9,980,659 | B2 | 5/2018 | Sadeghian-Motahar et al. |
| 9,992,918 | B2 | 6/2018 | Watanabe et al. |
| 10,004,900 | B2 | 6/2018 | Kent et al. |
| 10,016,600 | B2 | 7/2018 | Creasey et al. |
| 10,022,545 | B1 | 7/2018 | Giuffrida |
| 10,028,695 | B2 | 7/2018 | Machado et al. |
| 10,045,740 | B2 | 8/2018 | John |
| 10,046,161 | B2 | 8/2018 | Biasiucci et al. |
| D828,351 | S | 9/2018 | Xi et al. |
| 10,076,656 | B2 | 9/2018 | Dar et al. |
| 10,080,885 | B2 | 9/2018 | Nathan et al. |
| 10,085,670 | B2 | 10/2018 | Crosson et al. |
| 10,085,689 | B1 | 10/2018 | Giuffrida et al. |
| 10,092,754 | B1 | 10/2018 | Giuffrida et al. |
| 10,099,057 | B2 | 10/2018 | Kent et al. |
| 10,112,040 | B2 | 10/2018 | Herb et al. |
| 10,118,035 | B2 | 11/2018 | Perez et al. |
| 10,118,049 | B2 | 11/2018 | Matthews |
| 10,130,809 | B2 | 11/2018 | Cartledge et al. |
| 10,130,810 | B2 | 11/2018 | Ferree et al. |
| 10,134,378 | B1 | 11/2018 | Cenci et al. |
| 10,137,025 | B2 | 11/2018 | Fior et al. |
| 10,173,060 | B2 | 1/2019 | Wong et al. |
| 10,179,238 | B2 | 1/2019 | Wong et al. |
| 10,188,863 | B2 | 1/2019 | Kaemmerer et al. |
| 10,199,125 | B2 | 2/2019 | Rao et al. |
| 10,213,593 | B2 | 2/2019 | Kaplan et al. |
| 10,213,602 | B2 | 2/2019 | Ironi et al. |
| 10,232,174 | B2 | 3/2019 | Simon et al. |
| 10,232,179 | B2 | 3/2019 | Grill et al. |
| 10,252,053 | B2 | 4/2019 | Page et al. |
| 10,258,798 | B2 | 4/2019 | Panken et al. |
| 10,285,602 | B2 | 5/2019 | Tognetti et al. |
| 10,285,646 | B1 | 5/2019 | Grant et al. |
| 10,286,210 | B2 | 5/2019 | Yoo |
| 10,293,159 | B2 | 5/2019 | Kong et al. |
| 10,335,594 | B2 | 7/2019 | Lin et al. |
| 10,335,595 | B2 | 7/2019 | Ferree et al. |
| 10,342,977 | B2 | 7/2019 | Raghunathan |
| 10,383,571 | B1 | 8/2019 | Giuffrida et al. |
| 10,398,896 | B2 | 9/2019 | Lin et al. |
| 10,456,573 | B1 | 10/2019 | Feinstein et al. |
| 10,463,854 | B2 | 11/2019 | Perez |
| 10,478,626 | B1 | 11/2019 | Giuffrida et al. |
| 10,493,281 | B2 | 12/2019 | Giftakis et al. |
| 10,499,848 | B2 | 12/2019 | Weinstock |
| 10,500,396 | B2 | 12/2019 | Tamaki et al. |
| 10,506,944 | B2 | 12/2019 | Tognetti et al. |
| 10,537,732 | B2 | 1/2020 | Nachum et al. |
| 10,549,093 | B2 | 2/2020 | Wong et al. |
| 10,556,107 | B2 | 2/2020 | Yoo et al. |
| 10,561,839 | B2 | 2/2020 | Wong et al. |
| 10,603,482 | B2 | 3/2020 | Hamner et al. |
| 10,610,114 | B2 | 4/2020 | Buckley et al. |
| 10,625,074 | B2 | 4/2020 | Rosenbluth et al. |
| 10,632,312 | B2 | 4/2020 | Ziv |
| 10,661,082 | B2 | 5/2020 | Kerselaers |
| 10,679,599 | B2 | 6/2020 | Cenci et al. |
| 10,694,992 | B1 | 6/2020 | Giuffrida et al. |
| 10,698,492 | B2 | 6/2020 | Daniels |
| 10,716,941 | B2 | 7/2020 | Yang et al. |
| 10,722,709 | B2 | 7/2020 | Yoo et al. |
| 10,736,577 | B2 | 8/2020 | Horne |
| 10,750,946 | B1 | 8/2020 | Giuffrida |
| 10,758,732 | B1 | 9/2020 | Heldman |
| 10,765,856 | B2 | 9/2020 | Wong et al. |
| 10,773,079 | B2 | 9/2020 | Keller et al. |
| 10,780,269 | B2 | 9/2020 | Gozani et al. |
| 10,786,199 | B1 | 9/2020 | Giuffrida et al. |
| 10,786,200 | B1 | 9/2020 | Giuffrida |
| 10,786,625 | B1 | 9/2020 | Giuffrida et al. |
| 10,786,669 | B2 | 9/2020 | Rajguru et al. |
| 10,814,130 | B2 | 10/2020 | Wong et al. |
| 10,814,131 | B2 | 10/2020 | Goldwasser et al. |
| D902,769 | S | 11/2020 | Riot et al. |
| 10,835,736 | B2 | 11/2020 | Horter et al. |
| 10,850,090 | B2 | 12/2020 | Rosenbluth et al. |
| 10,870,002 | B2 | 12/2020 | Wybo et al. |
| 10,881,856 | B2 | 1/2021 | Giuffrida et al. |
| 10,898,124 | B1 | 1/2021 | Fafiani et al. |
| 10,905,879 | B2 | 2/2021 | Wong et al. |
| 10,918,853 | B2 | 2/2021 | Creasey et al. |
| 10,918,867 | B2 | 2/2021 | Walker |
| 10,940,311 | B2 | 3/2021 | Gozani et al. |
| 10,945,879 | B2 | 3/2021 | Black et al. |
| 10,960,207 | B2 | 3/2021 | Wong et al. |
| D915,399 | S | 4/2021 | Chao et al. |
| 10,966,652 | B1 | 4/2021 | Giuffrida et al. |
| 10,967,177 | B2 | 4/2021 | Lee |
| 10,974,049 | B1 | 4/2021 | Giuffrida et al. |
| 10,994,132 | B1 | 5/2021 | Giuffrida et al. |
| 11,004,563 | B2 | 5/2021 | Lin et al. |
| 11,026,835 | B2 | 6/2021 | Black et al. |
| 11,033,206 | B2 | 6/2021 | Roh |
| 11,033,731 | B2 | 6/2021 | Jeffery et al. |
| 11,033,736 | B2 | 6/2021 | Edgerton et al. |
| 11,040,198 | B1 | 6/2021 | Giuffrida et al. |
| 11,040,203 | B1 | 6/2021 | Giuffrida et al. |
| 11,058,867 | B2 | 7/2021 | Nathan et al. |
| 11,077,300 | B2 | 8/2021 | McBride |
| 11,077,301 | B2 | 8/2021 | Creasey et al. |
| 11,079,225 | B2 | 8/2021 | Ong et al. |
| 11,103,691 | B2 | 8/2021 | Charlesworth et al. |
| 11,103,699 | B1 | 8/2021 | Oppenheim et al. |
| 11,123,562 | B1 | 9/2021 | Giuffrida et al. |
| 11,141,586 | B2 | 10/2021 | Campean et al. |
| 11,141,587 | B2 | 10/2021 | Campean et al. |
| 11,160,971 | B2 | 11/2021 | Sharma et al. |
| 11,160,979 | B1 | 11/2021 | Giuffrida et al. |
| 11,166,632 | B2 | 11/2021 | Grossman et al. |
| 11,191,967 | B1 | 12/2021 | Giuffrida et al. |
| 11,191,968 | B1 | 12/2021 | Giuffrida et al. |
| 11,197,999 | B2 | 12/2021 | Crosson |
| 11,213,681 | B2 | 1/2022 | Raghunathan |
| 11,224,742 | B2 | 1/2022 | Burnett |
| 11,247,040 | B2 | 2/2022 | Ferree et al. |
| 11,247,053 | B2 | 2/2022 | Rajguru et al. |
| 11,247,056 | B2 | 2/2022 | Hareland et al. |
| 11,266,836 | B2 | 3/2022 | Charlesworth et al. |
| 11,278,724 | B2 | 3/2022 | Law et al. |

(56) References Cited

U.S. PATENT DOCUMENTS

| | | | |
|---|---|---|---|
| 11,285,321 | B2 | 3/2022 | Ganguly et al. |
| 11,311,235 | B1 | 4/2022 | Giuffrida et al. |
| 11,318,296 | B2 | 5/2022 | Xiao et al. |
| 11,318,307 | B2 | 5/2022 | Kern et al. |
| 11,331,480 | B2 | 5/2022 | Hamner et al. |
| 11,338,120 | B2 | 5/2022 | Yun et al. |
| 11,338,128 | B2 | 5/2022 | Lawson et al. |
| 11,344,722 | B2 | 5/2022 | Wong et al. |
| 11,344,732 | B2 | 5/2022 | Moffitt et al. |
| 11,357,981 | B2 | 6/2022 | Moaddeb et al. |
| 11,363,982 | B1 | 6/2022 | Giuffrida et al. |
| 11,367,519 | B1 | 6/2022 | Heldman et al. |
| 11,383,087 | B1 | 7/2022 | Heldman et al. |
| 11,389,074 | B2 | 7/2022 | Togenetti et al. |
| 11,389,651 | B2 | 7/2022 | Tamaki et al. |
| 11,419,515 | B2 | 8/2022 | Crosson et al. |
| 11,420,052 | B2 | 8/2022 | Doskocil et al. |
| 11,424,755 | B2 | 8/2022 | Yang et al. |
| D962,929 | S | 9/2022 | He et al. |
| 11,484,710 | B2 | 11/2022 | Mantovani et al. |
| 11,504,530 | B2 | 11/2022 | Herr et al. |
| 11,517,753 | B2 | 12/2022 | Rhodes |
| 11,523,754 | B2 | 12/2022 | Battista |
| 11,534,605 | B2 | 12/2022 | Bouton et al. |
| 11,547,316 | B2 | 1/2023 | Crosson et al. |
| 11,559,250 | B1 | 1/2023 | Giuffrida et al. |
| 11,590,348 | B2 | 2/2023 | Moaddeb et al. |
| 11,596,327 | B2 | 3/2023 | Griffiths et al. |
| 11,596,785 | B2 | 3/2023 | Hamner et al. |
| 11,596,791 | B2 | 3/2023 | Wong et al. |
| 11,596,792 | B2 | 3/2023 | Campean et al. |
| 11,607,167 | B2 | 3/2023 | Han et al. |
| 11,623,078 | B2 | 4/2023 | Simon et al. |
| 11,628,300 | B2 | 4/2023 | Rajguru et al. |
| 11,642,513 | B2 | 5/2023 | Sharma et al. |
| 11,666,758 | B2 | 6/2023 | Crosson |
| 11,672,981 | B2 | 6/2023 | Jaasma et al. |
| 11,701,293 | B2 | 7/2023 | Carballo et al. |
| 11,717,682 | B2 | 8/2023 | Gozani et al. |
| 11,744,482 | B1 | 9/2023 | Giuffrida et al. |
| 11,759,642 | B1 | 9/2023 | Heldman |
| 11,766,187 | B2 | 9/2023 | Togenetti et al. |
| 11,766,191 | B2 | 9/2023 | Sharma et al. |
| 11,779,764 | B2 | 10/2023 | Pepin et al. |
| 11,786,727 | B2 | 10/2023 | Colborn et al. |
| 11,786,730 | B1 | 10/2023 | Giuffrida et al. |
| 11,786,735 | B1 | 10/2023 | Giuffrida et al. |
| 11,809,629 | B1 | 11/2023 | Segil et al. |
| 11,833,352 | B2 | 12/2023 | Law et al. |
| 11,839,583 | B1 | 12/2023 | Carballo et al. |
| 11,839,762 | B2 | 12/2023 | Doskocil et al. |
| 11,844,943 | B2 | 12/2023 | Rajguru et al. |
| 11,844,945 | B1 | 12/2023 | Giuffrida et al. |
| 11,857,778 | B2 | 1/2024 | Hamner et al. |
| 11,872,399 | B2 | 1/2024 | Raghunathan |
| 11,878,166 | B2 | 1/2024 | Colburn et al. |
| 11,890,468 | B1 | 2/2024 | Yu |
| 11,890,469 | B2 | 2/2024 | Moaddeb et al. |
| 11,890,475 | B2 | 2/2024 | Vaidyanathan |
| 11,896,824 | B2 | 2/2024 | Doskocil |
| 11,911,604 | B2 | 2/2024 | Sharma et al. |
| 11,911,605 | B2 | 2/2024 | Crosson et al. |
| 11,911,609 | B1 | 2/2024 | Heldman et al. |
| 11,918,806 | B2 | 3/2024 | Wong et al. |
| 11,918,810 | B1 | 3/2024 | Giuffrida et al. |
| 11,922,915 | B2 | 3/2024 | Cenci et al. |
| 11,975,190 | B2 | 5/2024 | Cho et al. |
| 11,975,195 | B1 | 5/2024 | Giuffrida et al. |
| 11,986,317 | B1 | 5/2024 | Heldman et al. |
| 11,992,682 | B2 | 5/2024 | Crawford |
| 11,992,685 | B2 | 5/2024 | Kassiri Bidhendi et al. |
| 12,029,287 | B2 | 7/2024 | Ye et al. |
| 12,029,899 | B1 | 7/2024 | Kostopoulos |
| 12,053,627 | B2 | 8/2024 | Stanslaski et al. |
| 12,083,334 | B2 | 9/2024 | Burnett |
| 12,109,413 | B2 | 10/2024 | Wong et al. |
| 12,138,007 | B2 | 11/2024 | Sharareh |
| 12,157,001 | B2 | 12/2024 | Wong et al. |
| 12,161,478 | B1 | 12/2024 | Heldman et al. |
| 12,161,858 | B2 | 12/2024 | Rosenbluth et al. |
| 12,161,865 | B2 | 12/2024 | Hamner et al. |
| 12,179,012 | B2 | 12/2024 | Simon et al. |
| 12,182,328 | B2 | 12/2024 | Segil et al. |
| 12,186,085 | B2 | 1/2025 | Buckley et al. |
| 12,186,548 | B2 | 1/2025 | Jackson et al. |
| 12,214,204 | B1 | 2/2025 | Giuffrida et al. |
| 12,226,632 | B2 | 2/2025 | Rajguru et al. |
| 12,237,121 | B2 | 2/2025 | Ye et al. |
| D1,066,701 | S | 3/2025 | Raghunathan et al. |
| D1,066,702 | S | 3/2025 | Raghunathan et al. |
| 12,251,560 | B1 | 3/2025 | Blabaky et al. |
| D1,069,129 | S | 4/2025 | Raghunathan et al. |
| 12,262,979 | B2 | 4/2025 | Togenetti et al. |
| 12,263,009 | B1 | 4/2025 | Giuffrida et al. |
| 12,280,258 | B2 | 4/2025 | Hughes et al. |
| 12,285,610 | B1 | 4/2025 | Giuffrida et al. |
| 12,311,175 | B2 | 5/2025 | Charlesworth et al. |
| 12,318,341 | B2 | 6/2025 | Carballo et al. |
| 12,318,342 | B2 | 6/2025 | Carballo et al. |
| 12,343,532 | B1 | 7/2025 | Chakravarthy |
| 12,357,196 | B2 | 7/2025 | Sharma et al. |
| 12,357,824 | B2 | 7/2025 | Wong et al. |
| 12,380,980 | B1 | 8/2025 | Heldman et al. |
| 12,409,323 | B1 | 9/2025 | Giuffrida et al. |
| 12,420,082 | B2 | 9/2025 | Hamner et al. |
| 12,449,899 | B2 | 10/2025 | VanWyk et al. |
| 12,453,853 | B2 | 10/2025 | Rosenbluth et al. |
| 12,465,215 | B2 | 11/2025 | Fotiadis |
| 12,465,764 | B1 | 11/2025 | Covalin et al. |
| 12,502,121 | B1 | 12/2025 | Giuffrida |
| 12,502,536 | B2 | 12/2025 | Moaddeb et al. |
| 12,575,780 | B2 | 3/2026 | Hamner et al. |
| 2001/0020177 | A1 | 9/2001 | Gruzdowich et al. |
| 2001/0056290 | A1 | 12/2001 | Fischell et al. |
| 2002/0055761 | A1 | 5/2002 | Mann et al. |
| 2002/0070252 | A1 | 6/2002 | Bauer |
| 2002/0120183 | A1 | 8/2002 | Abraham-Fuchs et al. |
| 2002/0138116 | A1 | 9/2002 | Bertolucci |
| 2002/0161415 | A1 | 10/2002 | Cohen et al. |
| 2002/0165586 | A1 | 11/2002 | Hill et al. |
| 2002/0177882 | A1 | 11/2002 | DiLorenzo |
| 2003/0032992 | A1 | 2/2003 | Thacker et al. |
| 2003/0045922 | A1 | 3/2003 | Northrop |
| 2003/0088294 | A1 | 5/2003 | Gesotti |
| 2003/0093098 | A1 | 5/2003 | Heitzmann et al. |
| 2003/0100932 | A1 | 5/2003 | Ciaff |
| 2003/0149457 | A1 | 8/2003 | Tcheng et al. |
| 2003/0181959 | A1 | 9/2003 | Dobak, III |
| 2003/0187483 | A1 | 10/2003 | Grey et al. |
| 2003/0195583 | A1 | 10/2003 | Gruzdowich et al. |
| 2004/0015094 | A1 | 1/2004 | Manabe et al. |
| 2004/0088025 | A1 | 5/2004 | Gessotti |
| 2004/0093093 | A1 | 5/2004 | Andrews |
| 2004/0102819 | A1 | 5/2004 | Zou et al. |
| 2004/0111129 | A1 | 6/2004 | Gliner et al. |
| 2004/0127939 | A1 | 7/2004 | Grey et al. |
| 2004/0133249 | A1 | 7/2004 | Gesotti |
| 2004/0167588 | A1 | 8/2004 | Bertolucci |
| 2004/0249416 | A1 | 12/2004 | Yun et al. |
| 2004/0267331 | A1 | 12/2004 | Koeneman et al. |
| 2005/0015042 | A1 | 1/2005 | Sun et al. |
| 2005/0021103 | A1 | 1/2005 | DiLorenzo |
| 2005/0055063 | A1 | 3/2005 | Loeb et al. |
| 2005/0060009 | A1 | 3/2005 | Geotz |
| 2005/0065553 | A1 | 3/2005 | Ben Ezra et al. |
| 2005/0075502 | A1 | 4/2005 | Shafer |
| 2005/0076909 | A1 | 4/2005 | Stahmann et al. |
| 2005/0171576 | A1 | 8/2005 | Williams et al. |
| 2005/0171577 | A1 | 8/2005 | Cohen et al. |
| 2005/0182454 | A1 | 8/2005 | Gharib et al. |
| 2005/0222626 | A1 | 10/2005 | DiLorenzo |
| 2005/0234309 | A1 | 10/2005 | Klapper |
| 2005/0240241 | A1 | 10/2005 | Yun et al. |
| 2005/0257349 | A1 | 11/2005 | Bauer |

(56) References Cited

U.S. PATENT DOCUMENTS

2005/0261559 A1 11/2005 Mumford et al.
2006/0015153 A1 1/2006 Gliner et al.
2006/0047326 A1 3/2006 Wheeler
2006/0052726 A1 3/2006 Weisz et al.
2006/0074450 A1 4/2006 Boveja et al.
2006/0095088 A1 5/2006 De Ridder
2006/0161218 A1 7/2006 Danilov
2006/0173509 A1 8/2006 Lee et al.
2006/0184059 A1 8/2006 Jadidi
2006/0217781 A1 9/2006 John
2006/0224191 A1 10/2006 DiLorenzo
2006/0229678 A1 10/2006 Lee
2006/0253167 A1 11/2006 Kurtz et al.
2006/0276853 A1 12/2006 Tass
2006/0293723 A1 12/2006 Whitehurst et al.
2007/0027486 A1 2/2007 Armstrong
2007/0073361 A1 3/2007 Goren et al.
2007/0123951 A1 5/2007 Boston
2007/0123952 A1 5/2007 Strother et al.
2007/0142862 A1 6/2007 DiLorenzo
2007/0142874 A1 6/2007 John
2007/0156179 A1 7/2007 Karashurov
2007/0156182 A1 7/2007 Castel et al.
2007/0156183 A1 7/2007 Rhodes
2007/0156200 A1 7/2007 Kornet et al.
2007/0173899 A1 7/2007 Levin et al.
2007/0173903 A1 7/2007 Goren et al.
2007/0185409 A1 8/2007 Wu et al.
2007/0203533 A1 8/2007 Goren et al.
2007/0203534 A1 8/2007 Tapper
2007/0207193 A1 9/2007 Zasler et al.
2007/0249952 A1 10/2007 Rubin et al.
2007/0255319 A1 11/2007 Greenberg et al.
2007/0255323 A1 11/2007 Werder et al.
2007/0256284 A1 11/2007 Bauer
2007/0276217 A1 11/2007 Brown et al.
2007/0282228 A1 12/2007 Einav et al.
2007/0293917 A1 12/2007 Thompson et al.
2007/0294746 A1 12/2007 Sasakura et al.
2008/0004672 A1 1/2008 Dalal et al.
2008/0009772 A1 1/2008 Tyler et al.
2008/0021505 A1 1/2008 Hastings et al.
2008/0027507 A1 1/2008 Bijelic et al.
2008/0030170 A1 2/2008 Dacuay et al.
2008/0033259 A1 2/2008 Manto et al.
2008/0033504 A1 2/2008 Bertolucci
2008/0033510 A1 2/2008 Herregraven et al.
2008/0033511 A1* 2/2008 Dobak ................. A61N 1/3605
607/66
2008/0045775 A1 2/2008 Lozano
2008/0051839 A1 2/2008 Libbus et al.
2008/0051845 A1 2/2008 Mentelos
2008/0058773 A1 3/2008 John
2008/0058871 A1 3/2008 Libbus et al.
2008/0058893 A1 3/2008 Noujokat
2008/0061961 A1 3/2008 John
2008/0091256 A1 4/2008 Libbus et al.
2008/0097564 A1 4/2008 Lathrop
2008/0147146 A1 6/2008 Wahlgren et al.
2008/0177398 A1 7/2008 Gross et al.
2008/0195007 A1 8/2008 Podrazhansky et al.
2008/0208282 A1 8/2008 Gelfand et al.
2008/0208288 A1 8/2008 Podrazhansky et al.
2008/0216593 A1 9/2008 Jacobsen et al.
2008/0243204 A1 10/2008 Uthman et al.
2008/0269593 A1 10/2008 Weinstock
2008/0288016 A1 11/2008 Amurthur et al.
2008/0300449 A1 12/2008 Gerber et al.
2008/0306325 A1 12/2008 Burnett et al.
2008/0312520 A1 12/2008 Rowlandson et al.
2009/0005713 A1 1/2009 Podrazhansky et al.
2009/0018609 A1 1/2009 DiLorenzo
2009/0049722 A1 2/2009 Chan
2009/0076565 A1 3/2009 Surwit
2009/0082831 A1 3/2009 Paul et al.
2009/0099623 A1 4/2009 Bentwich
2009/0105785 A1 4/2009 Wei et al.
2009/0112133 A1 4/2009 Deisseroth et al.
2009/0132018 A1 5/2009 DiUbaldi et al.
2009/0157138 A1 6/2009 Errico et al.
2009/0187121 A1 7/2009 Evans
2009/0216294 A1 8/2009 Ewing et al.
2009/0222053 A1 9/2009 Gaunt et al.
2009/0247910 A1 10/2009 Klapper
2009/0249617 A1 10/2009 Karicherla et al.
2009/0270952 A1 10/2009 Weinstock
2009/0299435 A1 12/2009 Gliner et al.
2009/0312690 A1 12/2009 Kim et al.
2009/0318986 A1 12/2009 Alo et al.
2009/0326595 A1 12/2009 Brockway et al.
2009/0326607 A1 12/2009 Castel et al.
2010/0004715 A1 1/2010 Fahey
2010/0010381 A1 1/2010 Skelton et al.
2010/0010383 A1 1/2010 Skelton et al.
2010/0010572 A1 1/2010 Skelton et al.
2010/0016929 A1 1/2010 Prochazka
2010/0036464 A1 2/2010 Picciano
2010/0057154 A1 3/2010 Dietrich et al.
2010/0059722 A1 3/2010 Copp-Howland et al.
2010/0072046 A1 3/2010 Maeda et al.
2010/0076533 A1 3/2010 Dar et al.
2010/0099963 A1 4/2010 Kilger
2010/0107657 A1 5/2010 Vistakula
2010/0125220 A1 5/2010 Seong
2010/0152623 A1 6/2010 Williams
2010/0152817 A1 6/2010 Gillbe
2010/0168501 A1 7/2010 Burnett et al.
2010/0168604 A1 7/2010 Echauz
2010/0174342 A1 7/2010 Boston et al.
2010/0202172 A1 8/2010 Skirda et al.
2010/0222629 A1 9/2010 Burnett et al.
2010/0222630 A1 9/2010 Mangrum et al.
2010/0227330 A1 9/2010 Fink et al.
2010/0228180 A1 9/2010 Jayes et al.
2010/0249637 A1 9/2010 Walter et al.
2010/0292527 A1 11/2010 Schneider et al.
2010/0298655 A1 11/2010 McCombie
2010/0298905 A1 11/2010 Simon
2010/0324611 A1 12/2010 Deming et al.
2011/0004268 A1 1/2011 Tcheng et al.
2011/0009920 A1 1/2011 Whitehurst et al.
2011/0021899 A1 1/2011 Arps et al.
2011/0040204 A1 2/2011 Ivorra et al.
2011/0040288 A1 2/2011 Eckstein et al.
2011/0054358 A1 3/2011 Kim et al.
2011/0071590 A1 3/2011 Mounaim et al.
2011/0082524 A1 4/2011 Thomas et al.
2011/0098780 A1 4/2011 Graupe et al.
2011/0112605 A1 5/2011 Fahey
2011/0118805 A1 5/2011 Wei et al.
2011/0125212 A1 5/2011 Tyler
2011/0137375 A1 6/2011 McBride
2011/0152968 A1 6/2011 Nathan et al.
2011/0184489 A1 7/2011 Nicolelis et al.
2011/0196446 A1 8/2011 Wu
2011/0202107 A1 8/2011 Sunagawa et al.
2011/0208444 A1 8/2011 Solinky
2011/0213278 A1 9/2011 Horak et al.
2011/0224571 A1 9/2011 Pascual-Leone et al.
2011/0230701 A1 9/2011 Simon et al.
2011/0245734 A1 10/2011 Wagner et al.
2011/0250297 A1 10/2011 Oronsky et al.
2011/0282412 A1 11/2011 Glukhovsky et al.
2011/0288615 A1 11/2011 Armstrong et al.
2011/0301663 A1 12/2011 Wang et al.
2011/0313327 A1 12/2011 Van Acht et al.
2012/0010492 A1 1/2012 Thramann et al.
2012/0035674 A1 2/2012 Weinstock
2012/0035680 A1 2/2012 Napadow
2012/0046535 A1 2/2012 Lin et al.
2012/0050298 A1 3/2012 Hoffman
2012/0053491 A1 3/2012 Nathan et al.
2012/0059298 A1 3/2012 Hoffman et al.
2012/0078319 A1 3/2012 De Ridder

(56) References Cited

U.S. PATENT DOCUMENTS

| | | | |
|---|---|---|---|
| 2012/0088986 | A1 | 4/2012 | David et al. |
| 2012/0092178 | A1 | 4/2012 | Callsen et al. |
| 2012/0098493 | A1 | 4/2012 | Budike |
| 2012/0101326 | A1 | 4/2012 | Simon et al. |
| 2012/0109013 | A1 | 5/2012 | Everett et al. |
| 2012/0136410 | A1 | 5/2012 | Rezai et al. |
| 2012/0158094 | A1 | 6/2012 | Kramer et al. |
| 2012/0184801 | A1 | 7/2012 | Simon et al. |
| 2012/0185020 | A1 | 7/2012 | Simon et al. |
| 2012/0186121 | A1 | 7/2012 | Hanssen et al. |
| 2012/0203079 | A1 | 8/2012 | McLaughlin |
| 2012/0203245 | A1 | 8/2012 | Imabayashi et al. |
| 2012/0211013 | A1 | 8/2012 | Otis |
| 2012/0220812 | A1 | 8/2012 | Mishelevich |
| 2012/0239112 | A1 | 9/2012 | Muraoka |
| 2012/0245483 | A1 | 9/2012 | Lundqvist |
| 2012/0259255 | A1 | 10/2012 | Tomlinson et al. |
| 2012/0277621 | A1 | 11/2012 | Gerber et al. |
| 2012/0289869 | A1 | 11/2012 | Tyler |
| 2012/0290036 | A1 | 11/2012 | Karamanoglu et al. |
| 2012/0302821 | A1 | 11/2012 | Burnett |
| 2012/0303080 | A1 | 11/2012 | Ben-David et al. |
| 2012/0310298 | A1 | 12/2012 | Besio et al. |
| 2012/0310299 | A1 | 12/2012 | Norbert et al. |
| 2012/0310303 | A1 | 12/2012 | Popovic et al. |
| 2012/0330182 | A1 | 12/2012 | Alberts et al. |
| 2013/0006322 | A1 | 1/2013 | Tai |
| 2013/0035745 | A1 | 2/2013 | Ahmed et al. |
| 2013/0046276 | A1 | 2/2013 | Mernoe et al. |
| 2013/0053817 | A1 | 2/2013 | Yun et al. |
| 2013/0060124 | A1 | 3/2013 | Zietsma |
| 2013/0066388 | A1 | 3/2013 | Bernhard et al. |
| 2013/0066393 | A1 | 3/2013 | Gross et al. |
| 2013/0066395 | A1 | 3/2013 | Simon et al. |
| 2013/0085317 | A1 | 4/2013 | Feinstein |
| 2013/0090519 | A1 | 4/2013 | Tass |
| 2013/0106684 | A1 | 5/2013 | Weast et al. |
| 2013/0116606 | A1 | 5/2013 | Cordo |
| 2013/0123568 | A1 | 5/2013 | Hamilton et al. |
| 2013/0123666 | A1 | 5/2013 | Giuffrida et al. |
| 2013/0123684 | A1 | 5/2013 | Giuffrida et al. |
| 2013/0131484 | A1 | 5/2013 | Pernu |
| 2013/0131770 | A1 | 5/2013 | Rezai |
| 2013/0150918 | A1 | 6/2013 | Peterson et al. |
| 2013/0158624 | A1 | 6/2013 | Bain et al. |
| 2013/0158627 | A1 | 6/2013 | Gozani et al. |
| 2013/0178765 | A1 | 7/2013 | Mishelevich |
| 2013/0211471 | A1 | 8/2013 | Libbus et al. |
| 2013/0231713 | A1 | 9/2013 | De Ridder et al. |
| 2013/0236867 | A1 | 9/2013 | Avni et al. |
| 2013/0238049 | A1 | 9/2013 | Simon et al. |
| 2013/0245486 | A1 | 9/2013 | Simon et al. |
| 2013/0245713 | A1 | 9/2013 | Tass |
| 2013/0253299 | A1 | 9/2013 | Weber et al. |
| 2013/0262298 | A1 | 10/2013 | Morley |
| 2013/0267759 | A1 | 10/2013 | Jin |
| 2013/0281890 | A1 | 10/2013 | Mishelevich |
| 2013/0289647 | A1 | 10/2013 | Bhadra et al. |
| 2013/0296967 | A1 | 11/2013 | Skaribas et al. |
| 2013/0297022 | A1 | 11/2013 | Pathak |
| 2013/0317565 | A1 | 11/2013 | Weinstock |
| 2013/0331907 | A1 | 12/2013 | Sumners et al. |
| 2013/0333094 | A1 | 12/2013 | Rogers et al. |
| 2013/0338726 | A1 | 12/2013 | Machado |
| 2014/0005743 | A1 | 1/2014 | Giuffrida et al. |
| 2014/0025059 | A1 | 1/2014 | Kerr |
| 2014/0031605 | A1 | 1/2014 | Schneider |
| 2014/0039573 | A1 | 2/2014 | Jindra |
| 2014/0039575 | A1 | 2/2014 | Bradley |
| 2014/0046406 | A1 | 2/2014 | Ellrich et al. |
| 2014/0046407 | A1 | 2/2014 | Ben-Ezra et al. |
| 2014/0046423 | A1 | 2/2014 | Rajguru et al. |
| 2014/0058189 | A1 | 2/2014 | Stubbeman |
| 2014/0067003 | A1 | 3/2014 | Vase et al. |
| 2014/0074179 | A1 | 3/2014 | Heldman et al. |
| 2014/0074180 | A1 | 3/2014 | Giuffrida et al. |
| 2014/0078694 | A1 | 3/2014 | Wissmar |
| 2014/0081345 | A1 | 3/2014 | Hershey |
| 2014/0081353 | A1 | 3/2014 | Cook et al. |
| 2014/0094675 | A1 | 4/2014 | Luna et al. |
| 2014/0094873 | A1 | 4/2014 | Emborg et al. |
| 2014/0107542 | A1 | 4/2014 | Schubert et al. |
| 2014/0114117 | A1 | 4/2014 | Naghavi et al. |
| 2014/0128939 | A1 | 5/2014 | Embrey et al. |
| 2014/0132410 | A1 | 5/2014 | Chang |
| 2014/0142654 | A1 | 5/2014 | Simon et al. |
| 2014/0148872 | A1 | 5/2014 | Goldwasser et al. |
| 2014/0148873 | A1 | 5/2014 | Kirn |
| 2014/0155799 | A1 | 6/2014 | Skahan et al. |
| 2014/0163444 | A1 | 6/2014 | Ingvarsson |
| 2014/0171834 | A1 | 6/2014 | DeGoede et al. |
| 2014/0180361 | A1 | 6/2014 | Burdick et al. |
| 2014/0200573 | A1 | 7/2014 | Deem et al. |
| 2014/0214119 | A1 | 7/2014 | Greiner et al. |
| 2014/0228927 | A1 | 8/2014 | Ahmad et al. |
| 2014/0236258 | A1 | 8/2014 | Carroll et al. |
| 2014/0246628 | A1 | 9/2014 | Anhalt et al. |
| 2014/0249452 | A1 | 9/2014 | Marsh et al. |
| 2014/0257047 | A1 | 9/2014 | Sillay et al. |
| 2014/0257129 | A1 | 9/2014 | Choi et al. |
| 2014/0257141 | A1 | 9/2014 | Giuffrida et al. |
| 2014/0276194 | A1 | 9/2014 | Osorio |
| 2014/0277220 | A1 | 9/2014 | Brennan et al. |
| 2014/0296752 | A1 | 10/2014 | Edgerton et al. |
| 2014/0296934 | A1 | 10/2014 | Gozani et al. |
| 2014/0296935 | A1 | 10/2014 | Ferree et al. |
| 2014/0300490 | A1 | 10/2014 | Kotz et al. |
| 2014/0309709 | A1 | 10/2014 | Gozanl et al. |
| 2014/0316484 | A1 | 10/2014 | Edgerton et al. |
| 2014/0324118 | A1 | 10/2014 | Simon et al. |
| 2014/0330068 | A1 | 11/2014 | Partsch et al. |
| 2014/0330335 | A1 | 11/2014 | Errico et al. |
| 2014/0336003 | A1 | 11/2014 | Franz et al. |
| 2014/0336722 | A1 | 11/2014 | Rocon De Lima et al. |
| 2014/0336731 | A1 | 11/2014 | Weinstock |
| 2014/0343462 | A1 | 11/2014 | Burnet |
| 2014/0350436 | A1 | 11/2014 | Nathan et al. |
| 2014/0358040 | A1 | 12/2014 | Kim et al. |
| 2014/0364678 | A1 | 12/2014 | Harry et al. |
| 2015/0004656 | A1 | 1/2015 | Tang et al. |
| 2015/0005852 | A1 | 1/2015 | Hershey et al. |
| 2015/0012067 | A1 | 1/2015 | Bradley et al. |
| 2015/0018926 | A1 | 1/2015 | Frenkel et al. |
| 2015/0026783 | A1 | 1/2015 | Tseng et al. |
| 2015/0038886 | A1 | 2/2015 | Snow |
| 2015/0042315 | A1 | 2/2015 | Cen et al. |
| 2015/0044656 | A1 | 2/2015 | Eichhorn et al. |
| 2015/0057506 | A1 | 2/2015 | Luna et al. |
| 2015/0073310 | A1 | 3/2015 | Pracar et al. |
| 2015/0080979 | A1 | 3/2015 | Lasko et al. |
| 2015/0097617 | A1 | 4/2015 | Chak |
| 2015/0100004 | A1 | 4/2015 | Goldman et al. |
| 2015/0100104 | A1 | 4/2015 | Kiani et al. |
| 2015/0100105 | A1 | 4/2015 | Kiani et al. |
| 2015/0112404 | A1 | 4/2015 | Holding et al. |
| 2015/0148865 | A1 | 5/2015 | Gozani et al. |
| 2015/0148866 | A1 | 5/2015 | Bulsen et al. |
| 2015/0148878 | A1 | 5/2015 | Yoo et al. |
| 2015/0157274 | A1 | 6/2015 | Ghassemzadeh et al. |
| 2015/0163873 | A1 | 6/2015 | Kawai et al. |
| 2015/0164377 | A1 | 6/2015 | Nathan et al. |
| 2015/0164401 | A1 | 6/2015 | Toth et al. |
| 2015/0190085 | A1 | 7/2015 | Nathan et al. |
| 2015/0190634 | A1 | 7/2015 | Rezai et al. |
| 2015/0196767 | A1 | 7/2015 | Zaghloul |
| 2015/0202444 | A1 | 7/2015 | Franke et al. |
| 2015/0208955 | A1 | 7/2015 | Smith |
| 2015/0216475 | A1 | 8/2015 | Luna et al. |
| 2015/0230733 | A1 | 8/2015 | Heo et al. |
| 2015/0230756 | A1 | 8/2015 | Luna et al. |
| 2015/0273234 | A1 | 10/2015 | Weinstock |
| 2015/0277559 | A1 | 10/2015 | Vescovi et al. |
| 2015/0290463 | A1 | 10/2015 | Yonce |
| 2015/0297901 | A1 | 10/2015 | Kockx |

(56) References Cited

U.S. PATENT DOCUMENTS

2015/0321000 A1 11/2015 Rosenbluth et al.
2015/0335882 A1 11/2015 Gross
2015/0360030 A1 12/2015 Cartledge et al.
2016/0001096 A1 1/2016 Mishelevich
2016/0008620 A1 1/2016 Stubbeman
2016/0016014 A1 1/2016 Wagner et al.
2016/0022987 A1 1/2016 Zschaeck et al.
2016/0022989 A1 1/2016 Pfeifer
2016/0038059 A1 2/2016 Asada et al.
2016/0039239 A1 2/2016 Ward et al.
2016/0045140 A1 2/2016 Kitamura et al.
2016/0089045 A1 3/2016 Sadeghian-Motahar et al.
2016/0106344 A1 4/2016 Nazari
2016/0120432 A1 5/2016 Sridhar et al.
2016/0121110 A1 5/2016 Kent et al.
2016/0128621 A1 5/2016 Machado et al.
2016/0129248 A1 5/2016 Creasey et al.
2016/0144186 A1 5/2016 Kaemmerer et al.
2016/0156261 A1 6/2016 Kaneda
2016/0157735 A1 6/2016 Zhang
2016/0158542 A1 6/2016 Ahmed
2016/0158565 A1 6/2016 Lee
2016/0198998 A1 7/2016 Rahimi et al.
2016/0213924 A1 7/2016 Coleman et al.
2016/0220836 A1 8/2016 Parks
2016/0233034 A1 8/2016 Sheng
2016/0242656 A1 8/2016 Jackson et al.
2016/0262685 A1 9/2016 Wagner et al.
2016/0263376 A1 9/2016 Yoo et al.
2016/0279435 A1 9/2016 Hyde et al.
2016/0287879 A1 10/2016 Denison et al.
2016/0336722 A1 11/2016 Taxter
2016/0339239 A1 11/2016 Yoo et al.
2016/0361540 A9 12/2016 Simon et al.
2016/0375249 A1 12/2016 Bonnet et al.
2017/0014625 A1 1/2017 Rosenbluth et al.
2017/0027812 A1 2/2017 Hyde et al.
2017/0036025 A1 2/2017 Sachs et al.
2017/0042467 A1 2/2017 Herr et al.
2017/0055880 A1 3/2017 Agrawal et al.
2017/0056238 A1 3/2017 Yi et al.
2017/0056643 A1 3/2017 Herb et al.
2017/0079597 A1 3/2017 Horne
2017/0080207 A1 3/2017 Perez et al.
2017/0087364 A1 3/2017 Cartledge et al.
2017/0095667 A1 4/2017 Yakovlev et al.
2017/0113045 A1 4/2017 Baldassano et al.
2017/0132067 A1 5/2017 Singaravelu Vanaja et al.
2017/0157398 A1 6/2017 Wong et al.
2017/0165485 A1 6/2017 Sullivan et al.
2017/0224991 A1 8/2017 Wingeier et al.
2017/0239415 A1 8/2017 Hwang et al.
2017/0246481 A1 8/2017 Mishelevich
2017/0259061 A1 9/2017 Simon et al.
2017/0266443 A1 9/2017 Rajguru et al.
2017/0274208 A1 9/2017 Nagel et al.
2017/0287146 A1 10/2017 Pathak et al.
2017/0312505 A1 11/2017 Ahmed
2017/0312512 A1 11/2017 Creasey et al.
2017/0312513 A1 11/2017 Hershey et al.
2017/0361093 A1 12/2017 Yoo et al.
2017/0368329 A1 12/2017 Tyler et al.
2018/0001086 A1 1/2018 Bartholomew et al.
2018/0001088 A1 1/2018 Tass
2018/0021576 A1 1/2018 Wong et al.
2018/0028809 A1 2/2018 Ziv
2018/0028841 A1 2/2018 Konofagou et al.
2018/0036535 A1 2/2018 Wong et al.
2018/0042654 A1 2/2018 Ingvarsson et al.
2018/0049676 A1 2/2018 Griffiths et al.
2018/0064344 A1 3/2018 Nguyen
2018/0064362 A1 3/2018 Hennings et al.
2018/0064944 A1 3/2018 Grill et al.
2018/0116546 A1 5/2018 Pastoor et al.
2018/0132757 A1 5/2018 Kong et al.
2018/0140842 A1 5/2018 Olaighin et al.
2018/0168905 A1 6/2018 Goodall et al.
2018/0169400 A1 6/2018 Wong et al.
2018/0199841 A1 7/2018 Yang et al.
2018/0214694 A1 8/2018 Parramon
2018/0221620 A1 8/2018 Metzger
2018/0235500 A1 8/2018 Lee et al.
2018/0236217 A1 8/2018 Hamner et al.
2018/0264263 A1 9/2018 Rosenbluth et al.
2018/0289965 A1* 10/2018 Nelson ............... A61N 1/36107
2018/0345020 A1 12/2018 Ironi et al.
2018/0361153 A1 12/2018 Giuffrida et al.
2019/0001117 A1 1/2019 Ben-David et al.
2019/0001129 A1* 1/2019 Rosenbluth .............. A61N 1/08
2019/0001139 A1 1/2019 Mishra et al.
2019/0126047 A1 5/2019 Kassiri Bidhendi et al.
2019/0134393 A1 5/2019 Wong et al.
2019/0143098 A1 5/2019 Kaplan et al.
2019/0143111 A1 5/2019 Hamner et al.
2019/0143113 A1 5/2019 Wong et al.
2019/0167976 A1 6/2019 Byers et al.
2019/0229727 A1 7/2019 Krishna
2019/0269914 A1 9/2019 Moaddeb et al.
2019/0298998 A1 10/2019 Coleman et al.
2019/0299008 A1 10/2019 Rao
2019/0321636 A1 10/2019 Law et al.
2019/0343462 A1 11/2019 Grant et al.
2019/0374771 A1 12/2019 Simon et al.
2020/0023183 A1 1/2020 Ollerenshaw et al.
2020/0038654 A1 2/2020 Doskocil et al.
2020/0046968 A1 2/2020 Herr et al.
2020/0061378 A1 2/2020 Ganguly et al.
2020/0069947 A1 3/2020 Kent
2020/0077943 A1 3/2020 Weinstock
2020/0093400 A1 3/2020 Hamner et al.
2020/0139118 A1 5/2020 John et al.
2020/0147373 A1 5/2020 Tamaki et al.
2020/0155847 A1 5/2020 Perez
2020/0171269 A1 6/2020 Hooper et al.
2020/0171304 A1 6/2020 Simon et al.
2020/0179687 A1 6/2020 Wong et al.
2020/0197707 A1 6/2020 Covalin
2020/0204164 A1 6/2020 Nishiyama
2020/0215324 A1 7/2020 Mantovani et al.
2020/0221975 A1 7/2020 Basta et al.
2020/0254247 A1 8/2020 Brezel et al.
2020/0254251 A1 8/2020 Wong et al.
2020/0269046 A1 8/2020 Page et al.
2020/0276442 A1 9/2020 Owen
2020/0282201 A1 9/2020 Doskocil
2020/0289813 A1 9/2020 Ito et al.
2020/0289814 A1 9/2020 Hamner et al.
2020/0297999 A1 9/2020 Pal
2020/0316379 A1 10/2020 Yoo et al.
2020/0324104 A1 10/2020 Labuschagne et al.
2020/0338348 A1 10/2020 Honeycutt et al.
2020/0346008 A1 11/2020 Song
2020/0367775 A1 11/2020 Buckley et al.
2020/0405188 A1 12/2020 Sharma et al.
2020/0406022 A1 12/2020 Sharma et al.
2021/0008369 A1 1/2021 Crosson
2021/0016079 A1 1/2021 Ekelem et al.
2021/0016089 A1 1/2021 Crosson
2021/0023376 A1 1/2021 Hareland et al.
2021/0031026 A1 2/2021 Simon et al.
2021/0031036 A1 2/2021 Sharma et al.
2021/0052883 A1 2/2021 Wong et al.
2021/0052897 A1 2/2021 Bhadra et al.
2021/0052900 A1 2/2021 Pepin et al.
2021/0060337 A1 3/2021 Wybo et al.
2021/0069507 A1 3/2021 Gozani et al.
2021/0085974 A1 3/2021 Bouton et al.
2021/0085976 A1 3/2021 Heldman et al.
2021/0099867 A1 4/2021 Brown et al.
2021/0100999 A1 4/2021 Rosenbluth et al.
2021/0101007 A1 4/2021 Hamner et al.
2021/0113834 A1 4/2021 Wong et al.
2021/0128906 A1 5/2021 Perez et al.
2021/0162212 A1 6/2021 Kern et al.

(56) References Cited

U.S. PATENT DOCUMENTS

2021/0169684 A1 6/2021 Black et al.
2021/0187279 A1 6/2021 Bouton et al.
2021/0205619 A1 7/2021 Wong et al.
2021/0212230 A1 7/2021 Hsu et al.
2021/0213283 A1 7/2021 Yoo et al.
2021/0220650 A1 7/2021 Kassiri Bidhendi et al.
2021/0244940 A1 8/2021 Liberatore et al.
2021/0244950 A1 8/2021 Ironi et al.
2021/0248893 A1 8/2021 Van Dinther
2021/0252278 A1 8/2021 Hamner et al.
2021/0252279 A1 8/2021 Kong et al.
2021/0260379 A1 8/2021 Charlesworth et al.
2021/0266011 A1 8/2021 Chen et al.
2021/0283400 A1 9/2021 Hamner et al.
2021/0289814 A1 9/2021 Roubos-van den Hil et al.
2021/0299445 A1 9/2021 Rajguru et al.
2021/0308460 A1 10/2021 Wong et al.
2021/0330547 A1 10/2021 Moaddeb et al.
2021/0330974 A1 10/2021 Wong et al.
2021/0353181 A1 11/2021 Roh
2021/0379374 A1 12/2021 Hamner et al.
2021/0379379 A1 12/2021 Campean et al.
2021/0402172 A1 12/2021 Ross et al.
2022/0001164 A1 1/2022 Sharma et al.
2022/0016413 A1 1/2022 John et al.
2022/0031245 A1 2/2022 Bresler
2022/0054820 A1 2/2022 Turner
2022/0054831 A1 2/2022 McBride
2022/0080196 A1 3/2022 Crosson
2022/0088373 A1 3/2022 Burnett
2022/0126095 A1 4/2022 Rajguru et al.
2022/0143391 A1 5/2022 Vaishya et al.
2022/0143392 A1 5/2022 Labuschagne et al.
2022/0143393 A1 5/2022 Charlesworth et al.
2022/0143402 A1 5/2022 Oppenheim et al.
2022/0203091 A1 6/2022 Vysokov
2022/0212007 A1 7/2022 Rajguru et al.
2022/0218991 A1 7/2022 Moaddeb et al.
2022/0220276 A1 7/2022 Ziebell et al.
2022/0233860 A1 7/2022 Hamner et al.
2022/0266011 A1 8/2022 Hamner et al.
2022/0266012 A1 8/2022 Hamner et al.
2022/0273938 A1 9/2022 Chen
2022/0347461 A1 11/2022 Campean et al.
2022/0370786 A1 11/2022 Atkin et al.
2022/0401721 A1 12/2022 Jackson et al.
2022/0409404 A1 12/2022 Yang et al.
2023/0009158 A1 1/2023 Liberatore
2023/0010696 A1 1/2023 Pradeep
2023/0062326 A1 3/2023 Colachis et al.
2023/0074017 A1 3/2023 Pan
2023/0075750 A1 3/2023 Pan
2023/0080790 A1 3/2023 Crosson et al.
2023/0086004 A1 3/2023 Yang et al.
2023/0110185 A1 4/2023 Mantovani et al.
2023/0148956 A1 5/2023 Narayanan et al.
2023/0172542 A1 6/2023 Baker et al.
2023/0191115 A1 6/2023 Blum et al.
2023/0200732 A1 6/2023 Ye et al.
2023/0201584 A1 6/2023 Rajguru et al.
2023/0207232 A1 6/2023 Ye et al.
2023/0218897 A1 7/2023 Wang et al.
2023/0230669 A1 7/2023 Jung
2023/0233855 A1 7/2023 Sunkeri et al.
2023/0248962 A1 8/2023 Zhang et al.
2023/0256245 A1 8/2023 Crosson
2023/0277091 A1 9/2023 Da Costa Blanco
2023/0277109 A1 9/2023 Blum et al.
2023/0277841 A1 9/2023 Wang et al.
2023/0285743 A1 9/2023 Muccio
2023/0293882 A1 9/2023 Howe
2023/0321430 A1 10/2023 Ye et al.
2023/0337944 A1 10/2023 Szmulewicz et al.
2023/0338225 A1 10/2023 Carballo et al.
2023/0363711 A1 11/2023 Theodore et al.
2023/0371846 A1 11/2023 Sharma et al.
2023/0381505 A1 11/2023 Gozani et al.
2023/0381545 A1 11/2023 Carballo et al.
2023/0397833 A1 12/2023 Tognetti et al.
2024/0032819 A1 2/2024 Zhao et al.
2024/0050308 A1 2/2024 Carballo et al.
2024/0058606 A1 2/2024 Law et al.
2024/0062890 A1 2/2024 Shin et al.
2024/0066286 A1 2/2024 Yin et al.
2024/0066287 A1 2/2024 Siff
2024/0090600 A1 3/2024 Colachis et al.
2024/0091533 A1 3/2024 Ziv et al.
2024/0108239 A1 4/2024 Crosson et al.
2024/0122797 A1 4/2024 Moaddeb et al.
2024/0123223 A1 4/2024 Charlesworth et al.
2024/0123227 A1 4/2024 Charlesworth et al.
2024/0123230 A1 4/2024 Raghunathan
2024/0156674 A1 5/2024 Carballo et al.
2024/0156675 A1 5/2024 Carballo et al.
2024/0157142 A1 5/2024 Yeniel et al.
2024/0189594 A1 6/2024 Hamner et al.
2024/0197204 A1 6/2024 Jung et al.
2024/0197237 A1 6/2024 Hamner et al.
2024/0207618 A1 6/2024 Baker et al.
2024/0226550 A1 7/2024 Moaddeb et al.
2024/0245388 A1 7/2024 Plunger
2024/0285951 A1 8/2024 Huynh et al.
2024/0293669 A1 9/2024 Kostopoulos
2024/0293670 A1 9/2024 Kostopoulos
2024/0299734 A1 9/2024 Wang et al.
2024/0299735 A1 9/2024 Wang et al.
2024/0316339 A1 9/2024 Keefer et al.
2024/0325727 A1 10/2024 Hamner et al.
2024/0325728 A1 10/2024 Schulte et al.
2024/0335654 A1 10/2024 Schulte et al.
2024/0374208 A1 11/2024 Zaphrir et al.
2024/0386553 A1 11/2024 Akakin et al.
2024/0406000 A1 12/2024 Nguyen et al.
2024/0408382 A1 12/2024 Shin et al.
2024/0416110 A1 12/2024 Kim
2024/0428429 A1 12/2024 Akakin et al.
2025/0010061 A1 1/2025 John et al.
2025/0010068 A1 1/2025 Carballo et al.
2025/0010078 A1 1/2025 Netoff et al.
2025/0017518 A1 1/2025 Shah et al.
2025/0017815 A1 1/2025 Carballo et al.
2025/0018185 A1 1/2025 Ye et al.
2025/0037595 A1 1/2025 Carballo et al.
2025/0037880 A1 1/2025 Pepin
2025/0065114 A1 2/2025 Crosson et al.
2025/0065117 A1 2/2025 Charlesworth et al.
2025/0068737 A1 2/2025 Keith et al.
2025/0082924 A1 3/2025 Simon et al.
2025/0099019 A1 3/2025 Muhammed et al.
2025/0114608 A1 4/2025 Haddock et al.
2025/0128058 A1 4/2025 Hamner et al.
2025/0128059 A1 4/2025 Rigot et al.
2025/0135189 A1 5/2025 Wong et al.
2025/0135200 A1 5/2025 Wong et al.
2025/0144405 A1 5/2025 Jackson et al.
2025/0144415 A1 5/2025 Vaishya et al.
2025/0161663 A1 5/2025 Rosenbluth et al.
2025/0161664 A1 5/2025 Wong et al.
2025/0161665 A1 5/2025 Liberatore et al.
2025/0161678 A1 5/2025 Rodriguez et al.
2025/0161684 A1 5/2025 Hamner et al.
2025/0161685 A1 5/2025 Hamner et al.
2025/0170399 A1 5/2025 Wong et al.
2025/0195877 A1 6/2025 Schulte et al.
2025/0205464 A1 6/2025 Bradley et al.
2025/0235690 A1 7/2025 Jeffrey et al.
2025/0242150 A1 7/2025 Bouton et al.
2025/0248641 A1 8/2025 Mase
2025/0262430 A1 8/2025 Ross et al.
2025/0268783 A1 8/2025 Carballo et al.
2025/0281309 A1 9/2025 Benigni et al.
2025/0281349 A1 9/2025 Carballo et al.
2025/0281735 A1 9/2025 Yang
2025/0295319 A1 9/2025 Tognetti et al.

(56) References Cited

U.S. PATENT DOCUMENTS

| | | | |
|---|---|---|---|
| 2025/0319311 | A1 | 10/2025 | Sharma et al. |
| 2025/0332415 | A1 | 10/2025 | Kent et al. |
| 2025/0339671 | A1 | 11/2025 | Rosenbluth et al. |
| 2025/0339672 | A1 | 11/2025 | Wong et al. |
| 2025/0339685 | A1 | 11/2025 | Wong et al. |
| 2025/0345593 | A1 | 11/2025 | Rosenbluth et al. |
| 2025/0345594 | A1 | 11/2025 | Rosenbluth et al. |
| 2025/0352855 | A1 | 11/2025 | Dirkes et al. |
| 2025/0367457 | A1 | 12/2025 | Moore et al. |
| 2025/0375134 | A1 | 12/2025 | Chen |
| 2025/0375612 | A1 | 12/2025 | Wong et al. |
| 2025/0380891 | A1 | 12/2025 | Buckley et al. |
| 2025/0381398 | A1 | 12/2025 | McNutt |
| 2026/0000891 | A1 | 1/2026 | Yang |
| 2026/0007354 | A1 | 1/2026 | Yang |
| 2026/0007357 | A1 | 1/2026 | Sobel et al. |
| 2026/0021301 | A1 | 1/2026 | Rosenbluth et al. |

FOREIGN PATENT DOCUMENTS

| | | |
|---|---|---|
| CN | 1826154 | 8/2006 |
| CN | 101022849 | 8/2007 |
| CN | 101115524 | 1/2008 |
| CN | 101365373 | 2/2009 |
| CN | 101612043 | 12/2009 |
| CN | 101687093 | 3/2010 |
| CN | 101801453 | 8/2010 |
| CN | 102089031 | 6/2011 |
| CN | 102481394 | 5/2012 |
| CN | 102905757 | 1/2013 |
| CN | 202724457 | 2/2013 |
| CN | 103517732 | 1/2014 |
| CN | 103608069 | 2/2014 |
| CN | 103889503 | 6/2014 |
| CN | 104144729 | 11/2014 |
| CN | 104168951 | 11/2014 |
| CN | 104436431 | 3/2015 |
| CN | 104519960 | 4/2015 |
| CN | 104939815 | 9/2015 |
| CN | 105457158 | 4/2016 |
| CN | 105848710 | 8/2016 |
| CN | 106413805 | 2/2017 |
| CN | 106687161 | 5/2017 |
| CN | 106794347 | 5/2017 |
| CN | 206434707 U | 8/2017 |
| CN | 107949421 | 4/2018 |
| CN | 108697890 | 10/2018 |
| CN | 111358461 | 7/2020 |
| CN | 118022172 | 2/2024 |
| CN | 117679641 | 3/2024 |
| CN | 118320302 | 7/2024 |
| CN | 222488608 U | 2/2025 |
| CN | 120114759 | 6/2025 |
| DE | 10 2008042373 | 4/2010 |
| DE | 10 2009004011 | 7/2010 |
| EP | 0000759 | 2/1979 |
| EP | 0801957 | 10/1997 |
| EP | 0725665 | 1/1998 |
| EP | 1062988 | 12/2000 |
| EP | 1558333 | 5/2007 |
| EP | 1727591 | 4/2009 |
| EP | 2383014 | 11/2011 |
| EP | 2291115 | 9/2013 |
| EP | 2801389 | 11/2014 |
| EP | 2892418 | 7/2015 |
| EP | 2892419 | 7/2015 |
| EP | 2892613 | 7/2015 |
| EP | 3020448 | 5/2016 |
| EP | 2948043 | 12/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 3349712 | 7/2019 |
| EP | 2790777 | 9/2019 |
| EP | 2734110 | 3/2020 |
| EP | 3503960 | 3/2020 |
| EP | 3650077 | 5/2020 |
| EP | 3113684 | 7/2020 |
| EP | 3352846 | 7/2020 |
| EP | 3337557 | 8/2020 |
| EP | 3493874 | 8/2020 |
| EP | 3409200 | 9/2020 |
| EP | 3701865 | 9/2020 |
| EP | 3427793 | 11/2020 |
| EP | 3758595 | 1/2021 |
| EP | 3261710 | 3/2021 |
| EP | 3641876 | 4/2021 |
| EP | 3679979 | 6/2021 |
| EP | 3841967 | 6/2021 |
| EP | 3402404 | 7/2021 |
| EP | 3562541 | 7/2021 |
| EP | 3675795 | 8/2021 |
| EP | 3648832 | 11/2021 |
| EP | 3100765 | 1/2022 |
| EP | 3399912 | 4/2022 |
| EP | 3558446 | 8/2022 |
| EP | 2714188 | 12/2022 |
| EP | 3487578 | 12/2022 |
| EP | 4108292 | 12/2022 |
| EP | 2967415 | 5/2023 |
| EP | 3326688 | 6/2023 |
| EP | 3784337 | 6/2023 |
| EP | 3870270 | 8/2023 |
| EP | 4233990 | 8/2023 |
| EP | 3541279 | 9/2023 |
| EP | 3989907 | 10/2023 |
| EP | 4171469 | 10/2023 |
| EP | 3600011 | 11/2023 |
| EP | 4010063 | 11/2023 |
| EP | 3463550 | 3/2024 |
| EP | 3565631 | 4/2024 |
| EP | 4356952 | 4/2024 |
| EP | 3842094 | 5/2024 |
| EP | 3990098 | 8/2024 |
| EP | 3784336 | 11/2024 |
| EP | 4556056 | 5/2025 |
| EP | 4433151 | 6/2025 |
| EP | 4659795 | 12/2025 |
| ES | 2222819 | 3/2006 |
| ES | 2272137 | 6/2008 |
| GB | 2496449 | 5/2013 |
| JP | 2010-527256 | 1/1900 |
| JP | 2002-200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |
| JP | 2008-018235 | 1/2008 |
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 | 3/2014 |
| JP | 2015-514460 | 5/2015 |
| JP | 2016-511651 | 4/2016 |
| JP | 2018-038597 | 3/2018 |
| JP | 2018-516702 | 6/2018 |
| KR | 20130104446 | 9/2013 |
| WO | WO 1987/01024 | 2/1987 |
| WO | WO 1994/000187 | 1/1994 |
| WO | WO 1994/017855 | 8/1994 |
| WO | WO 95/19804 | 7/1995 |
| WO | WO 1996/032909 | 10/1996 |

(56) References Cited

FOREIGN PATENT DOCUMENTS

| | | |
|---|---|---|
| WO | WO 98/23326 | 6/1998 |
| WO | WO 98/40121 | 9/1998 |
| WO | WO 1998/043700 | 10/1998 |
| WO | WO 1999/019019 | 4/1999 |
| WO | WO 2000/015293 | 3/2000 |
| WO | WO 2000/076436 | 12/2000 |
| WO | WO 01/03768 | 1/2001 |
| WO | WO 2001/087411 | 11/2001 |
| WO | WO 2002/017987 | 3/2002 |
| WO | WO 2002/034327 | 5/2002 |
| WO | WO 03/015866 | 2/2003 |
| WO | WO 2004/037344 | 5/2004 |
| WO | WO 2004/067087 | 8/2004 |
| WO | WO 2004/108209 | 12/2004 |
| WO | WO 2005/007029 | 5/2005 |
| WO | WO 2005/105201 | 11/2005 |
| WO | WO 2005/0122894 | 12/2005 |
| WO | WO 2006/021820 | 3/2006 |
| WO | WO 2006/044793 | 4/2006 |
| WO | WO 2006/054118 | 5/2006 |
| WO | WO 2006/092007 | 9/2006 |
| WO | WO 2006/102724 | 10/2006 |
| WO | WO 2007/056493 | 5/2007 |
| WO | WO 2007/092290 | 8/2007 |
| WO | WO 2007/112092 | 10/2007 |
| WO | WO 2008/005478 | 1/2008 |
| WO | WO 2008/045598 | 4/2008 |
| WO | WO 2008/062395 | 5/2008 |
| WO | WO 2008/106174 | 9/2008 |
| WO | WO 2008/150591 | 12/2008 |
| WO | WO 2009/005797 | 1/2009 |
| WO | WO 2009/153730 | 12/2009 |
| WO | WO 2010/014260 | 2/2010 |
| WO | WO 2010/031055 | 3/2010 |
| WO | WO 2010/111321 | 9/2010 |
| WO | WO 2010/141155 | 12/2010 |
| WO | WO 2011/106225 | 9/2011 |
| WO | WO 2011/119224 | 9/2011 |
| WO | WO 2011/144883 | 11/2011 |
| WO | WO 2011/149656 | 12/2011 |
| WO | WO 2012/040243 | 3/2012 |
| WO | WO 2012/074794 | 6/2012 |
| WO | WO 2012166860 | 12/2012 |
| WO | WO 2013012625 | 1/2013 |
| WO | WO 2013/071307 | 5/2013 |
| WO | WO 2013/074809 | 5/2013 |
| WO | WO 2013/173727 | 11/2013 |
| WO | WO 2014/043757 | 3/2014 |
| WO | WO 2014040007 | 3/2014 |
| WO | WO 2014040018 | 3/2014 |
| WO | WO 2014040023 | 3/2014 |
| WO | WO 2014/053041 | 4/2014 |
| WO | WO 2014055507 | 4/2014 |
| WO | WO 2014/070999 | 5/2014 |
| WO | WO 2014/089549 | 6/2014 |
| WO | WO 2014/093964 | 6/2014 |
| WO | WO 2014/113813 | 7/2014 |
| WO | WO 2014/146082 | 9/2014 |
| WO | WO 2014/151431 | 9/2014 |
| WO | WO 2014/153201 | 9/2014 |
| WO | WO 2014138022 | 9/2014 |
| WO | WO 2014/207512 | 12/2014 |
| WO | WO 2015/033152 | 3/2015 |
| WO | WO 2015/039206 | 3/2015 |
| WO | WO 2015/039244 | 3/2015 |
| WO | WO 2015/042365 | 3/2015 |
| WO | WO 2015/079319 | 6/2015 |
| WO | WO 2015/085880 | 6/2015 |
| WO | WO 2015/095880 | 6/2015 |
| WO | WO 2015/128090 | 9/2015 |
| WO | WO 2015/138981 | 9/2015 |
| WO | WO 2015/148184 | 10/2015 |
| WO | WO 2015/164706 | 10/2015 |
| WO | WO 2015/187712 | 12/2015 |
| WO | WO 2016/007093 | 1/2016 |
| WO | WO 2016/019250 | 2/2016 |
| WO | WO 2016/032929 | 3/2016 |
| WO | WO 2016/094728 | 6/2016 |
| WO | WO 2016/102958 | 6/2016 |
| WO | WO 2016/110804 | 7/2016 |
| WO | WO 2016/128985 | 8/2016 |
| WO | WO 2016/149751 | 9/2016 |
| WO | WO 2016/166281 | 10/2016 |
| WO | WO 2016/176668 | 11/2016 |
| WO | WO 2016/179407 | 11/2016 |
| WO | WO 2016/189422 | 12/2016 |
| WO | WO 2016/195587 | 12/2016 |
| WO | WO 2016/201366 | 12/2016 |
| WO | WO 2017/004021 | 1/2017 |
| WO | WO 2017/010930 | 1/2017 |
| WO | WO 2017/023864 | 2/2017 |
| WO | WO 2017/044904 | 3/2017 |
| WO | WO 2017/053847 | 3/2017 |
| WO | WO 2017/062994 | 4/2017 |
| WO | WO 2017/086798 | 5/2017 |
| WO | WO 2017/088573 | 6/2017 |
| WO | WO 2017/105930 | 6/2017 |
| WO | WO 2017/132067 | 8/2017 |
| WO | WO 2017/199026 | 11/2017 |
| WO | WO 2017/208167 | 12/2017 |
| WO | WO 2017/209673 | 12/2017 |
| WO | WO 2017/210729 | 12/2017 |
| WO | WO 2017/221037 | 12/2017 |
| WO | WO 2018/009680 | 1/2018 |
| WO | WO 2018/028170 | 2/2018 |
| WO | WO 2018/028220 | 2/2018 |
| WO | WO 2018/028221 | 2/2018 |
| WO | WO 2018/039458 | 3/2018 |
| WO | WO 2018/093765 | 5/2018 |
| WO | WO 2018/106839 | 6/2018 |
| WO | WO 2018/112164 | 6/2018 |
| WO | WO 2018119220 | 6/2018 |
| WO | WO 2018/187241 | 10/2018 |
| WO | WO 2019/005774 | 1/2019 |
| WO | WO 2019/014250 | 1/2019 |
| WO | WO 2019/028000 | 2/2019 |
| WO | WO 2019/046180 | 3/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |
| WO | WO 2020/006048 | 1/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2020/252406 | 12/2020 |
| WO | WO 2021/005584 | 1/2021 |
| WO | WO 2021/055716 | 3/2021 |
| WO | WO 2021/062345 | 4/2021 |
| WO | WO 2021/092533 | 5/2021 |
| WO | WO 2021/127422 | 6/2021 |
| WO | WO 2021/228128 | 11/2021 |
| WO | WO 2021/236815 | 11/2021 |
| WO | WO 2021/252292 | 12/2021 |
| WO | WO 2022/090834 | 5/2022 |
| WO | WO 2022/187318 | 9/2022 |
| WO | WO 2022/187486 | 9/2022 |
| WO | WO 2022/221858 | 10/2022 |
| WO | WO 2022/235607 | 11/2022 |
| WO | WO 2023/283568 | 1/2023 |
| WO | WO 2023/014499 | 2/2023 |
| WO | WO 2023/015158 | 2/2023 |
| WO | WO 2023/015159 | 3/2023 |
| WO | WO 2023/129722 | 7/2023 |
| WO | WO 2023/156391 | 8/2023 |
| WO | WO 2023/163300 | 8/2023 |
| WO | WO 2023/168016 | 9/2023 |
| WO | WO 2023/191236 | 10/2023 |
| WO | WO 2023/192519 | 10/2023 |
| WO | WO 2023/196578 | 10/2023 |
| WO | WO 2023/215558 | 11/2023 |

(56) References Cited

FOREIGN PATENT DOCUMENTS

| | | |
|---|---|---|
| WO | WO 2023/222911 | 11/2023 |
| WO | WO 2024/059136 | 3/2024 |
| WO | WO 2024/059140 | 3/2024 |
| WO | WO 2024/059141 | 3/2024 |
| WO | WO 2024/059643 | 3/2024 |
| WO | WO 2024/059651 | 3/2024 |
| WO | WO 2024/059663 | 3/2024 |
| WO | WO 2024/083685 | 4/2024 |
| WO | WO 2024/086209 | 4/2024 |
| WO | WO 2024/119042 | 6/2024 |
| WO | WO 2024/155527 | 7/2024 |
| WO | WO 2024/182256 | 9/2024 |
| WO | WO 2024/206883 | 10/2024 |
| WO | WO 2024/215916 | 10/2024 |
| WO | WO 2024/238988 | 11/2024 |
| WO | WO 2025/010365 | 1/2025 |
| WO | WO 2025/015047 | 1/2025 |
| WO | WO 2025/024798 | 1/2025 |
| WO | WO 2025/029692 | 2/2025 |
| WO | WO 2025/029698 | 2/2025 |
| WO | WO 2025/038457 | 2/2025 |
| WO | WO 2025/038622 | 2/2025 |
| WO | WO 2025/049694 | 3/2025 |
| WO | WO 2025/069021 | 4/2025 |
| WO | WO 2025/080428 | 4/2025 |
| WO | WO 2025/081022 | 4/2025 |
| WO | WO 2025/219728 | 4/2025 |
| WO | WO 2025068762 | 4/2025 |
| WO | WO 2025/099587 | 5/2025 |
| WO | WO 2025/104232 | 5/2025 |
| WO | WO 2025/117608 | 6/2025 |
| WO | WO 2025/117609 | 6/2025 |
| WO | WO 2025/128510 | 6/2025 |
| WO | WO 2025/128825 | 6/2025 |
| WO | WO 2025/133597 | 6/2025 |
| WO | WO 2025/136631 | 6/2025 |
| WO | WO 2025/151398 | 7/2025 |
| WO | WO 2025/151439 | 7/2025 |
| WO | WO 2025/155529 | 7/2025 |
| WO | WO 2025/175157 | 8/2025 |
| WO | WO 2025/177139 | 8/2025 |
| WO | WO 2025/193607 | 9/2025 |
| WO | WO 2025/247161 | 12/2025 |
| WO | WO 2025/250395 | 12/2025 |
| WO | WO 2025/264783 | 12/2025 |
| WO | WO 2026/003575 | 1/2026 |
| WO | WO 2026/003759 | 1/2026 |
| WO | WO 2026/011148 | 1/2026 |

OTHER PUBLICATIONS

U.S. Appl. No. 15/354,943, filed Nov. 17, 2016, Wong et al.
U.S. Appl. No. 15/580,631, filed Dec. 7, 2017, Wong et al.
U.S. Appl. No. 15/721,475, filed Sep. 29, 2017, Wong et al.
U.S. Appl. No. 15/721,480, filed Sep. 29, 2017, Wong et al.
U.S. Appl. No. 15/748,616, filed Jan. 29, 2018, Hamner et al.
U.S. Appl. No. 15/762,043, filed Mar. 21, 2018, Hamner et al.
U.S. Appl. No. 16/071,056, filed Jul. 18, 2018, wong et al.
U.S. Appl. No. 16/241,846, filed Jan. 7, 2019, wong et al.
U.S. Appl. No. 16/242,983, filed Jan. 8, 2019, wong et al.
U.S. Appl. No. 16/247,310, filed Feb. 22, 2019, Wong et al.
U.S. Appl. No. 16/327,780, filed Feb. 22, 2019, Hamner et al.
U.S. Appl. No. 16/780,758, filed Feb. 3, 2020, Hamner et al.
U.S. Appl. No. 16/792,100, filed Feb. 14, 2020, Hamner et al.
U.S. Appl. No. 16/833,388, filed Mar. 27, 2020, Hamner et al.
U.S. Appl. No. 16/962,810, filed Jul. 16, 2002, Hamner et al.
U.S. Appl. No. 16/993,085, filed Aug. 13, 2020, Balbaky et al.
U.S. Appl. No. 17/013,396, filed Sep. 4, 2020, Wong et al.
U.S. Appl. No. 17/052,483, filed Nov. 2, 2020, Liberatore et al.
U.S. Appl. No. 17/061,231, filed Oct. 1, 2020, Yu.
U.S. Appl. No. 17/080,544, filed Oct. 26, 2020, Wong et al.
U.S. Appl. No. 17/633,004, filed May 11, 2020, Wong et al.
U.S. Appl. No. 17/633,010, filed May 11, 2022, Wong et al.
Amarenco et al. "Urondynamic Effect of Acute Transducteaneous Posterior Tibial Nerve Stimulation in Overactive Bladder" Journal of Urology vol. 169, 2210-2215 (Jun. 2003).
Apartis; Clinical neurophysiology in movement disorders. Handb Clin Neurol; 111; Pediatric Neurology Pt. 1; pp. 87-92;Apr. 2013.
Barath et al., 2020, Brain metabolic changes with longitudinal transcutaneous afferent patterned stimulation in essential tremor subjects, Tremor and Other Hyperkinetic Movements, 10(1):52, pp. 1-10.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brillman et al., 2022, Real-world evidence of transcutaneous afferent patterned stimulation for essential tremor, Tremor and Other Hyperkinetic Movements, 12(1):27, pp. 1-11.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006.
Buschbacher et al.; Manual of nerve conduction series; 2nd edition; Demos Medical Publishing, LLC; 2006 (part 2, p. 143 to 299).
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fascicles in the human superficial radial nerve; Brain; 128(Pt 4); pp. 892-895; Apr. 2005.

(56) References Cited

OTHER PUBLICATIONS

Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congress on Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; 1998.
Di Giovangiulio et al.; The Neuromodulation of the intestinal immune system and its relevance in inflammatory bowel disease; Frontier's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Biosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Ferreira et al., 2019, MDS evidence-based review of treatments for essential tremor, Movement Disorders, 34(7):950-958.
Fiorentino et al., 2011, Self calibrating wearable active running asymmetry measurement and correction, Journal of Control Engineering and Applied Informatics, 13(2):3-8.
Fred E. Govier, et al., "Percutaneous Afferent Neuromodulation for the Refractory Overactive Bladder: Results of a Multicenter Study," 165 J. Urology 1193-1198 (Apr. 2001).
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; Real-time estimation of pathological tremor parameters from gyroscope data.; Sensors; 10(3); pp. 2129-2149; Mar. 2010.
Gallego et al; A soft wearable robot for tremor assessment and suppression; 2011 IEEE International Conference on Robotics and Automation; Shanghai International Conference Center; pp. 2249-2254; May 9-13, 2011.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagal afferent nerve stimulation in migraine patients; Pain; International Association for the Study of Pain; 2017.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulation of innervated muscle; Archives of Physical Medicine and Rehabilitation; 56(6); pp. 243-249; Jun. 1975.
Gupta et al., 2021, Exploring essential tremor: results from a large online survey, Clinical Parkinsonism & Related Disorders, 5:100101, 4 pp.
H.C. Klingler, et al., "Use of Peripheral Neuromodulation of the S3 Region for Treatment of Detrusor Overactivity: A Urodynamicbased Study," Urology 56:766-771, 2000.
Haeri et al.; Modeling the Parkinson's tremor and its treatments; Journal of Theoretical Biology; 236(3); pp. 311-322; Oct. 2005.
Halonen et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Haubenberger et al., 2018, Essential Tremor, The New England Journal of Medicine, 378:1802-1810 and Supplementary Appendix.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Hellwig et al., Feb. 17, 2001, Tremor-correlated cortical activity in essential tremor, The Lancet, 357:519-523.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170-175.
Hernandez-Martin et al., 2021, High-fidelity transmission of high-frequency burst stimuli from peripheral nerve to thalamic nuclei in children with dystonia, Scientific Reports, 11:8498, 9 pp.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurology and urodynamics 30.8 (2011): 1467-1472.
Inoue et al. "Stretchable human interface using a conductive silicone elastomer containing silver fillers." Consumer Electronics, 2009. ISCE'09. IEEE 13th International Symposium on. IEEE, 2009.
Isaacson et al., 2020, Prospective home-use study on non-invasive neuromodulation therapy for essential tremor, Tremor and Other Hyperkinetic Movements, 10(1):29, pp. 1-16.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.

(56) References Cited

OTHER PUBLICATIONS

Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Krishnamoorthy et al., 2008, Gait Training After Stroke: A Pilot Study Combining a Gravity-Balanced Orthosis, Functional Electrical Stimulation, and Visual Feedback, Journal of Neurologic Physical Therapy, 32(4):192-202.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Neurology; 10(6); pp. 523-531; Dec. 1981.
Legon et al.; Pulsed ultrasound differentially stimulates somatosensory circuits in humans as indicated by EEG and fMRI; PLoS One; 7(12); e51177; 14 pgs.; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lin et al., 2018, Noninvasive neuromodulation inessential tremor demonstrates relief in a sham-controlled pilot trial, Movement Disorders, 33(7):1182-1183.
Llinas et al., Dec. 21, 1999, Thalamocortical dysrhythmia: a neurological and neuropsychiatric syndrome characterized by magnetoencephalography, PNAS, 96(26):15222-15227.
Lourenco et al.; Effects produced in human arm and forearm motoneurons after electrical stimulation of ulnar and median nerves at wrist level; Experimental Brain Research; 178(2); pp. 267-284; Apr. 2007.
Lyons et al., 2021, Essential tremor in adult patients, International Essential Tremor Foundation, 16 pp.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurology and urodynamics 28.4 (2009): 313-319.
Michael R. Van Balken, et al., "Posterior Tibial Nerve Stimulation as Neuromodulative Treatment of Lower Urinary Track Dysfunction," 166 J. Urology 914-918 (Sep. 2001).
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus ?; Results of a Questionnaire, Parkinsonism Relat Disord; 13; pp. 528-531; Dec. 2007.
Munhoz et al; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
Pahwa et al., 2018, An acute randomized controlled trial of noninvasive peripheral nerve stimulation in essential tremor, Neuromodulation, 22:537-545.
Peng et al., 2015, Flexible dry electrode based on carbon nanotube/polymer hybrid micropillars for biopotential recording, Sensor and Actuatora A: Physical, 235:48-65.
Perez et al.; Patterned Sensory Stimulation Induces Plasticity in Reciprocal la Inhibition in Humans; The Journal of Neuroscience; 23(6); pp. 2014-2018; Mar. 2003.
Perez-Reyes, Jan. 2003, Molecular physiology of low-voltage-activated T-type calcium channels, Physiol. Rev. 83:117-161.
Perlmutter et al.; Deep brain stimulation; Ann Rev Neurosci; 29; pp. 229-257; Jul. 2006.
Popovi Maneski et al.; Electrical stimulation for the suppression of pathological tremor; Medical & Biological Engineering & Computing; 49(10); pp. 1187-1193; Oct. 2011.
Popovic-Bijelic et al. "Multi-field surface electrode for selective electrical stimulation." Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Sigrist et al., 2012. Augmented visual, auditory, haptic, and multimodal feedback in motor learning: A review. Psychonomic Bulletin & Review, 20(1):21-53.
Silverstone et al.; Non-Invasive Neurostimulation In The Control of Familial Essential Tremor Using The Synaptic Neuromodulator;

(56) References Cited

OTHER PUBLICATIONS

Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Solomonow et al., 1998, Studies toward spasticity suppression with high frequency electrical stimulation, Orthopedics, 7(8):1284-1288.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Biol Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Tolosa et al.; Essential tremor: treatment with propranolol; Neurology; 25(11); pp. 1041; Nov. 1975.
Tracey; The inflammatory reflex; Nature; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecal Incontinence in inflammatory bowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wallerberger, Apr. 4, 2019, Efficient Estimation of Autocorrelation Spectra, ArXiv.org, https://arxiv.org/abs/1810.05079.
Wardman et al.; Subcortical, and cerebellar activation evoked by selective stimulation of muscle and cutaneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol;249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh et al., "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.
Cala Trio Health Care Professional Guide (Jul. 2020).
Cala Trio Health Care Professional Guide (Nov. 2019).
Chang, M.D., Qwang-Yuen et al., Effect of Electroacupuncture and Transcutaneous Electrical Nerve Stimulation at Hegu (LI.4) Acupuncture Point on the Cutaneous Reflect, 27 Acupuncture & Electro-Therapeutics Res., Int. J. 191-202 (2002).
Javidan, et al, Attenuation of Pathological Tremors by Functional Electrical Stimulation II: Clinical Evaluation, 20 Annals of Biomedical Engineering 225 (1992).
Knutson et al., Neuromuscular Electrical Stimulation for Motor Restoration in Hemiplegia. Phys Med Rehabil Clin N A,. Nov. 2015; 26(4):729-745. Published online Aug. 14, 2015. Doi: 10.1016/j.pmr.2015.06.002.
PTAB-IPR2024-00732—Exhibit 1002—Declaration of John Laughlin, M. Eng., P.E., in 109 pages.
PTAB-IPR2024-00732—Petition for Inter Partes Review of U.S. Pat. No. 10,786,669, filed Mar. 29, 2024, in 101 pages.
PTAB-IPR2024-00743—Exhibit 1002—Declaration of John Laughlin, M. Eng., P.E., in 102 pages.
PTAB-IPR2024-00743—Petition for Inter Partes Review of U.S. Pat. No. 11,628,300, filed Mar. 29, 2024, in 113 pages.
Aemed, Inc., 510(k) Summary, StimPad™ TENS System, Dec. 6, 2007.
Antal et al., Anodal Transcranial Direct Current Stimulation of the Motor Cortex Ameliorates Chronic Pain and Reduces Short Intracortical Inhibition, Journal of Pain and Symptom Management, vol. 39, No. 5, pp. 890-903, May 2010.
Cala kIQ, calahealth.com, [online], [site visited Mar. 7, 2025], Available from internet URL: https://calahealth.com/ (Year: 2025).
De Santana, et al., Effectiveness of Transcutaneous Electrical Nerve Stimulation for Treatment of Hyperalgesia and Pain, Curr Rheumatol Rep.; 10(6): 492-499, Dec. 2008.
Dewey, et al., A Pilot Study of Ai-Controled Transcutaneous Peripheral Nerve Stimulation for Essential Tremor, Tremor and Other Hyperkinetic Movements, 2025; 15(1):10, pp. 1-9.
Encore Medical, L.P., Intelect Transport 2 Channel Electrotherapy User Manual, 2005.
Falco et al., Cross Talk: A New Method for Peripheral Nerve Stimulation. An Observational Report with Cadaveric Verification, Pain Physician, 12:965-983, 2009.
Fowler et al., The conduction velocities of peripheral nerve fibres conveying sensations of warming and cooling, Journal of Neurology, Neurosurgery and Psychiatry Sep. 1988;51(9):1164-70.
Griffin et al., Efficacy of High Voltage Pulsed Current for Healing of Pressure Ulcers in Patents with Spinal Cord Injury, Physical Therapy, vol. 71, No. 6, Jun. 1991, pp. 433-442.
Johnson, Factors Influencing The Analgesic Effects and Clinical Efficacy of Transcutaneous Electrical Nerve Stimulation (TENS), Newcastle University, Jul. 1991.
Jones et al., Transcutaneous electronical nerve stimulation, Continuing Education in Anesthesia, Critical Care & Pain, vol. 9, No. 4, pp. 130-135, 2009.
Korkmaz et al., Pulsed radiofrequency versus conventional transcutaneous electrical nerve stimulation in painful shoulder: a prospective, randomized study, Clin Rehabil. Nov. 2010;24(11):1000-8, Aug. 4, 2010.
Lowry et al., Spinal Cord Stimulation for the Treatment of Chronic Knee Pain Following Total Knee Replacement, Pain Physician, 13:251-256, 2010.
Miller et al., Superimposed single impulse and pulse train electrical stimulation: A quantitative assessment during submaximal isometric knee extension in young, healthy men, Superimposed Electrical Stimulation Techniques, Muscle & Nerve, Aug. 1999, pp. 1038-1046.
Trends in the Health Wearable Technology, first available Oct. 26, 2021, mokosmart.com, [online], [site visited Mar. 7, 2025], Available from internet URL: https://www.mokosmart.com/health-wearable-technology-trends/ (Year: 2021).
Feinstein Institutes for Medical Research, Northwell Health; High-frequency electrical stimulation helps reduce inflammation pain in new Feinstein Institute study; Press Release Oct. 5, 2022.

(56) References Cited

OTHER PUBLICATIONS

Yang et al.; High-frequency electrical stimulation attenuates neuronal release of inflammatory mediators and ameliorates neuropathic pain, Bioelectronic Medicine, 8(1); pp. 1-13; Oct. 5, 2022.
Hu et al., Pain modulation effect of breathing-controlled electrical stimulation (BreEStim) is not likely to be mediated by deep and fast voluntary breathing. Sci Rep 5, 14228 (2015). (Year: 2015).
Lauk et al, "A software for recording and analysis of human tremor," Computer Methods and Programs in Biomedicine 60 (1999) 65-77, https://www.sciencedirect.com/science/article/pii/S0169260799000127?via%3Dihub.
Nouman et al; Additive blooming in polymer materials: Consequences in the pharmaceutical and medical field, Polymer Degradation and Stability, vol. 143, Sep. 2017, pp. 239-252 (Year: 2017).
Pain & Spine Specialists (Apr. 12, 2024). Identifying Symptoms of Diabetic Neuropathy. https://painandspinespecialists.com/ identifying-symptoms-of-diabetic-neuropathy/ (Year: 2024).
Rajaraman et al, "A novel quantitative method for 3D measurement of Parkinsonian tremor," Clin Neurophysiol, Feb. 2000; 111(2):338-43, https://pubmed.ncbi.nlm.nih.gov/10680570/.
Technical Presentation: Third-Stream Additives that Modify LSR and HCR, Nov. 13, 2020 [online]; RDAbbott webpage; hyperlink titled "presentation"; [https://rdabbott.com/wp-content/uploads/2020/11/ISC2020-Third-Stream-Additives-for-LSR-and-HCR_20201113.pdf], p. 20, p. 23 (Year: 2020).
Wang et al.; Mechanically Flexible Conductors for Stretchable and Wearable E-Skin and E-Textile Devices, May 2019; [https://doi.org/10.1002/adma.201901408] (Year: 2019).

* cited by examiner

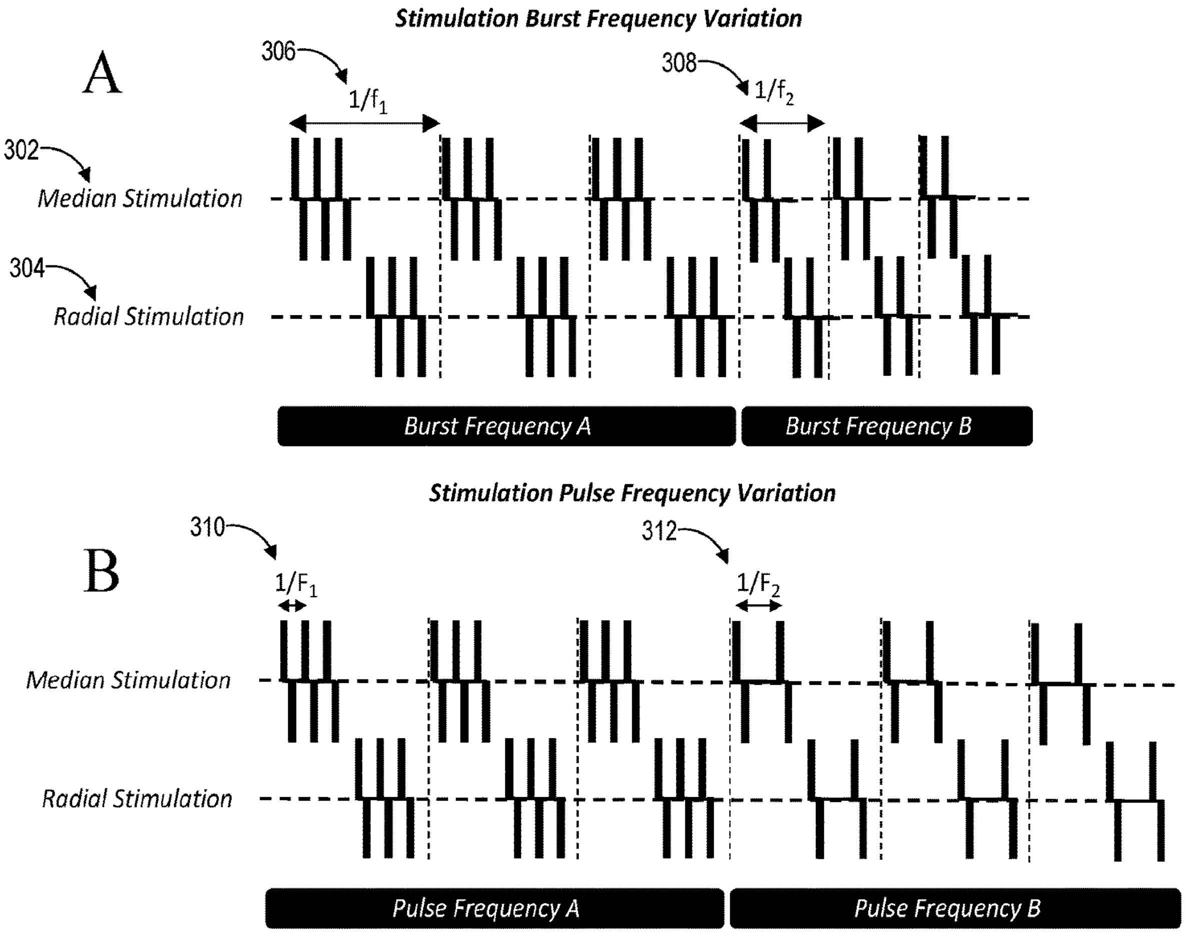
Figures 3A-B

A
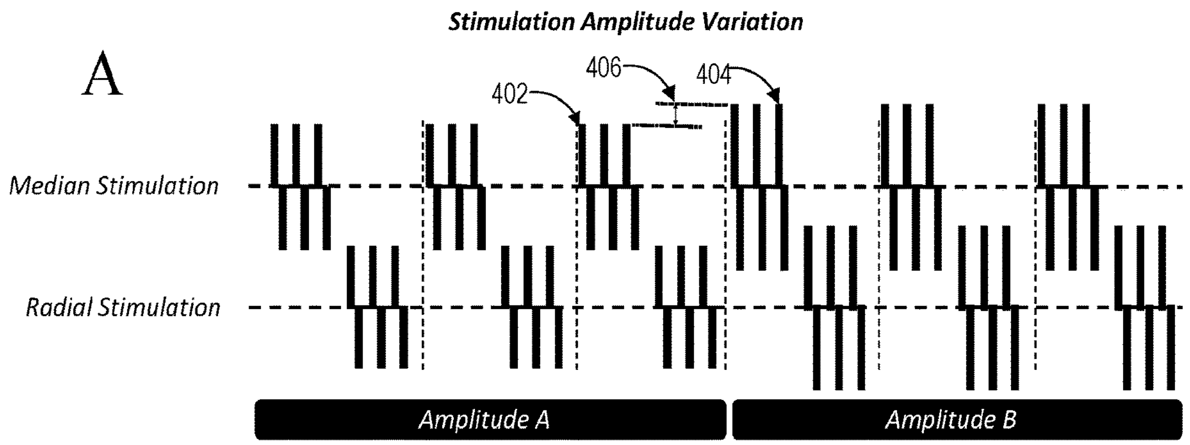
B
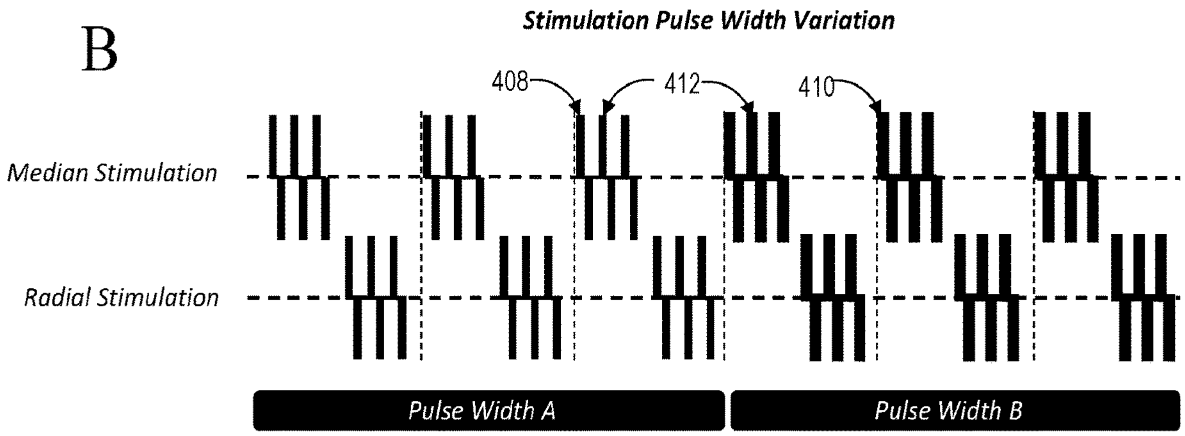
Figures 4A-B

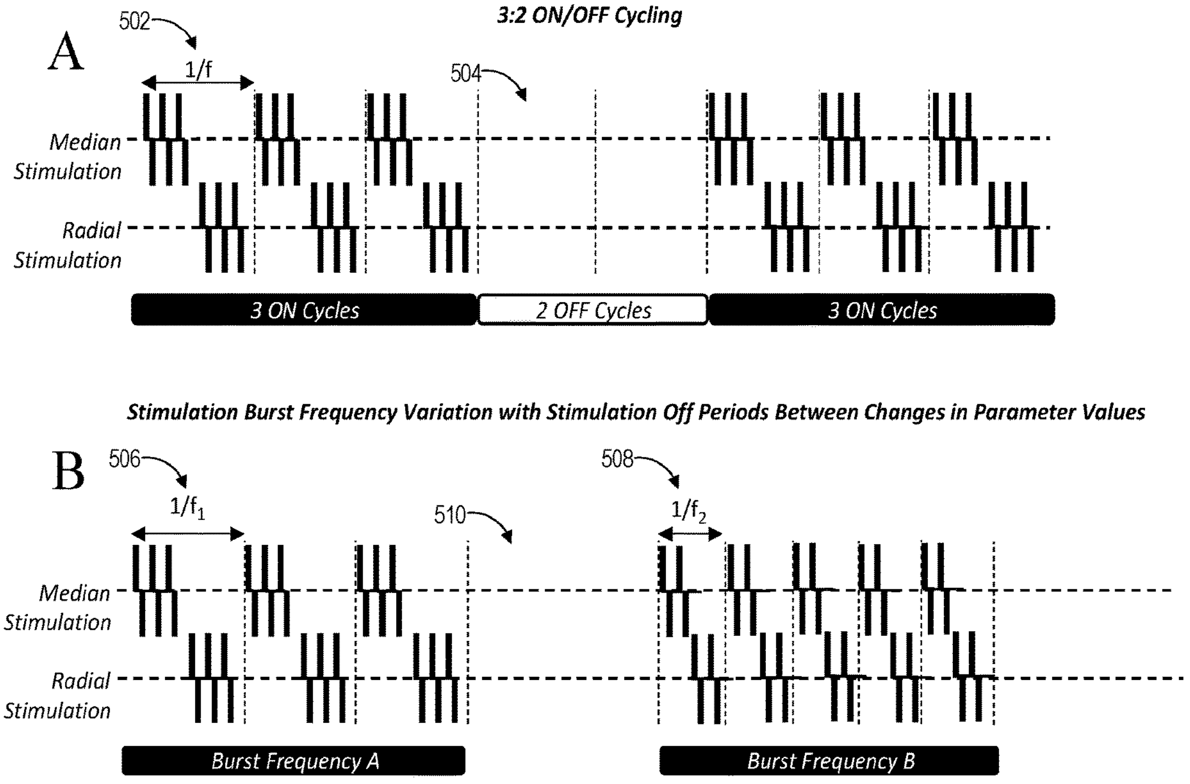
Figures 5A-B

PARAMETER VARIATION IN NEURAL STIMULATION

REFERENCE TO RELATED APPLICATIONS

This application claims the benefit of U.S. Provisional Application No. 63/027,806, filed May 20, 2020, which is hereby incorporated by reference in its entirety.

BACKGROUND

Field of Invention

Embodiments of the invention relate generally to systems, devices, and methods for stimulating nerves, and more specifically relate to system, devices, and methods for electrically stimulating peripheral nerve(s) to treat various diseases and disorders, as well as systems and methods for applying stimulation waveforms for improving the therapeutic benefit, outcomes, and/or experience relating to the same.

Description of Related Art

Electrical energy can be delivered transcutaneously via electrodes on the skin surface with neurostimulation systems to stimulate peripheral nerves. Essential tremor is a common movement disorder, with growing numbers due to the aging population. Tremor in the hands and forearm is especially prevalent and problematic because it makes it difficult to write, type, eat, and drink. Disorders, including essential tremor, may be treated by pharmaceutical agents, which can cause undesired side effects. Applicant's prior treatment of tremor and other disorders has been effective in many cases (see, for example, U.S. Pat. No. 9,452,287).

SUMMARY

Embodiments of the neurostimulation system disclosed herein accommodate variability in pathological tremor characteristics including variations in tremor pathology for a user. For example, the frequency of a tremor experienced by the user is not constant over time. The neurostimulation system can deliver a stimulation waveform that varies one or more parameters, as opposed to delivering a constant value, to improve the therapeutic response of the stimulation. For example, adding variation in burst frequency may account for natural variation in pathological tremor frequency. In some cases, pathological tremor frequency can change, for example, by more than 2 Hz between tasks and by up to 32% on the same task over time within an individual subject. Calibrating burst frequency to tremor frequency can improve therapeutic effect.

In certain embodiments, stimulation parameters are agnostic for any particular individual and may be varied within generally known therapeutic ranges during the course of stimulation. Adding variation in pulse frequency may account for individual differences in the brain response to peripheral nerve stimulation. For example, the evoked response generated in the ventral intermediate nucleus of the thalamus by median nerve stimulation was maximized at a pulse frequency of 50 Hz in some subjects and 100 Hz in other subjects. By varying pulse frequency throughout these range of values, the brain response is maximized during some portion of the therapy session for every individual, which may enhance therapeutic benefit.

In various embodiments, one or more of the following nerves are treated such as the median, radial, and/or ulnar nerves in the upper extremities, tibial, saphenous, and/or peroneal nerve in the lower extremities; or the auricular vagus, tragus, trigeminal or cranial nerves on the head or ear, as non-limiting examples. Stimulation of these nerves, according to several embodiments described herein, are used to treat essential tremor, Parkinson's tremor, orthostatic tremor, and multiple sclerosis, urological disorders, gastrointestinal disorders, cardiac diseases, and mood disorders (including but not limited to depression, bipolar disorder, dysthymia, and anxiety disorder), pain syndromes (including but not limited to migraines and other headaches, trigeminal neuralgia, fibromyalgia, complex regional pain syndrome), Lyme disease, stroke, among others. Inflammatory bowel disease (such as Crohn's disease), rheumatoid arthritis, multiple sclerosis, psoriatic arthritis, psoriasis, chronic fatigue syndrome, and other inflammatory diseases are treated in several embodiments. Cardiac conditions (such as atrial fibrillation) are treated in one embodiment. Inflammatory skin conditions and immune dysfunction are also treated in some embodiments.

In some embodiments, disclosed herein is a neuromodulation system to modulate one or more peripheral nerves of an arm, hand, wrist, leg, ankle, foot, head, face, neck or ear. In one embodiment, neuromodulation comprises neuromodulation of a first peripheral nerve, a processor and a memory for storing instructions that, when executed by the processor cause the device to neuromodulate a first peripheral nerve for a prespecified amount of time and vary one or more parameters over a prespecified range of parameters at a prespecified rate of variation. Parameters, include for example, burst frequency, pulse frequency, pulse width, intensity, and/or on/off cycling. Nonimplantable stimulation via electrodes in a wearable system is provided in several embodiments. Wearable systems include devices that, for example, are placed on the upper arm, upper leg, wrist, finger, ankle, ear, face and neck.

In some embodiments, disclosed herein is a neurostimulation system to stimulate one or more peripheral nerves of an arm, hand, wrist, leg, ankle, foot, head, face, neck or ear, comprising: a first peripheral nerve electrode configured to be positioned to deliver stimulation to a first peripheral nerve; and a processor and a memory for storing instructions that, when executed by the processor cause the device to: deliver stimulation to a first peripheral nerve for a prespecified amount of time; and vary one or more parameters of the first stimulus over a prespecified range of parameters at a prespecified rate of variation, where the parameters could include burst frequency, pulse frequency, pulse width, intensity, and/or on/off cycling. In some embodiments, the varied parameter is restricted to (e.g., consists essentially of or comprises) burst frequency, the range of parameters is restricted to 3-12 Hz (e.g., 3-5, 5-8, 8-12 Hz, and overlapping ranges therein), and the rate of variation is restricted to (e.g., consists essentially of or comprises) 0.001-100 Hz/s (e.g., 0.001-0.01, 0.01-0.1, 0.1-1, 1-10, 10-100 Hz, and overlapping ranges therein). In some embodiments, the varied parameter is restricted to pulse frequency, the range of parameters is restricted to (e.g., consists essentially of or comprises) 50-150 Hz (e.g., 50-100, 100-150 Hz, and overlapping ranges therein), and the rate of variation is restricted to (e.g., consists essentially of or comprises) 0.001-10,000 Hz/s(e.g., 0.001-0.01, 0.01-0.1, 0.1-1, 1-10, 10-100,100-1,000,1,000-10,000 Hz/s). In some embodiments, the varied parameter is restricted to (e.g., consists essentially of or comprises) pulse width, the range of parameters is restricted to (e.g., consists essentially of or comprises) a minimum value from one of 100, 150, 200, 250, 300, or 350 microseconds and a maximum pulse width based on an individual's comfort level at a fixed stimulation amplitude, and the rate of variation is restricted to (e.g., consists essentially of or comprises) 0.01-10,000 microseconds per second (e.g., 0.01-0.1, 0.1-1, 1-10, 10-100, 100-1,0000,1,000-10,000 microseconds per second, and overlapping ranges therein). In some embodiments, the fixed stimulation amplitude is based on an individual's sensory level with a fixed pulse width in a range between 100-500 microseconds (e.g., 100-200, 200-300, 300-400, 400-500 microseconds, and overlapping ranges therein).

In some embodiments, the varied parameter is restricted to (e.g., consists essentially of or comprises) stimulation amplitude, the range of parameters is restricted to (e.g., consists essentially of or comprises) a minimum set to the stimulation amplitude at an individual's minimum sensory threshold and a maximum set to the stimulation amplitude at an individual's maximum comfort level, and the rate of variation is restricted to (e.g., consists essentially of or comprises) 0.001-10 mNs (e.g., 0.001-0.01, 0.01-0.1, 0.1-1, 1-10 mNs, and overlapping ranges therein). In some embodiments, the varied parameter is restricted to (e.g., consists essentially of or comprises) stimulation amplitude, the range of parameters is restricted to (e.g., consists essentially of or comprises) a minimum set to a stimulation amplitude at a pre-specified increment below an individual's minimum sensory threshold (sub-sensory) and a maximum set to the stimulation amplitude at an individual's maximum comfort level and the rate of variation is restricted to (e.g., consists essentially of or comprises) 0.001-10 mNs. In some embodiments, the pre-specified increment is one of 0.1, 0.2, 0.25, 0.3, 0.4, 0.5, 0.6, 0.7, 0.75, 0.8, 0.9 or 1 mA.

In some embodiments, the one or more parameters of the first stimulus comprises a first parameter and a second parameter, and wherein the first parameter and the second parameter are simultaneously varied. For example, the first parameter and the second parameter are alternately varied. In some embodiments, the first parameter and the second parameter are varied on different timescales. In some embodiments, the first parameter and the second parameter are varied based on adaptive learning, and wherein the adaptive learning employs at least one of kinematic measurements or satisfaction data. In other embodiments, combinations of timescales, kinematic data and satisfaction data are used.

In some embodiments, disclosed herein is a neurostimulation system to stimulate one or more peripheral nerves of an arm, hand, wrist, leg, ankle, foot, head, face, neck or ear, comprising: a first peripheral nerve electrode configured to be positioned to deliver stimulation to a first peripheral nerve; a processor and a memory for storing instructions that, when executed by the processor cause the device to: deliver stimulation to a first peripheral nerve for a prespecified amount of time; vary one or more parameters of the first stimulus over a prespecified range of parameter, where the parameters could include burst frequency, pulse frequency, pulse width, intensity, and/or on/off cycling; and/or determine the value of the varied parameter based on a prespecified probabilistic distribution.

In some embodiments, the varied parameter is restricted to (e.g., consists essentially of or comprises) burst frequency, the range of parameters is restricted to (e.g., consists essentially of or comprises) 3-12 Hz (e.g., 3-5, 5-8, 8-12 Hz, and overlapping ranges therein), the rate of variation is restricted to (e.g., consists essentially of or comprises) 0.001-100 Hz/s (e.g., 0.001-0.01, 0.01-0.1, 0.1-1,1-10, 10-100 Hz, and overlapping ranges therein.

In some embodiments, a neurostimulation system configured to introduce variability to enhance therapeutic response for a user. The neurostimulation system comprises a first peripheral nerve electrode configured to be positioned to deliver stimulation to a first peripheral nerve and a processor and a memory for storing instructions that, when executed by the processor cause the system to: generate a stimulation waveform configured to be delivered with the first peripheral nerve electrode for a time period; vary one or more parameters of the stimulation waveform to avoid a constant value for the one or more parameters during the time period; and deliver the generated stimulation waveform to the first peripheral nerve electrode for the time period, wherein the variation in the one or more parameters enhances therapeutic response of the stimulation compared to maintaining the one or more parameters constant over the time period.

In some embodiments, a neurostimulation system configured to introduce variability to enhance therapeutic response for a user. The neurostimulation system comprises a first peripheral nerve electrode configured to be positioned to deliver stimulation to a first peripheral nerve; and a processor and a memory for storing instructions that, when executed by the processor cause the system to: generate a stimulation waveform configured to be delivered with the first peripheral nerve electrode for a time period; and vary one or more parameters of the stimulation waveform during the time period without probing one or more characteristics of the medical condition with one or more sensors while delivering the stimulation.

In some embodiments, a neurostimulation system configured to introduce variability to enhance therapeutic response for a user. The neurostimulation system comprises a first peripheral nerve electrode configured to be positioned to deliver stimulation to a first peripheral nerve; a processor and a memory for storing instructions that, when executed by the processor cause the system to: deliver stimulation to a first peripheral nerve for a prespecified amount of time; and simultaneously vary each of a first parameter and a second parameter of the delivered stimulation over a prespecified range at a prespecified rate of variation.

In some embodiments, a neurostimulation system configured to introduce variability to enhance therapeutic response for a user. The neurostimulation system comprises a first peripheral nerve electrode configured to be positioned to deliver stimulation to a first peripheral nerve; a processor and a memory for storing instructions that, when executed by the processor cause the system to: deliver stimulation to a first peripheral nerve for a prespecified amount of time; and alternately vary in a braided manner each of a first parameter and a second parameter of the delivered stimulation over a prespecified range at a prespecified rate of variation.

In some embodiments, a neurostimulation system configured to introduce variability to enhance therapeutic response for a user. The neurostimulation system comprises a first peripheral nerve electrode configured to be positioned to deliver stimulation to a first peripheral nerve; a processor and a memory for storing instructions that, when executed by the processor cause the system to: deliver stimulation to a first peripheral nerve for a prespecified amount of time; and vary each of a first parameter and a second parameter of the delivered stimulation on different timescales over a prespecified range at a prespecified rate of variation.

In some embodiments, a neurostimulation system configured to introduce variability to enhance therapeutic response for a user. The neurostimulation system comprises a first peripheral nerve electrode configured to be positioned to deliver stimulation to a first peripheral nerve; a processor and a memory for storing instructions that, when executed by the processor cause the system to: deliver stimulation to a first peripheral nerve for a prespecified amount of time; and vary each of a first parameter and a second parameter of the delivered stimulation based on adaptive learning over a prespecified range at a prespecified rate of variation, wherein the adaptive learning employs at least one of kinematic measurements or satisfaction data.

In some embodiments, disclosed is a method of stimulating a first peripheral nerve to introduce variability to enhance therapeutic response for a user. The method comprises positioning a first peripheral nerve electrode configured to be positioned to deliver stimulation to a first peripheral nerve; generating a stimulation waveform configured to be delivered with the first peripheral nerve electrode for a time period; and delivering the generated stimulation waveform to the first peripheral nerve electrode for the time period by varying one or more parameters of the stimulation waveform to avoid a constant value for the one or more parameters during the time period, wherein the variation in the one or more parameters enhances therapeutic response of the stimulation compared to maintaining the one or more parameters constant over the time period.

In some embodiments, the one or more parameters are not correlated with characteristics of the user.

In some embodiments, the varying of the one or more parameters is configured to prevent habituation to the delivered stimulation.

In some embodiments, the varying of the one or more parameters is configured to activate neuronal populations of the nerve.

In some embodiments, the varying of the one or more parameters is configured to avoid tolerance effects by the individual.

In some embodiments, the varying of the one or more parameters is configured to resemble physiological neural signaling.

In some embodiments, the processor and the memory are further configured to, when executed by the processor, cause the system to determine the value of the varied parameter based on a prespecified probabilistic distribution.

In some embodiments, the probabilistic distribution is Gaussian.

In some embodiments, the probabilistic distribution is uniform.

In some embodiments, the one or more parameters of the first stimulus comprises a first parameter and a second parameter, and wherein the first parameter and the second parameter are simultaneously or alternately varied.

In some embodiments, a neuromodulation device can comprise any one or more of the embodiments described in the disclosure.

In some embodiments, a method for performing neuromodulation on one or more nerves, comprising any one or more of the embodiments described in the disclosure.

In some embodiments, a system can comprise, not comprise, consist essentially of, or consist of any number of features as disclosed herein.

In some embodiments, a method can comprise, not comprise, consist essentially of, or consist of any number of features as disclosed herein.

Any or all of the devices described herein can be used for the treatment of depression (including but not limited to post-partum depression, depression affiliated with neurological diseases, major depression, seasonal affective disorder, depressive disorders, etc.), inflammation, Lyme disease, stroke, neurological diseases (such as Parkinson's and Alzheimer's), and gastrointestinal issues (including those in Parkinson's disease). Any or all of the devices described herein can be used for the treatment of inflammatory bowel disease (such as Crohn's disease), rheumatoid arthritis, multiple sclerosis, psoriatic arthritis, osteoarthritis, psoriasis and other inflammatory diseases. Any or all of the devices described herein can be used for the treatment of inflammatory skin conditions. Any or all of the devices described herein can be used for the treatment chronic fatigue syndrome. Any or all of the devices described herein can be used for the treatment chronic inflammatory symptoms and flare ups. Systems and methods to reduce habituation and/or tolerance to stimulation in the disorders and symptoms identified herein are provided in several embodiments by, for example, introducing variability in stimulation parameter(s) described herein.

Any or all of the devices described herein can be used for the treatment of cardiac conditions (such as atrial fibrillation). Any or all of the devices described herein can be used for the treatment of immune dysfunction. Any or all of the devices described herein can be used to stimulate the autonomic nervous system. Any or all of the devices described herein can be used to balance the sympathetic/parasympathetic nervous systems.

For purposes of summarizing the disclosure, certain aspects, advantages, and novel features are discussed herein. It is to be understood that not necessarily all such aspects, advantages, or features will be embodied in any particular embodiment of the disclosure, and an artisan would recognize from the disclosure herein a myriad of combinations of such aspects, advantages, or features.

BRIEF DESCRIPTION OF THE DRAWINGS

Non-limiting features of some embodiments of the invention are set forth with particularity in the claims that follow. A better understanding of the features and advantages of some embodiments of the present invention will be obtained by reference to the following detailed description that sets forth illustrative embodiments, in which the principles of the invention are utilized, and the accompanying drawings.

FIGS. 3A-B illustrate examples of how stimulation parameters (e.g., burst frequency and pulse frequency) are varied between two or more prespecified values as stimulation is alternated across two nerves (e.g., median and radial nerve).

FIGS. 4A-B illustrate examples of how stimulation parameters (e.g., amplitude and pulse width) are varied between two or more prespecified values as stimulation is alternated across two nerves (e.g., median and radial nerve).

FIGS. 5A-B illustrate multiple examples of stimulation patterns with prespecified on/off periods as stimulation is alternated across two nerves (e.g., median and radial nerve).

DETAILED DESCRIPTION

Figure 1A:
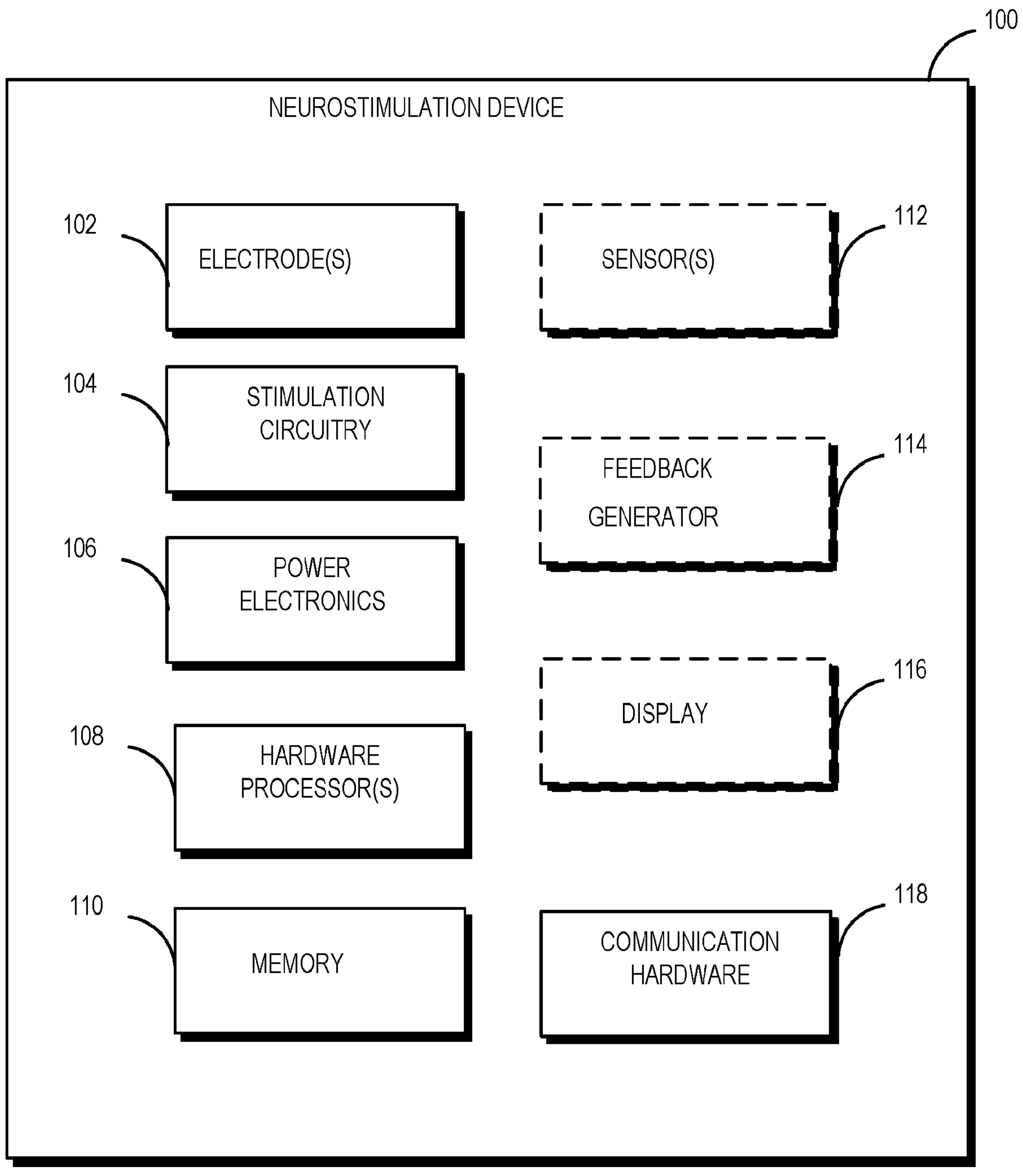
FIG. 1A illustrates a block diagram of an example neuromodulation (e.g., neurostimulation) device.

Disclosed herein are devices configured for providing neuromodulation (e.g., neurostimulation). The neuromodulation (e.g., neurostimulation) devices provided herein may be configured to stimulate peripheral nerves of a user. The neuromodulation (e.g., neurostimulation) devices may be configured to transcutaneously transmit one or more neuromodulation (e.g., neurostimulation) signals across the skin of the user. In many embodiments, the neuromodulation (e.g., neurostimulation) devices are wearable devices configured to be worn by a user. The user may be a human, another mammal, or other animal user. The neuromodulation (e.g., neurostimulation) system could also include signal processing systems and methods for enhancing diagnostic and therapeutic protocols relating to the same. In some embodiments, the neuromodulation (e.g., neurostimulation) device is configured to be wearable on an upper extremity of a user (e.g., a wrist, forearm, arm, and/or finger(s) of a user). In some embodiments, the device is configured to be wearable on a lower extremity (e.g., ankle, calf, knee, thigh, foot, and/or toes) of a user. In some embodiments, the device is configured to be wearable on the head or neck (e.g., forehead, ear, neck, nose, and/or tongue). In several embodiments, dampening or blocking of nerve impulses and/or neurotransmitters are provided. In some embodiments, nerve impulses and/or neurotransmitters are enhanced. In some embodiments, the device is configured to be wearable on or proximate an ear of a user, including but not limited to auricular neuromodulation (e.g., neurostimulation) of the auricular branch of the vagus nerve, for example. The device could be unilateral or bilateral, including a single device or multiple devices connected with wires or wirelessly. In some embodiments, features disclosed for example in U.S. Pat. No. 9,452,287 to Rosenbluth et al., U.S. Pub. No. 2019/0001129 to Rosenbluth et al., U.S. Pat. No. 9,802,041 to Wong et al., and U.S. Pub. No. 2018/0169400 to Wong et al., each of which are hereby incorporated by reference in their entireties, can be combined with systems and methods as disclosed herein.

In several embodiments, neuromodulation systems and methods are provided that enhance or inhibit nerve impulses and/or neurotransmission, and/or modulate excitability of nerves, neurons, neural circuitry, and/or other neuroanatomy that affects activation of nerves and/or neurons. For example, neuromodulation (e.g., neurostimulation) can include one or more of the following effects on neural tissue: depolarizing the neurons such that the neurons fire action potentials; hyperpolarizing the neurons to inhibit action potentials; depleting neuron ion stores to inhibit firing action potentials; altering with proprioceptive input; influencing muscle contractions; affecting changes in neurotransmitter release or uptake; and/or inhibiting firing.

In some embodiments, wearable systems and methods as disclosed herein can advantageously be used to identify whether a treatment is effective in significantly reducing or preventing a medical condition, including but not limited to tremor severity. Wearable sensors can advantageously monitor, characterize, and aid in the clinical management of hand tremor as well as other medical conditions including those disclosed elsewhere herein. Not to be limited by theory, clinical ratings of medical conditions, e.g., tremor severity can correlate with simultaneous measurements of wrist motion using inertial measurement units (IMUs). For example, tremor features extracted from IMUs at the wrist can provide characteristic information about tremor phenotypes that may be leveraged to improve diagnosis, prognosis, and/or therapeutic outcomes. Kinematic measures can correlate with tremor severity, and machine learning algorithms incorporated in neuromodulation systems and methods as disclosed for example herein can predict the visual rating of tremor severity.

In some embodiments, disclosed herein is a neuromodulation system to modulate one or more peripheral nerves of an arm, hand, wrist, leg, ankle, foot, head, face, neck or ear. In one embodiment, neuromodulation comprises neuromodulation of a first peripheral nerve, a processor and a memory for storing instructions that, when executed by the processor cause the device to neuromodulate a first peripheral nerve for a prespecified amount of time and vary one or more parameters over a prespecified range of parameters at a prespecified rate of variation. Parameters, include for example, burst frequency, pulse frequency, pulse width, intensity, and/or on/off cycling. Nonimplantable stimulation via electrodes is provided in several embodiments. Stimulation may also be accomplished via an implantable system or a combination of an implantable element and nonimplantable system. Denervation may also be accomplished in some embodiments.

In some embodiments, the one or more parameters of the first stimulus comprises a first parameter and a second parameter, and wherein the first parameter and the second parameter are varied on different timescales. In some embodiments, the one or more parameters of the first stimulus comprises a first parameter and a second parameter, wherein the first parameter and the second parameter are varied based on adaptive learning, and wherein the adaptive learning employs at least one of kinematic measurements or satisfaction data. In some embodiments, disclosed herein is a method of stimulating one or more peripheral nerves of an arm, hand, wrist, leg, ankle, foot, head, face, neck or ear with a neurostimulation device, comprising: positioning a first peripheral nerve electrode to deliver stimulation to a first peripheral nerve; delivering stimulation to a first peripheral nerve for a prespecified amount of time; and/or varying one or more parameters of the first stimulus over a prespecified range of parameters at a prespecified rate of variation, where the parameters could include burst frequency, pulse frequency, pulse width, intensity, and/or on/off cycling. In some embodiments, the varied parameter is restricted to (e.g., consists essentially of or comprises) burst frequency and the rate of variation is restricted to (e.g., consists essentially of or comprises) 0.001-100 Hz/s and the range is set by: measuring motion of the patient's extremity using the one or more biomechanical sensors to generate motion data; determining tremor frequency from the motion data; and setting the range across a0.1, 0.2, 0.25, 0.3, 0.4, 0.5,1,1.5, 2, 2.5, 3, 3.5, 4, 4.5, 5, 5.5, or 6 Hz or more or less window centered on the measured tremor frequency. In some embodiments, the varied parameter is restricted to (e.g., consists essentially of or comprises) pulse width and the rate of variation is restricted to (e.g., consists essentially of or comprises) 0.01-10,000 microseconds per second, and the range is set by setting pulse width to 300 microseconds, increasing and setting stimulation amplitude to an individual's minimum sensory threshold; increasing pulse width to an individual's maximum level of comfort, recording the pulse width at maximum level of comfort, and setting the minimum range value to 300 microseconds, and the maximum range value to the individual's pulse width at maximum level of comfort. In some embodiments, the varied parameter is restricted to (e.g., consists essentially of or comprises) stimulation amplitude and the rate of variation and the rate of variation is restricted to (e.g., consists essentially of or comprises) 0.001-10 mA/s, and the range is set by: increasing the stimulation amplitude to an individual's minimum sensory threshold, setting the minimum range value to this minimum sensory threshold, increasing the stimulation amplitude to an individual's maximum comfort level, and setting the maximum range value to this maximum comfort level. In some embodiments, the varied parameter is restricted to (e.g., consists essentially of or comprises) stimulation amplitude and the rate of variation and the rate of variation is restricted to (e.g., consists essentially of or comprises) 0.001-10 mA/s, and the range is set by: increasing the stimulation amplitude to an individual's minimum sensory threshold, setting the minimum range value to a value that is 0.1, 0.2, 0.25, 0.3, 0.4, 0.5, 0.6, 0.7, 0.75, 0.8, 0.9, or 1 mA below this minimum sensory threshold, increasing the stimulation amplitude to an individual's maximum comfort level, and setting the maximum range value to this maximum comfort level. In some embodiments, the one or more parameters of the first stimulus comprises a first parameter and a second parameter, and wherein the first parameter and the second parameter are simultaneously varied. In some embodiments, the one or more parameters of the first stimulus comprises a first parameter and a second parameter, and wherein the first parameter and the second parameter are alternately varied. In some embodiments, the one or more parameters of the first stimulus comprises a first parameter and a second parameter, and wherein the first parameter and the second parameter are varied on different timescales. In some embodiments, the one or more parameters of the first stimulus comprises a first parameter and a second parameter, wherein the first parameter and the second parameter are varied based on adaptive learning, and wherein the adaptive learning employs at least one of kinematic measurements or satisfaction data.

FIG. 1A illustrates a block diagram of an example neuromodulation (e.g., neurostimulation) device 100. The device 100 includes multiple hardware components which are capable of or programmed to provide therapy across the skin of the user. As illustrated in FIG. 1A, some of these hardware components may be optional as indicated by dashed blocks. In some instances, the device 100 may only include the hardware components that are required for stimulation therapy. The hardware components are described in more detail below.

The device 100 can include one or more electrodes 102 for providing neurostimulation signals. In some instances, the device 100 is configured for transcutaneous use only and does not include any percutaneous or implantable components. In some embodiments, the electrodes 102 can be dry electrodes 102. In some embodiments, water or gel can be applied to the dry electrode 102 or skin to improve conductance. In some embodiments, the electrodes 102 do not include any hydrogel material, adhesive, or the like.

The device 100 can further include stimulation circuitry 104 for generating signals that are applied through the electrode(s) 102. In certain embodiments, the signals can vary in, for example, frequency, phase, timing, amplitude, on/off cycling, or offsets. The device 100 can also include power electronics 106 for providing power to the hardware components. For example, the power electronics 106 can include a battery.

The device 100 can include one or more hardware processors 108. The hardware processors 108 can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein. In an embodiment, all of the processing discussed herein is performed by the hardware processor(s) 108. The memory 110 can store data specific to patient and processes as discussed below.

In the illustrated figure, the device 100 can include one or more sensors (e.g., inertial measurement unit (IMU)) 112. As shown in the figure, the sensor(s) 112 may be optional. Sensors 112 could include, for example, biomechanical sensors configured to, for example, measure motion, and/or bioelectrical sensors (e.g., EMG, EEG, and/or nerve conduction sensors). Sensors can include, for example, cardiac activity sensors (e.g., ECG, PPG), skin conductance sensors (e.g., galvanic skin response, electrodermal activity), and motion sensors (e.g., accelerometers, gyroscopes). The one or more sensors 112 may include an audio sensor, including but not limited to a microphone, audio transducer, or accelerometer, configured to measure biological processes, such as breathing, talking, or repetitive motion. Sensors, in some embodiments, sense parameters that are used to optimize neurostimulation and facilitate the introduction of variability in stimulation parameter(s) to reduce tolerance and/or habituation to the neurostimulation. As an example, EEG signals, brain activity and/or neuronal activity may be used in this manner. In one embodiment, variation in one or more parameters may be configured/introduced to generate a natural or desired characteristic of brain or neuronal activity over a time period for the treatment of movement, inflammatory, neurological and psychiatric disorders.

In some embodiments, a tremor signal can be calculated based on input from the one or more of the sensors 112. The tremor signal is a representation of the tremulous activity generated in the brain and motor nerves that causes tremulous muscle activation leading to tremor in the hands, head, neck, legs, feet, and vocal cords.

In some embodiments, the sensor (e.g., IMU) 112 can include one or more of a gyroscope, accelerometer, and magnetometer. The sensor 112 can be affixed or integrated with the neuromodulation (e.g., neurostimulation) device 100. In an embodiment, the sensor 112 is an off the shelf component. In addition to its ordinary meaning, the sensor 112 can also include specific components as discussed below. For example, the sensor 112 can include one more sensors capable of collecting motion data. In an embodiment, the sensor 112 includes an accelerometer. In some embodiments, the sensor 112 can include multiple accelerometers to determine motion in multiple axes. Furthermore, the sensor 112 can also include one or more gyroscopes and/or magnetometer in additional embodiments. Since the sensor 112 can be integrated with the neurostimulation device 100, the sensor 112 can generate data from its sensors responsive to motion, movement, or vibration felt by the device 100. Furthermore, when the device 100 with the integrated sensor 112 is worn by a user, the sensor 112 can enable detection of voluntary and/or involuntary motion of the user.

The device 100 can optionally include user interface components, such as a feedback generator 114 and a display 116. The display 116 can provide instructions or information to users relating to calibration or therapy. The display 116 can also provide alerts, such an indication of response to therapy, for example. Alerts may also be provided using the feedback generator 114, which can provide haptic feedback to the user, such as upon initiation or termination of stimulation, for reminder alerts, to alert the user of a troubleshooting condition, to perform a tremor inducing activity to measure tremor motion, among others. Accordingly, the user interface components, such as the feedback generator 114 and the display 116 can provide audio, visual, and haptic feedback to the user. In certain embodiments, the feedback generator 114 and/or display 116 is configured for the user to provide satisfaction data to the device 100.

Furthermore, the device 100 can include communications hardware 118 for wireless or wired communication between the device 100 and an external system, such as the user interface device 150 discussed below. The communications hardware 118 can include an antenna. The communications hardware 118 can also include an Ethernet or data bus interface for wired communications.

While the illustrated figure shows several components of the device 100, some of these components are optional and not required in all embodiments of the device 100. In some embodiments, a system can include a diagnostic device or component that does not include neuromodulation functionality. The diagnostic device could be a companion wearable device connected wirelessly through a connected cloud server, and include, for example, sensors such as cardiac activity, skin conductance, and/or motion sensors as described elsewhere herein.

In some embodiments, the device 100 can also be configured to deliver one, two or more of the following: magnetic, vibrational, mechanical, thermal, ultrasonic, or other forms of stimulation instead of, or in addition to electrical stimulation. Such stimulation can be delivered via one, two, or more electrodes in contact with, or proximate the skin surface of the patient. However, in some embodiments, the device 100 is configured to only deliver electrical stimulation, and is not configured to deliver one or more of magnetic, vibrational, mechanical, thermal, ultrasonic, or other forms of stimulation.

Although several neurostimulation devices 100 are described herein, in some embodiments nerves are modulated non-invasively to achieve neuro-inhibition. Neuro-inhibition can occur in a variety of ways, including but not limited to hyperpolarizing the neurons to inhibit action potentials and/or depleting neuron ion stores to inhibit firing action potentials. This can occur in some embodiments via, for example, anodal or cathodal stimulation, low frequency stimulation (e.g., less than about 5 Hz in some cases), or continuous or intermediate burst stimulation (e.g., theta burst stimulation). In some embodiments, the wearable devices have at least one implantable portion, which may be temporary or more long term. In many embodiments, the devices are entirely wearable and non-implantable.

Figure 1B:
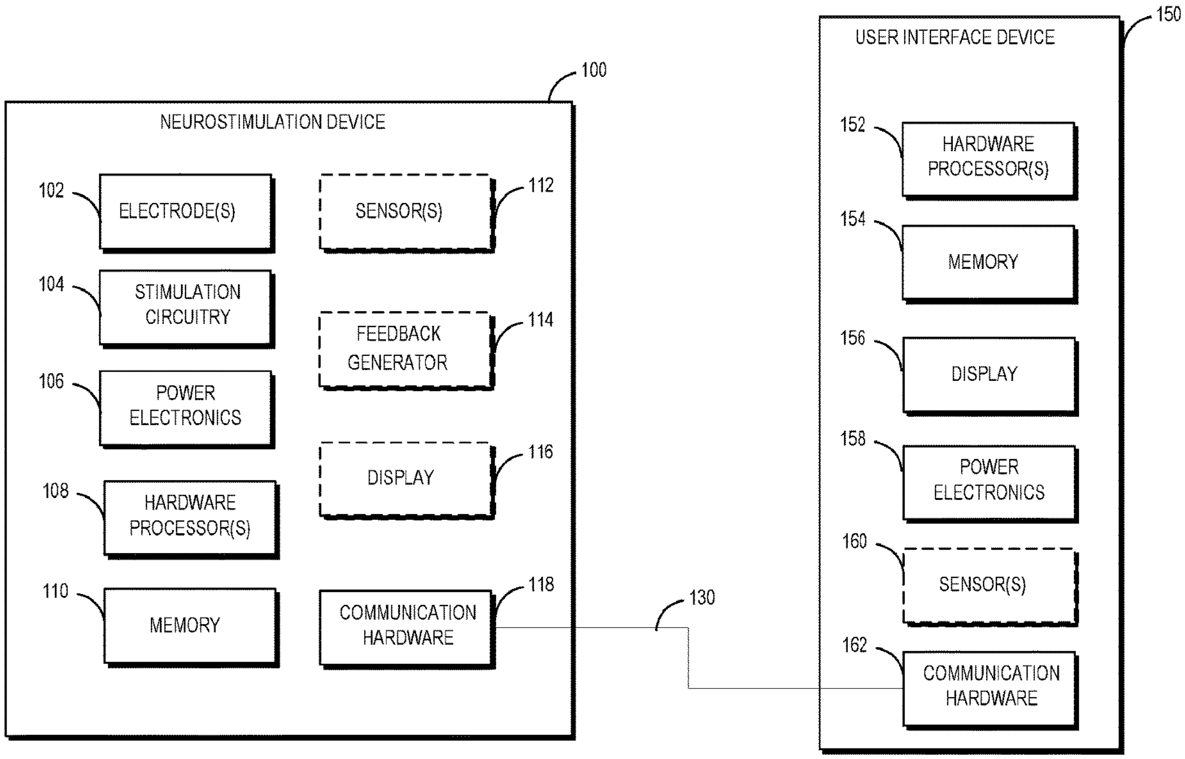
FIG. 1B illustrates communications between the neurostimulation device of FIG. 1A and a user interface device over a communication link.

FIG. 1B illustrates communications between the neurostimulation device 100 and a user interface device 150 over a communication link 130. The communication link 130 can be wired or wireless. The neuromodulation (e.g., neurostimulation) device 100 is capable of communicating and receiving instructions from the user interface device 150 via communication hardware 162. The user interface device 150 can include a computing device. In some embodiments, the user interface device 150 is a mobile computing device, such as a mobile phone, a smartwatch, a tablet, or a wearable computer. The user interface device 150 can also include server computing systems that are remote from the neurostimulation device 100. In certain embodiments, the user interface device 150 can include a hardware processor(s) 152, a memory 154, a display 156, and power electronics 158. In some embodiments, the user interface device 150 can also include one or more sensors 160, such as sensors described elsewhere herein. Furthermore, in some instances, the user interface device 150 can generate an alert responsive to device issues or a response to therapy. The alert may be received from the neurostimulation device 100.

In additional embodiments, data acquired from the one or more sensors 112 is processed by a combination of the hardware processor(s) 108 and hardware processor(s) 152. In further embodiments, data collected from one or more sensors 112 is transmitted to the user interface device 150 with little or no processing performed by the hardware processors 108. In some embodiments, the user interface device 150 can include a remote server that processes data and transmits signals back to the device 100 (e.g., via the cloud).

Figure 2A:
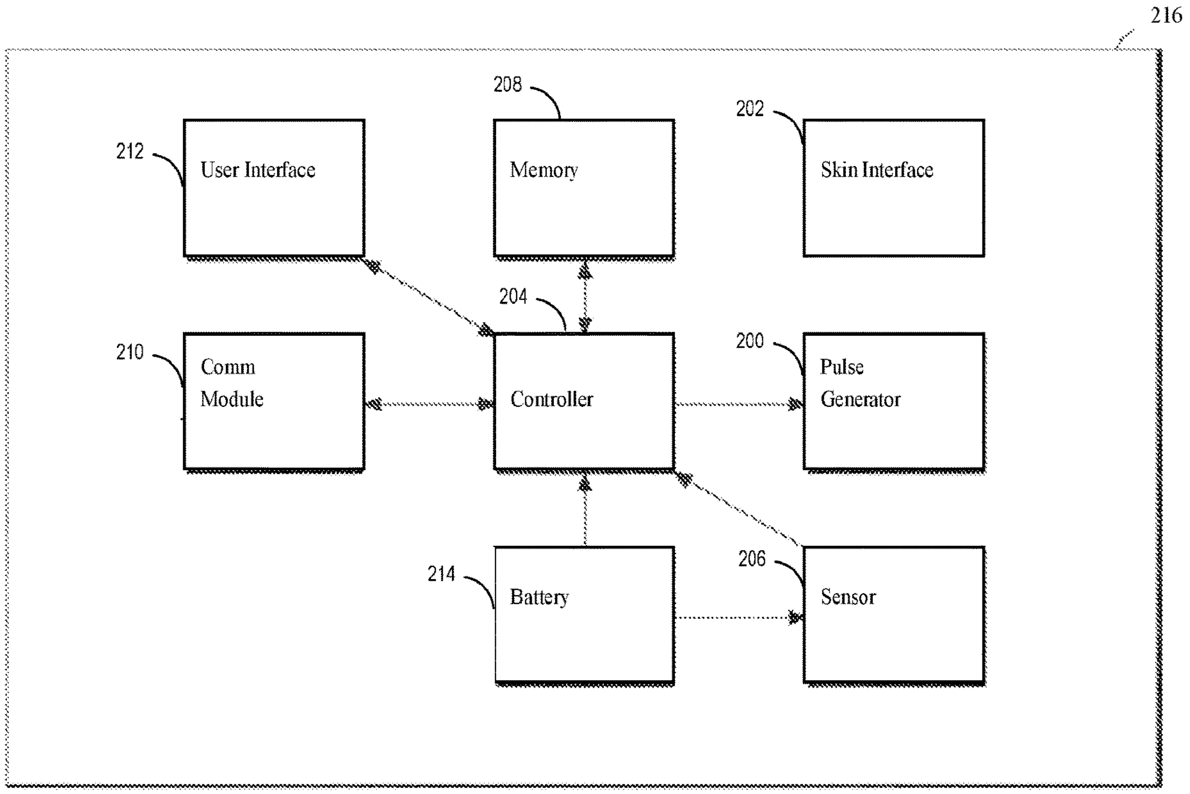
FIG. 2A illustrates a block diagram of an embodiment of a device and system that provides peripheral nerve stimulation and senses a biological or kinematic measure and/or receives user satisfaction data that is used to customize or modify the delivery of an electrical stimulus.

FIG. 2A illustrates a block diagram of an embodiment of a device and system 216 that provides peripheral nerve stimulation. In certain embodiments, the device and system 216 senses a biological measure, a kinematic measure, and/or user satisfaction data. In certain embodiments, the device and system 216 use the biological measure, the kinematic measure, and/or the user satisfaction data to customize or modify the delivery of an electrical stimulus.

In some embodiments, the system 216 comprises a pulse generator 200. In certain embodiments, the pulse generator 200 delivers electrical stimulation to a nerve through one or more skin interfaces 202. In certain embodiments, the one or more skin interfaces 202 can be an electrode 102. In certain embodiments, the one or more skin interfaces 202 sit adjacent to one or more target peripheral nerves. A controller 204 receive one on more signals generated by one or more sensors 206 to control timing and parameters of stimulation. In certain embodiments, the processor 204 uses instructions stored in the memory 208 to coordinate receiving signals from the one or more sensors 206. In certain embodiments, the processor 204 uses the received signal to control stimulation delivered by the pulse generator 200. The memory 208 in the system 216 can store signal data from the sensors 206.

In certain embodiments, the system 216 has a communication module 210 to transmit data to other devices or a remote server via standard wired or wireless communication protocols. In certain embodiments, the system 216 is powered by a battery 214. In certain embodiments, the system 216 has a user interface 212. In certain embodiments, the user interface 212 allows the user to receive feedback from the system 212. In certain embodiments, the user interface 212 allows the user to provide input to the system via, e.g., one or more buttons. In certain embodiments, the user provides satisfaction data via the user interface 212. For example, the user can provide input to the user interface 212 in the form of a patient session impression of improvement (PSII) score and/or a patient satisfaction scope. In certain embodiments, the user interface 212 allows a user to receive instructions, feedback, and control aspects of the delivered stimulation, such as intensity of the stimulation.

In certain embodiments, the controller 204 can receive kinematic and/or satisfaction data to determine a method for varying multiple stimulation parameters based on adaptive learning as disclosed herein. In certain embodiments, the controller 204 causes the device 100 to adjust one or more parameters of a first electrical stimulus based at least in part on the kinematic and/or satisfaction data.

Figure 2B:
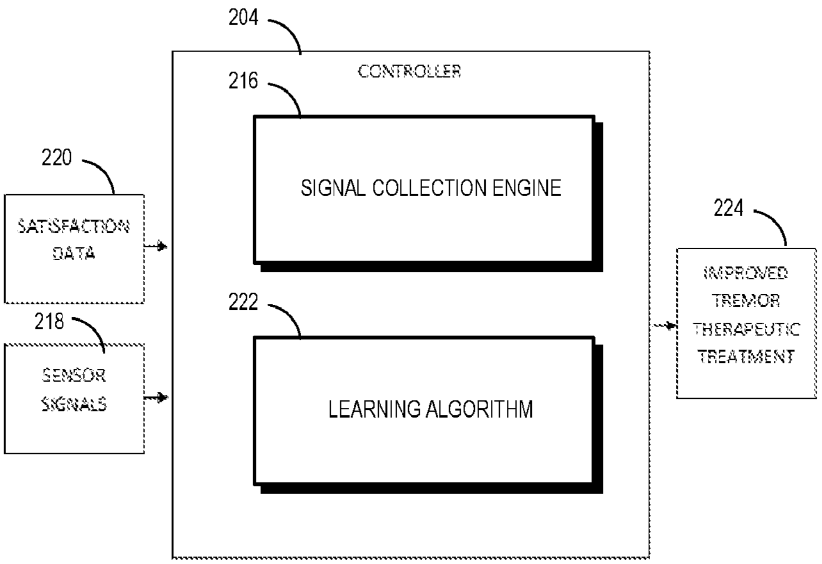
FIG. 2B illustrates a block diagram of an embodiment of a controller that can be implemented with the hardware components described with respect to FIGS. 1A, 1B, and 2A.

FIG. 2B illustrates a block diagram of an embodiment of a controller 204 that can be implemented with the hardware components described with respect to FIGS. 1A, 1B, and 2A. The controller 204 can include multiple engines for performing the processes and functions described herein. The engines can include programmed instructions for performing processes as discussed herein for detection of input conditions, processing data, and control of output conditions. The engines can be executed by the one or more hardware processors of the neuromodulation (e.g., neurostimulation) device 100 alone or in combination with the base station 150, the user interface device 150, and/or the cloud. The programming instructions can be stored in the memory 208. The programming instructions can be implemented in C, C++, JAVA, or any other suitable programming languages. In some embodiments, some or all of the portions of the controller 204 including the engines can be implemented in application specific circuitry such as ASICs and FPGAs. Some aspects of the functionality of the controller 204 can be executed remotely on a server (not shown) over a network. While shown as separate engines, the functionality of the engines as discussed below is not necessarily required to be separated. Accordingly, the controller 204 can be implemented with the hardware components described above with respect to FIGS. 1A, 1B, and 2A.

The controller 204 can include a signal collection engine 216. The signal collection engine 216 can enable acquisition of raw/sensor data 218 from the sensors 112 embedded in the device 100 as well as user satisfaction data 220. The sensor data 218 can include but is not limited to accelerometer or gyroscope data from the IMU. In certain embodiments, the sensor data 218 can include test kinematic data taken during a therapy session. In certain embodiments, the sensor data 218 can include passive kinematic data. Passive kinematic data is data collected at times outside of the therapy session.

In some embodiments, the neuromodulation, e.g., neurostimulation device 100 or the user interface device 150 with sensors can collect kinematic or motion data (test and/or passive data), or data from other sensors, can measure data over a longer period of time, for example 1, 2, 3, 4, 5, 10, 20, 30 weeks, 1, 2, 3, 6, 9, 12 months, or 1, 2, 3, 5, 10 years or more or less, or ranges incorporating any two of the foregoing values, to determine features, or biomarkers, associated with the onset of tremor diseases, such as essential tremor, Parkinson's disease, dystonia, multiple sclerosis, Lyme disease, etc. Biomarkers could include specific changes in one or more features of the data over time, or one or more features crossing a predetermined threshold. In some embodiments, features of tremor inducing tasks have been stored on the neurostimulation device 100 and used to automatically activate sensors when those tremor inducing tasks are being performed, to measure and store data to memory during relevant times.

The devices, systems and methods described herein are used to treat Lyme disease (e.g., its associated symptoms) in some embodiments. The inflammation associated with Lyme disease is reduced in one embodiment (including for example, long term or chronic inflammation and/or flare ups). Resulting neurological conditions are treated in some embodiments, including but not limited to, weakness, numbness, nerve damage, and facial muscle paralysis. In addition to Lyme disease, chronic fatigue syndrome and its associate symptoms, such chronic inflammation, flare ups etc. are treated according to several embodiments. Treatment may be accomplished by, for example, vagal stimulation and/or sympathetic/parasympathetic balance. Systems and methods to reduce habituation and/or tolerance to nerve stimulation (such as vagus nerve stimulation via an earpiece) are provided in several embodiments by, for example, introducing variability in stimulation parameter(s), as described herein.

The satisfaction data 220 can include but is not limited to subjective data provided by the user. The subjective data can relate to pre or post treatment and/or patient activities of daily living (ADL). In certain embodiments, the user inputs a value that reflects a level of satisfaction. The level of satisfaction can be selected from a predetermined range. In certain embodiments, the range is from 1 to 4. Of course, the range can be any range and is not limited to 1 to 4. For example, the user can provide input to the user interface 212 in the form of a patient session impression of improvement (PSII) score and/or a user satisfaction score.

In some embodiments, the signal collection engine 216 can also perform signal preprocessing on the raw data. Signal preprocessing can include noise filtering, smoothing, averaging, and other signal preprocessing techniques to clean the raw data. In some embodiments, portions of the signals can be discarded by the signal collection engine 216. In some embodiments, portions of the signals are associated with a time stamp or other temporal indicator.

In certain embodiments, the controller 204 determines a level of patient therapeutic benefit based on the passive kinematic data from the sensor signals 218 without requiring the user to input a subjective satisfaction level. In certain embodiments, the controller 204 collects sensor signals 218 in the form of kinematic data measured during the therapy session along with satisfaction data 220 input by the user. In this way in certain embodiments, the controller 204 can determine a level of patient therapeutic benefit based on both the passive kinematic data and the patient provided subjective satisfaction level.

The controller 204 can further include a learning algorithm 222. In certain embodiments, the learning algorithm 222 selects from methods for varying parameter(s) employed during therapy session based on adaptive learning to improve tremor therapeutic treatment 224.

In certain embodiments, the learning algorithm 222 can select from a plurality of stimulation parameters (e.g., burst frequency and pulse frequency) to vary one parameter across one or more nerves (e.g., median and/or radial nerve) and/or select multiple stimulation parameters to vary across one or more nerves.

In certain embodiments, the plurality of stimulation parameters accessed by the learning algorithm 222 can be a subset of all of the stimulation parameters and or patterns of applying stimulation parameters. For example, in certain embodiments, the learning algorithm 222 selects the response profile(s) for which a positive outcome is predicted by the learning algorithm 222. In certain embodiments, the learning algorithm 222 modifies the one or more parameters of the selected stimulation parameters based on the individual user to further personalize the stimulation parameters and improve neurostimulation therapy outcomes.

The learning algorithm 222 can automatically determine a correlation between the satisfaction data 220 and/or the sensor signals 218 and neurostimulation therapy outcomes. Outcomes can include, for example, identifying patients who will respond to the therapy (e.g., during an initial trial fitting or calibration process) based on tremor features of kinematic data from the sensor signals 218 (e.g., approximate entropy), predicting stimulation settings for a given patient (based on their tremor features) that will result in the best therapeutic effect (e.g., dose, where parameters of the dose or dosing of treatment include but are not limited to duration of stimulation, frequency and/or amplitude of the stimulation waveform, and time of day stimulation is applied), predicting patient tremor severity at a given point, predicting patient response over time, examining patient medication responsiveness combined with tremor severity over time, predicting response to transcutaneous or percutaneous stimulation, or implantable deep brain stimulation or thalamotomy based off of tremor features and severity over time, and predicting ideal time for a patient to receive transcutaneous or percutaneous stimulation, or deep brain stimulation or thalamotomy based off of tremor features and severity over time, predicting patient reported therapy outcomes or patient reported satisfaction using tremor features assessed kinematic measurements from the device; predicting patient response to undesirable user experience using tremor features assessed from kinematic measurements and patient usage logs from the device where undesirable user experiences can include but are not limited to device malfunctions and adverse events such as skin irritation or burn; predict patient response trends based on tremor severity where trends can be assessed across total number of sessions, within an individual patient, or across a population of patients; predicting or classifying subtypes of tremor to predicting patient response based on kinematic analysis of tremor features; predicting or classifying subtypes of tremor to provide guidance for individually optimized therapy parameters; predicting or classifying subtypes of tremor to optimize the future study design based on subtypes (e.g., selecting specific subtypes of essential tremor for a clinical study with specific design addressing therapy need for the subtype); and predict patient or customer satisfaction (e.g., net promoter score) based on patient response or other kinematic features from measure tremor motion.

In some embodiments, the neuromodulation, e.g., neurostimulation device 100 or the user interface device 150 with sensors 218 can collect kinematic or motion data, or data from other sensors, when a tremor inducing task is being performed. The user can be directly instructed to perform the task, for example via the display 116 on the device 100 or audio. In some embodiments, features of tremor inducing tasks are stored on the device 100 and used to automatically activate sensors to measure and store data to memory during relevant tremor tasks. The period of time for measuring and storing data can be, for example, 1-180 seconds such as 10, 20, 30, 60, 90, 120 seconds, or 1-60 minutes such as 1, 2, 3, 5, 10, 15, 20, 30 minutes, or 1-12 hours such as 1, 2, 3, 4, 5, 6, 7, 8 hours or more or less, or ranges incorporating any two of the foregoing values. Based on a training set of data from a cohort of previous wearers with tremor or another condition, the learning algorithm 222 can detect features that are correlated with response to stimulation such that the patient or physician can be presented with one or more response profiles. The one or more response profiles can correspond to neurostimulation therapy that has a qualitative likelihood for patient response.

In another embodiment, features can be correlated with the type of tremor measured, such as essential tremor, resting tremor (associated with Parkinson's Disease), postural tremor, action tremor, intention tremor, rhythmic tremor (e.g., a single dominant frequency) or mixed tremor (e.g., multiple frequencies). In some embodiments, essential tremor pathology can include, for example, a primarily cerebellar variant with Bergmann gliosis and Purkinje cell torpedoes, and a Lewy body variant, and a dystonic variant, and a multiple sclerosis variant, and a Parkinson disease variant. The type of tremor most likely detected can be presented to the patient or physician as a diagnosis or informative assessment prior to receiving stimulation or to assess appropriateness of prescribing a neuromodulation, e.g., stimulation treatment. In another embodiment, various response profiles may be applied based on the tremor type determined; different profiles could include changes in stimulation parameters, such as frequency, pulse width, amplitude, burst frequency, duration of stimulation, or time of day stimulation is applied. In one embodiment, the user interface device 150 can include an app that asks the patient to take a self-photograph or self-video, which has the patient perform a task that has both posture and intention actions.

In some embodiments, the neuromodulation, e.g., neurostimulation device 100 can apply transcutaneous stimulation to a patient with tremor that is a candidate for implantable deep brain stimulation or thalamotomy. Tremor features and other sensor measurements of tremor severity will be used to assess response over a prespecified usage period, which could be 1 month or 3 months, or 5, 7,14, 30, 60, or 90 days or more or less. The response to transcutaneous stimulation as assessed, for example, by the learning algorithm 222 described herein using sensor measurements from the device and/or patient satisfaction data can advantageously provide an assessment of the patient's likelihood to respond to implantable deep brain stimulation or other implantable or non-implantable therapies.

In some embodiments, the learning algorithm 222 develops rules between the satisfaction data 220 and/or sensor signals 218 and one or more parameters of one or more response profiles that correspond to neurostimulation therapy outcomes. The learning algorithm 222 can employ machine learning modeling along with signal processing techniques to determine rules, where machine learning modeling and signal processing techniques include but are not limited to: supervised and unsupervised algorithms for regression and classification. Specific classes of algorithms include, for example, Artificial Neural Networks (Perceptron, Back-Propagation, Convolutional Neural Networks, Recurrent Neural networks, Long Short-Term Memory Networks, Deep Belief Networks), Bayesian (Naive Bayes, Multinomial Bayes and Bayesian Networks), clustering (k-means, Expectation Maximization and Hierarchical Clustering), ensemble methods (Classification and Regression Tree variants and Boosting), instance-based (k-Nearest Neighbor, Self-Organizing Maps and Support Vector Machines), regularization (Elastic Net, Ridge Regression and Least Absolute Shrinkage Selection Operator), and dimensionality reduction (Principal Component Analysis variants, Multidimensional Scaling, Discriminant Analysis variants and Factor Analysis). In some embodiments, the controller 204 can use the rules developed between features and one or more parameters to automatically determine response profiles that correspond to neurostimulation therapy outcomes. The controller 204 can also use the one or more response profiles to control or change settings of the neurostimulation device, including but not limited to stimulation parameters (e.g., stimulation amplitude, frequency, patterned (e.g., burst stimulation), intervals, time of day, individual session or cumulative on time, and the like).

Accordingly, the one or more response profiles that correspond to neurostimulation therapy can improve operation of the neuromodulation, e.g., neurostimulation device, and advantageously and accurately identify potential candidates for therapy and well as various disease state and therapy parameters over time. The generated one or more response profiles that correspond to neurostimulation therapy can be saved in the memory 110 and/or memory 208. For example, the methods for varying one or more stimulation parameters can be generated and stored prior to operation of the neurostimulation device 100. Accordingly, in some embodiments, the controller 204 can apply the saved one or more profiles based on new data collected by the sensors 112, 206 to determine outcomes or control the neuromodulation, e.g., neurostimulation device 100.

Figure 2C:
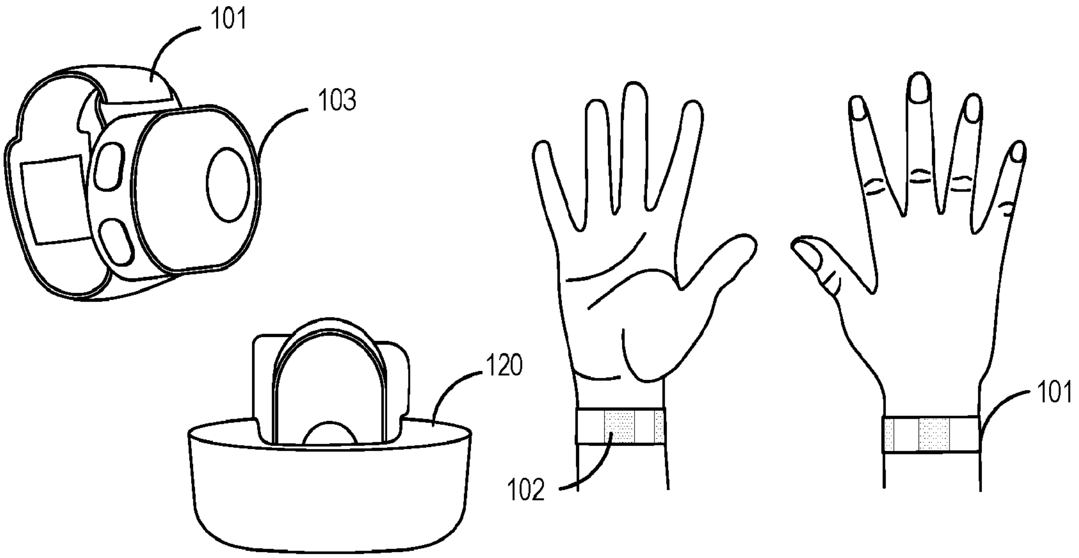
FIG. 2C schematically illustrates an embodiment of a neuromodulation device and base station.

FIG. 2C schematically illustrates an embodiment of a neuromodulation device 100 and base station 120. The neurostimulation device 100 can include a stimulator 103 and detachable band 101 including two or more working electrodes 102 (positioned over the median and radial nerves) and a counter-electrode positioned on the dorsal side of the wrist. The electrodes 102 could be, for example, dry electrodes or hydrogel electrodes. The base station 120 can be configured to stream movement sensor and usage data on a periodic basis, e.g., daily and charge the neurostimulation device 100. The device stimulation bursting frequency can be calibrated to a lateral postural hold task "wing-beating" or forward postural hold task for a predetermined time, e.g., 5-30 seconds (e.g., 20 seconds) for each subject Other non-limiting examples of device parameters can be as disclosed elsewhere herein.

In some embodiments, stimulation may alternate between each nerve such that the nerves are not stimulated simultaneously. In some embodiments, all nerves are stimulated simultaneously. In some embodiments, stimulation is delivered to the various nerves in one of many bursting patterns. The stimulation parameters may include on/off, time duration, intensity, pulse rate, pulse width, waveform shape, and the ramp of pulse on and off. In one embodiment the stimulation may last for approximately 10 minutes to 1 hour, such as approximately 10, 20, 30, 40, 50, or 60 minutes, or ranges including any two of the foregoing values.

In some embodiments, a plurality of electrical stimuli can be delivered offset in time from each other by a predetermined fraction of multiple of a period of a measured rhythmic biological signal such as hand tremor, such as about %, %, or % of the period of the measured signal for example. Further possible stimulation parameters are described, for example, in U.S. Pat. No. 9,452,287 to Rosenbluth et al., U.S. Pat. No. 9,802,041 to Wong et al., PCT Pub. No. WO 2016/201366 to Wong et al., PCT Pub. No. WO 2017/132067 to Wong et al., PCT Pub. No. WO 2017/023864 to Hamner et al., PCT Pub. No. WO 2017/053847 to Hamner et al., PCT Pub. No. WO 2018M09680 to Wong et al., PCT Pub. No. WO 2018/039458 to Rosenbluth et al., and PCT Pub. No. WO 2020/086726 to Hamner et al., each of the foregoing of which are hereby incorporated by reference in their entireties.

In some embodiments, a neuromodulation device can include the ability to track a user's motion data for the purpose of gauging one, two, or more tremor frequencies of a patient. The patient could have a single tremor frequency, or in some cases multiple discrete tremor frequencies that manifest when performing different tasks. Once the tremor frequencies are observed, they can be used as one of many seminal input parameters to a customized neuromodulation therapy. The therapy can be delivered, e.g., transcutaneously, via one, two, three or more nerves (e.g., the median and radial nerves, and/or other nerves disclosed elsewhere herein) in order to reduce or improve a condition of the patient, including but not limited to their tremor burden. In some embodiments, the therapy modulates afferent nerves, but not efferent nerves. In some embodiments, the therapy preferentially modulates afferent nerves. In some embodiments, the therapy does not involve functional electrical stimulation. The tremor frequency can be used to calibrate the patients neuromodulation therapy, being used as a calibration frequency in some embodiments to set one or more parameters of the neuromodulation therapy, e.g., a burst envelope period. In some embodiments, the calibration frequency can be between, for example, about 4 Hz and about 12 Hz, between about 3 Hz and about 6 Hz, or about 3 Hz, 4 Hz, 5 Hz, 6 Hz, 7 Hz, 8 Hz, 9 Hz, 10 Hz, 11 Hz, or 12 Hz, or ranges including any two of the foregoing values.

In some embodiments, stimulation may be applied to two or more nerves in an alternating manner at an interval defined by the tremor frequency (also referred to as burst frequency). In some embodiments, burst frequency is equal to the measured pathological tremor oscillation, which calculated from measured motion, muscle activity, or brain activity.

Various embodiments of the devices and/or systems discussed herein can stimulate nerves in an outer ear of a user, including but not limited to the auricular branch of the vagus nerve, great auricular nerve, auriculotemporal nerve, and/or lesser occipital nerve, among others. In one embodiment, a system can include a neuromodulation device on the wrist or other location of the arm to target a nerve of a subject (e.g., median nerve) and a neuromodulation device (such as any of the auricular devices described herein) in the ear to target the vagus nerve. In some implementations, each neuromodulation device in the system can communicate with each other via a wired or wireless connection. Multiple neuromodulation devices can provide synchronized stimulation to the multiple nerves. Stimulation may be, for example, burst, offset, or alternating between the multiple nerves. Modulation of the vagus nerve can be accomplished with the devices described herein, according to several embodiments. In some embodiments, the devices described herein are used to stimulate the autonomic system. In some embodiments, the devices described herein are used to balance the sympathetic/parasympathetic systems.

Not to be limited by theory, variability of stimulation parameters, including but not limited to jitter or dither-like variability, can enhance the symptomatic and/or long-term reduction of tremor severity provided by the application of alternating stimulation between two or more peripheral nerves. This approach can overcome the challenge of variability observed in people with hand tremor between tremor episodes within an individual, or the variability observed between people in their brain response to peripheral nerve stimulation. Thus, several embodiments include systems and methods to reduce habituation and/or tolerance to stimulation by, for example, introducing variability in stimulation parameter(s).

Adding variation in burst frequency may account for natural variation in pathological tremor frequency. For example, in some cases pathological tremor frequency can change, for example, by more than 2 Hz between tasks and by up to 32% on the same task over time within an individual subject. Calibrating burst frequency to tremor frequency can improve therapeutic effect. However, as discussed above, it may be difficult to target particular tremor frequencies due to the natural variations. In some instances, it may not be suitable to continuously track the changing tremor characteristics using sensors discussed herein. It may consume too many computational resources and may also deplete battery. Therefore, the inventors realized that instead of focusing on a particular value or trying to exactly align to a pathological characteristic, adding variation in stimulation parameters, such as burst frequency, may enhance therapeutic benefit in treatment of conditions. Pathological characteristics can vary depending on the pathological condition. For example, for treatment of tremor, the characteristics of tremor may include tremor frequency, power, phase, amplitude, and the like. For example, for treatment of migraine, a 3 Hz burst frequency with a 150 Hz pulse frequency may override thalamocortical dysrhythrria in individuals. For example, for treatment of stroke, a 1 Hz burst frequency with a 10 Hz pulse frequency may reduce neuronal inhibition in the motor cortex that otherwise inhibits motor activity in individuals. In some instances, the characteristics may include physiological parameters, such as heart rate, respiration rate, heart rate variability, blood pressure, and the like. The characteristics may also correspond to sympathetic and/or parasympathetic activity. Furthermore, the characteristics may correspond to neural oscillations. In some instances, neural oscillations may be observed in alpha, beta, delta, theta, gamma frequency bands. In some embodiments, EEG sensor is not required to probe these oscillations and provide therapeutic effect based on stimulation.

In some instances, variations will increase probability of alignment with the changing pathological characteristics during a portion of the therapy session, over time and across tasks. In some embodiments, one or more stimulation parameters are continuously varied over the course of the stimulation. Furthermore, in some instances, measuring tremor characteristics with one or more sensors is not required to provide a therapeutic effect. In addition to tremor, introduction of variability to treat conditions other than tremor are also provided (e.g., other movement disorders, migraine, stroke, other neurological disorders, etc.).

In additional embodiments, stimulation parameters are agnostic for any particular individual and may be varied within generally known therapeutic ranges during the course of stimulation. Adding variation in pulse frequency may account for individual differences in the brain response to peripheral nerve stimulation. For example, the evoked response generated in the ventral intermediate nucleus of the thalamus by median nerve stimulation was maximized at a pulse frequency of 50 Hz in some subjects and 100 Hz in other subjects. By varying pulse frequency throughout these range of values, the brain response is maximized during some portion of the therapy session for every individual, which may enhance therapeutic benefit. Varying pulse frequency during deep brain stimulation (DBS) therapy improved motor score outcomes, gait speed, and freezing of gait episodes in Parkinson's disease patients, compared to fixed frequency DBS. Finally, varying pulse frequency may produce natural stimulation-evoked sensations.

Adding variation in pulse intensity, current amplitude, voltage amplitude, or pulse width would be expected to change the extent of neuronal recruitment within the targeted nerves, with higher intensities and amplitudes, or longer pulse widths, increasing the extent of recruitment. These variations in nerve recruitment may vary the degree of activation in downstream neuronal sub-populations within the brain, which in turn could enhance therapeutic benefit, potentially by reducing the likelihood of neuronal adaptation or habituation to stimulation. In addition, varying pulse intensity or pulse width may produce more natural stimulation-evoked sensations than fixed stimulation. Systems and methods to reduce habituation and/or tolerance to stimulation are provided in several embodiments by, for example, introducing variability in stimulation parameter(s), as described herein. Habituation and/or tolerance to neurostimulation that occur in the treatment of movement, inflammatory, neurological and psychiatric disorders are treated in several embodiments.

Adding on/off periods in the stimulation waveform may enhance the therapeutic effects by increasing the desired desynchronization effect in downstream neuronal sub-populations within the brain.

Additionally, not to be limited by theory, variability in any of the above parameters can enhance the desired neuronal desynchronization effect that enhances therapeutic benefit (e.g., a lower tremor or symptom severity after application of stimulation).

Variability can be applied to one or more of the following parameters for stimulating a nerve including but not limited to burst frequency or alternating frequency, pulse frequency, pulse width, pulse spacing, intensity, current amplitude, voltage amplitude, duration of stimulation, on/off periods, or amplitude envelope periods. Variability can be applied across multiple stimulation parameters for stimulating a nerve including but not limited to simultaneous variation, braided variation, timescale variation, and adaptive learning. In certain embodiments, adaptive learning is employed in combination with the listed variations as well as other variations to improve neurostimulation therapy outcomes.

FIGS. 3A-B illustrate examples of how stimulation parameters (e.g., burst frequency and pulse frequency) are varied between two or more prespecified values as stimulation is alternated across two nerves (e.g., median and radial nerve). The plots show patterns of current delivered by the device 100 over time.

FIG. 3A illustrates an embodiment of the device 100 that delivers patterned stimulation to the median nerve 302 and radial nerve 304 where burst frequency is varied after a prespecified time period or prespecified number of bursts. As is illustrated in Plot 3A, the burst frequency is initially burst frequency A with a period of $1/f_1$306. The burst frequency subsequently changes to burst frequency B with a different period of $1/f_2$308. Plot 3A is only exemplary and is not intended to limit the variations in burst frequency to the illustrated values or the number of different burst frequencies. Further, while FIG. 3A illustrates the variation occurring across multiple nerves (e.g., median and radial nerves), the disclosure is not so limited. The disclosed variations can be applied to only a single nerve.

In some embodiments, burst frequency variability is centered on an about, at least about, or no more than about 0.1, 0.2, 0.25, 0.3, 0.4, 0.5, 1, 1.5, 2, 2.5, 3, 3.5, 4, 4.5, 5, 5.5, or 6 Hz or more or less window (or ranges including any two of the foregoing values), or any combination thereof, around a calibration frequency measured from a tremor-inducing task, such as a postural hold. In certain embodiments, if the measured tremor frequency is at a lower edge of a partial tremor frequency range (e.g., a 3-12 Hz window), the burst frequency variation window would not go below 3 Hz. In certain embodiments, if the measured tremor frequency is at the higher edge of a partial tremor frequency range (e.g., a 3-12 Hz window), the burst frequency variation window would not go above 12 Hz. In an alternative embodiment, burst frequency variability is applied within the full or partial tremor frequency range, for example between 3-12 Hz for essential tremor. This alternative embodiment may have the advantage of not requiring the user to perform a tremor inducing task for calibration. In yet another embodiment, the range of values for burst frequency variability is set based on the minimum and maximum tremor frequencies measured from multiple tremor-inducing task measurements. Not to be limited by theory, burst frequency variability can avoid exact alignment to the pathological oscillation frequency over time and enhance the therapeutic response compared to a constant burst frequency. In some embodiments, the rate of change of the burst frequency parameter may be between 0.001 Hz/s (i.e., slowest rate of change of burst frequency being in increments of 0.1 Hz every 100 sec) to 100 Hz/s (i.e., fastest rate of change of burst frequency being in increments of 8 Hz burst frequency change every tremor cycle, and rounding up).

FIG. 3B illustrates an embodiment of the device 100 that delivers patterned stimulation to the median nerve 302 and radial nerve 304 where pulse frequency is varied after a prespecified time period or prespecified number of bursts. As is illustrated in FIG. 38, the pulse frequency is initially pulse frequency A with a period of $1/F_1$ 310. The pulse frequency subsequently changes to pulse frequency B with a different period of $1/F_2$312. FIG. 3B is only exemplary and is not intended to limit the variations in pulse frequency to the illustrated values or number of pulse frequencies. Further, while FIG. 3B illustrates the variation occurring across multiple nerves (e.g., median and radial nerves), the disclosure is not so limited. The disclosed variations can be applied to only a single nerve.

Not be limited by theory, the pulse frequency of electrical stimulation applied to a peripheral nerve or neuron can govern how frequently the stimulated nerve or neuron generates an action potential. In some cases, peripheral nerve fibers can be activated to generate an action potential with every stimulation pulse at pulse frequencies of less than approximately 1,000 Hz, if the stimulation pulse width and amplitude are sufficiently high. In some cases, stimulation of the median nerve with pulse frequencies of 5, 50, 100, 150, and 200 Hz can evoke a response of the VIM thalamus, as measured with implanted microelectrodes during a surgical procedure. Moreover, the pulse frequency that generates the maximal amplitude evoked response of the VIM thalamus can vary across subjects. In some embodiments, pulse frequency is varied between 5-200, 5-150, 5-100, 5-50, 50-200, 50-150, 50-100, 100-200, 100-150, or 150-200 Hz (or ranges including any two of the foregoing values), which can enhance therapeutic response compared to a constant pulse frequency. Changes in pulse frequency may be implemented by changing the timing of pulse delivery directly, or by keeping the timing fixed and alternating stimulation amplitude on a pulse-to-pulse basis to change the effective pulse frequency. For example, setting every 1 of 2 pulses to a low stimulation amplitude, which is subthreshold for recruitment of neurons or nerves, can reduce the effective pulse frequency by M. In some embodiments, the rate of change of the pulse frequency parameter may be between 0.001-10,000 Hz/s. Not to be limited by theory, varying pulse frequency may generate activity in the brain that modulates pathological cortical dynamics associated with hand tremor. An additional advantage of varying pulse frequency is that this type of stimulation can elicit a more natural paresthesia sensations, similar to tapping, pressure, touch, and/or vibration sensations experienced during daily life.

In one embodiment the pulse frequency may be from about 1 to about 5000 Hz, about 1 Hz to about 500 Hz, about 5 Hz to about 50 Hz, about 50 Hz to about 300 Hz, or about 150 Hz, or other ranges including any two of the foregoing values. In some embodiments, the pulse frequency may be from 1 kHz to 20 kHz.

FIGS. 4A-B illustrate examples of how stimulation parameters (e.g., amplitude and pulse width) are varied between two or more prespecified values as stimulation is alternated across two nerves (e.g., median and radial nerve).

FIG. 4A illustrates an embodiment of the device 100 that delivers patterned stimulation to the median nerve 302 and radial nerve 304 where current amplitude is varied after a prespecified time period or prespecified number of bursts. As is illustrated in Plot 4A, the current amplitude is initially current amplitude A with a value 402. The current amplitude subsequently changes to current amplitude B with a different value 404. In the illustrated embodiment, the value 404 is greater than the value 402 by an amount 406. FIG. 4A is only exemplary and is not intended to limit the variations in current amplitude to the illustrated values or number of different amplitudes. Further, while FIG. 4A illustrates the variation occurring across multiple nerves (e.g., median and radial nerves), the disclosure is not so limited. The disclosed variations can be applied to only a single nerve.

The intensity of the electrical stimulation may vary from 0 mA to 500 mA, and a current may be approximately 1 to 11 mA in some cases. The electrical stimulation can be adjusted in different patients and with different methods of electrical stimulation. The increment of intensity adjustment may be, for example, 0.1 mA to 1.0 mA.

FIG. 48 illustrates an embodiment of the device 100 that delivers patterned stimulation to the median nerve 302 and radial nerve 304 where pulse width is varied after a prespecified time period or prespecified number of bursts. As is illustrated in FIG. 4B, the pulse width is initially pulse width A with a value 408. The pulse width subsequently changes to pulse width B with a different value 410. As is illustrated by comparison 412, the value 410 is greater than the value 408. Of course, the subsequent value 410 could be less than value 412 in other embodiments. FIG. 48 is only exemplary and is not intended to limit the variations in pulse width to the illustrated values or number of different pulses. Further, while FIG. 4B illustrates the variation occurring across multiple nerves (e.g., median and radial nerves), the disclosure is not so limited. The disclosed variations can be applied to only a single nerve. A pulse width may range from, in some cases, 50 to 500 μs (micro-seconds), such as approximately 300 μs.

Not to be limited by theory, the pulse width of electrical stimulation applied to a peripheral nerve or neuron can be one factor that determines the number and types of nerves or neurons activated with each stimulation pulse. More specifically, varying pulse width applied to a peripheral nerve could advantageously produce a more pronounced desynchronization effect in activated brain region, including but not limited to thalamus, as this can vary the size of the neuronal sub-populations that are recruited during peripheral nerve stimulation. For example, an electrical stimulation pulse train with a fixed pulse width will recruit the same set of neurons, nerves, or nerve fibers with each pulse, which is not a natural characteristic of neuronal activity. In contrast, natural stimuli to the nervous system generate action potentials in a more probabilistic and stochastic fashion. Not to be limited by theory, varying stimulation pulse width over time could be used to activate distinct neuronal populations with each pulse, which could more closely resemble physiological neural signaling. Varying pulse width can produce more natural sensations with stimulation of the median, radial, and ulnar nerves using implanted nerve cuffs in patients with upper limb amputation, and equally or more comfortable sensations with spinal cord stimulation for treatment of neuropathic pain. In some embodiments, pulse width could be varied between sensory threshold and maximum comfortable threshold for an individual, with stimulation amplitude (also referred to as current level or voltage level) held constant. Pulse width of transcutaneously applied electrical stimulation affects comfort and perceived sensation, so ranges can be determined based on feedback of an individual user.

In an alternative embodiment, the pulse width can be varied between a minimum and maximum set for each individual, where the minimum value is, for example, from about, at least about, or no more than about one of 100, 150, 200, 250, 300, or 350 microseconds and the maximum value is set based on an individual's comfort level at a fixed stimulation amplitude, and the rate of variation is restricted to (e.g., consists essentially of or comprises) 0.01-10,000 microseconds per second. In a further embodiment, the fixed stimulation amplitude is based on an individual's sensory level with a fixed pulse width in a range, for example, of between 100-500 microseconds (e.g., 100-250 microseconds, 250-500 microseconds, and overlapping ranges therein).

In alternative embodiments, stimulation amplitude is varied while pulse width is kept constant. Not to be limited by theory, variation of stimulation amplitude (also referred to as current or voltage level, or current or voltage amplitude) can activate distinct neuronal populations with each pulse. In a further embodiment, the range of stimulation amplitude variation is restricted to (e.g., consists essentially of or comprises) a minimum set to the stimulation amplitude at an individual's minimum sensory threshold and a maximum set to the stimulation amplitude at an individual's maximum comfort level. In another embodiment, the minimum is set to a stimulation amplitude at a pre-specified increment below an individual's minimum sensory threshold (sub-sensory) and a maximum set to the stimulation amplitude at an individual's maximum comfort level wherein the pre-specified increment is, for example, about, at least about, or no more than about one of 0.1, 0.2, 0.25, 0.3, 0.4, 0.5, 0.6, 0.7, 0.75, 0.8, 0.9 or 1 mA. In some embodiments, the rate of change of the stimulation amplitude parameter may be between 0.001-10 mA/s.

FIGS. 5A-B illustrate multiple examples of stimulation patterns with prespecified on/off periods as stimulation is alternated across two nerves (e.g., median and radial nerve). The plots show patterns of current delivered by the device 100 over time. FIG. 5A illustrates an embodiment of the device 100 that delivers patterned stimulation to the median and radial nerves where stimulation is delivered for three bursts 502 (i.e., on period) and stimulation is not delivered for two bursts 504 (i.e., off period). In some embodiments, bursts can be defined by the period of the user's measured hand tremor as measured by motion sensors onboard the device 100. In certain embodiments, the period of the user's measured hand tremor corresponds to an initial burst pattern applied by the device 100. In certain embodiments, the device 100 subsequently varies the initial burst as shown in, for example, FIG. 58. FIG. 58 illustrates a similar embodiment where burst frequency is varied between two or more prespecified values across on periods. For example, the device 100 in FIG. 58 delivers patterned stimulation to the median and radial nerves where stimulation is delivered at a burst frequency A having a period of $1/f_1$ 506 (i.e., on period) followed by an off period 510. The device 100 then delivers stimulation at a burst frequency B having a period of $1/f_2$ 508.

Figure 6A:
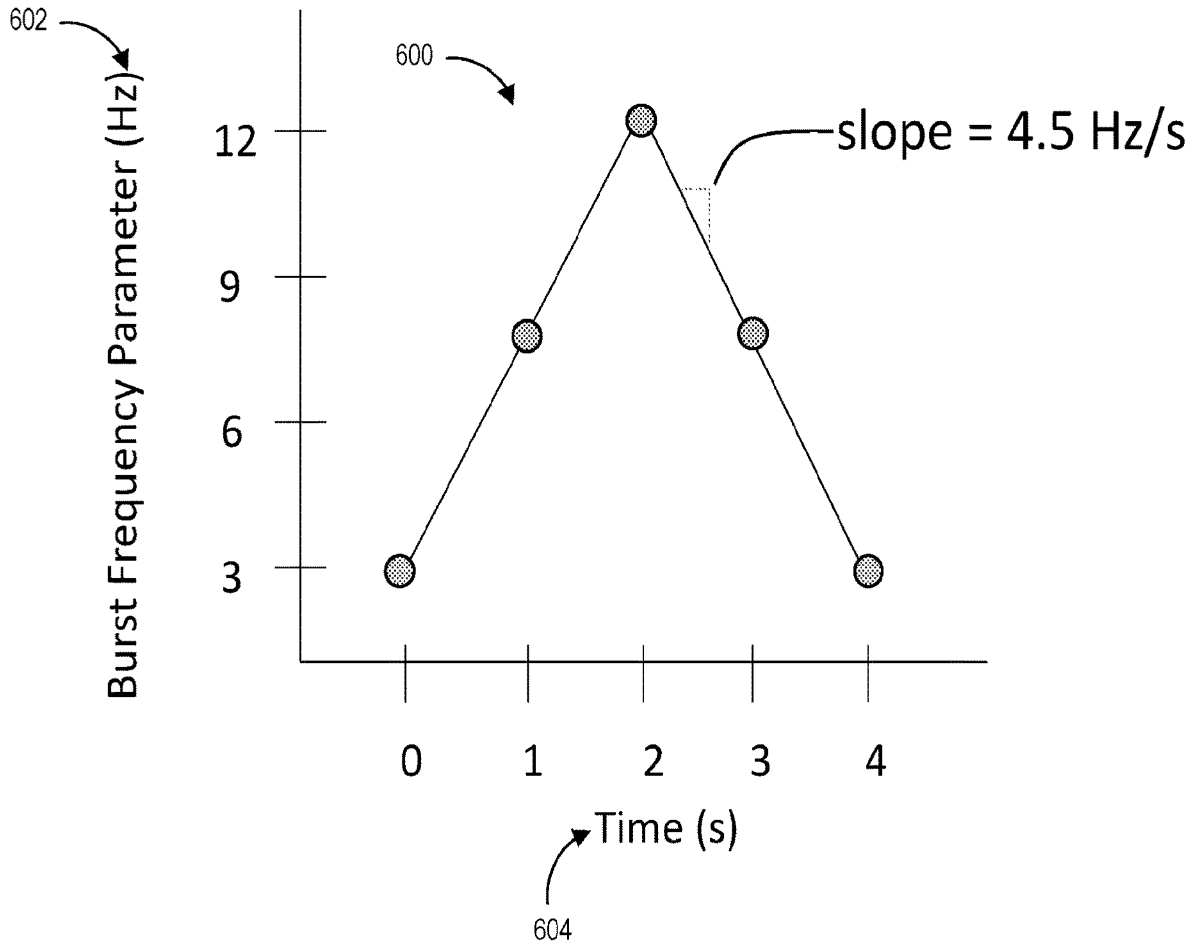
FIG. 6A illustrates an example of a ramping variation of the burst frequency parameter. The burst frequency linearly ramps from 3 Hz to 12 Hz in time period of 2 seconds, which results in a rate of change of 4.5 Hz/s.
Figure 6B:
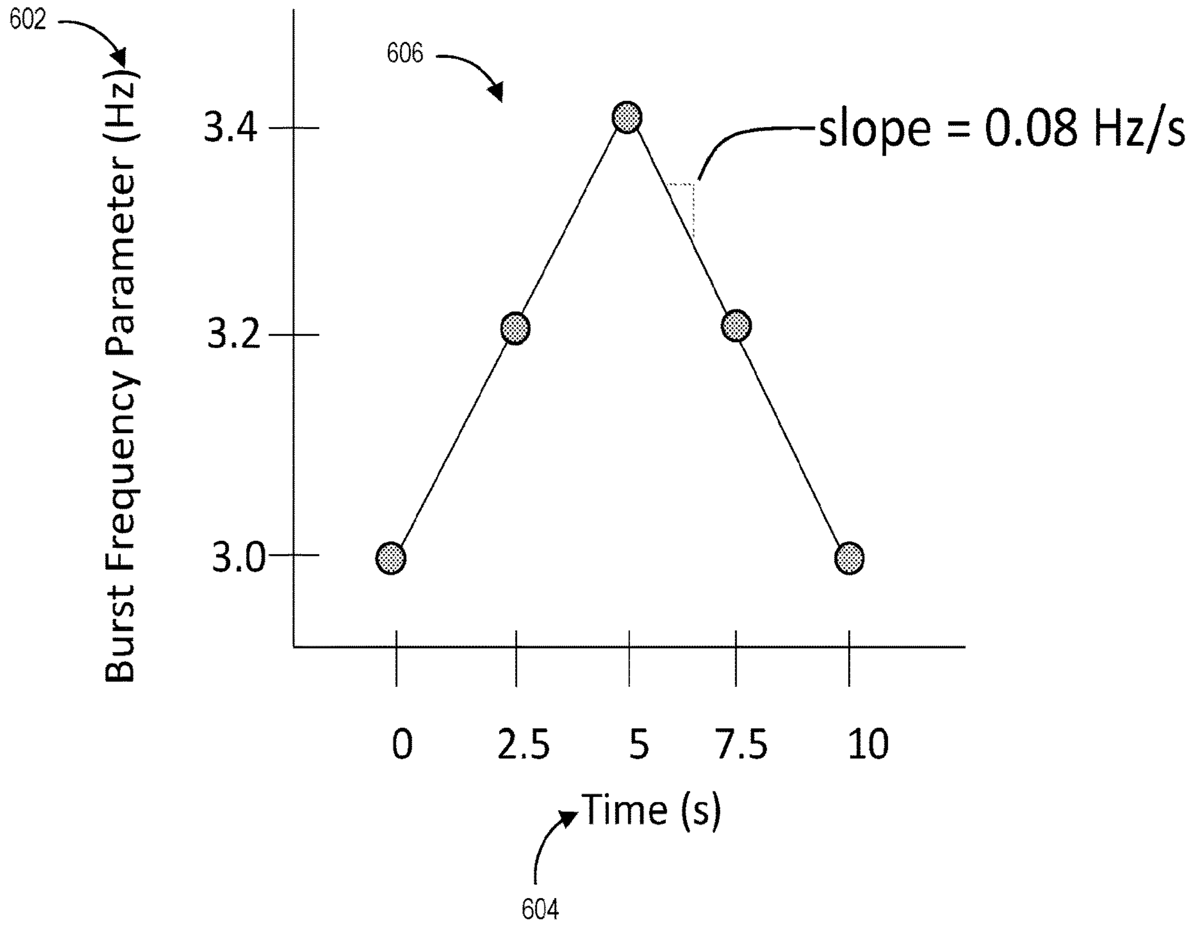
FIG. 6B illustrates an example of a ramping variation of the burst frequency parameter. The burst frequency linearly ramps from 3 Hz to 3.4 Hz in time period of 5 seconds, which results in a rate of change of 0.08 Hz/s.

FIG. 6A illustrates an example of a ramping variation of the burst frequency parameter 602 over time 604. The burst frequency linearly ramps 600 from 3 Hz to 12 Hz in time period of 2 seconds, which results in a rate of change of 4.5 Hz/s. FIG. 6B illustrates another example of a ramping variation of the burst frequency parameter 602 over time 604. The burst frequency linearly ramps 606 from 3 Hz to 3.4 Hz in time period of 5 seconds, which results in a rate of change of 0.08 Hz/s. In some embodiments, one or more stimulation parameters could be varied as stimulation is applied to one or more target nerves or neurons, where stimulation parameters include burst frequency, pulse frequency, pulse width, on/off cycling, and stimulation amplitude. In some embodiments, variation can be performed as a sweep across a prespecified range of parameters (e.g., a linear ramp of values, an example of which is shown in FIGS. 6A and 6B, or sinusoidally-varying values).

In certain embodiments, a randomized or pseudo-randomized variation of parameters can be applied across a prespecified range of parameter values. In a further embodiment, variation of parameters can be distributed based on a predefined probabilistic distribution, including but not limited to a uniform, normal, Gaussian, chi square, binomial, or Poisson distribution. Alternatively, the probabilistic distribution function used to select the values for variation of parameters, such as burst frequency, can be set based on the observed tremor frequency distribution from multiple tremor-inducing task measurements. In some embodiments, there is a prespecified rate of changing parameters, which could theoretically range from changing a parameter value on a prespecified number of stimulation cycles, including but not limited to 1, 2, 3, 4, 5, 6, 7, 8, 9, 10, or more or less tremor cycles, or ranges including any two of the foregoing values (e.g., defined by burst or pulse frequency, non-limiting examples of which are shown in FIG. 3A and FIG. 3B, where the parameter value changes after every 3 stimulation cycles) up to the order of minutes. In some embodiments, this rate of parameter variation is selectable by the end user from a prespecified list of options. In other embodiments, the rate of parameter variation is set by the learning algorithm 222 based on some measured tremor characteristic, such as the rate of change in tremor frequency over time. The change in parameter values may occur instantaneously, or after a period in which stimulation is temporarily turned off for a duration between, for example, approximately 0.1 second and 10 seconds, as illustrated in FIGS. 5A and 58.

Figure 7:
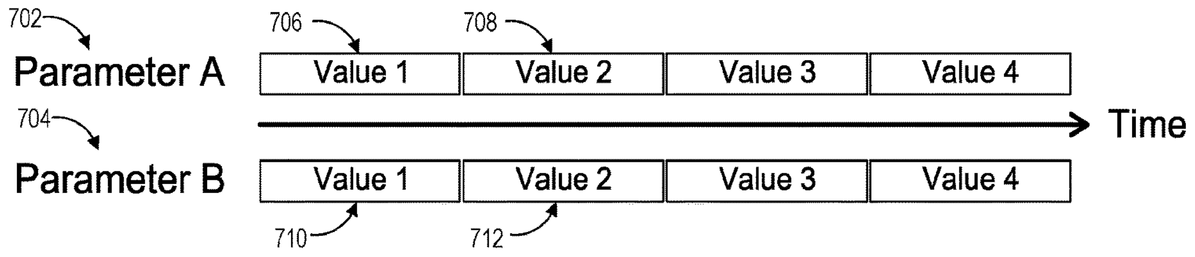
FIG. 7 illustrate an example of how multiple stimulation parameters (e.g., parameters A and B) are simultaneously varied between two or more prespecified values as stimulation is applied to a nerve (e.g., median or radial nerve).

FIG. 7 illustrate an example of how multiple stimulation parameters (e.g., parameters A 702 and B 704) are simultaneously varied between two or more prespecified values as stimulation is applied to a nerve (e.g., median or radial nerve). As is illustrated in FIG. 7, parameter A 702 has a value 1 706 followed by a value 2 708. Parameter B 704 has a value 1 710 followed by a value 2 712. Parameter A 702 and parameter B 704 both change to their respective values 2 simultaneously. The values of parameter A 702 and parameter B 704 both further change to their respective values 3 simultaneously. Of course, the illustrated embodiment and values are only exemplary. In other embodiments, three or more stimulation patterns are simultaneously varied.

In certain embodiments, the method of varying multiple stimulation parameters in FIG. 7 is applied to at least one nerve. In other embodiments, the method for varying stimulation parameters in FIG. 7 is applied to multiple nerves. For example, parameters A 702 and B 704 can be varied for a first nerve (e.g., median nerve) accordingly to the method illustrated in FIG. 7 and for a second nerve (e.g., radial nerve) according to the method illustrated in FIG. 7. Of course, the values of the parameters for the first nerve need not be the same as the values of the parameters for the second nerve.

In certain embodiments, the same parameters (e.g., parameters A and B) are varied across at least two nerves. In other embodiments, the parameters varied across the first nerve according to the method illustrated in FIG. 7 are different from the parameters varied across the second nerve according to the method illustrated in FIG. 7.

In certain embodiments, the method of FIG. 7 can be implemented by alternating stimulation between multiple nerves with a specific burst frequency or used to stimulate a single nerve. In certain embodiments where multiple nerves are stimulated, the stimulation parameters can be varied for stimulation of the first nerve but may be fixed for stimulation of the second nerve.

In certain embodiments, the parameter values 706-712 disclosed in FIG. 7 can change over time. For example, in certain embodiments, the parameter values 706-712 change from therapy session to therapy session. As further explained below in certain embodiments, the parameter values 706-712 can be changed based on the learning algorithm 222 to optimize therapy. In certain embodiments, the parameter values are changed based on pre-session measures, such as tremor kinematic characteristics or system impedance.

Figure 8:
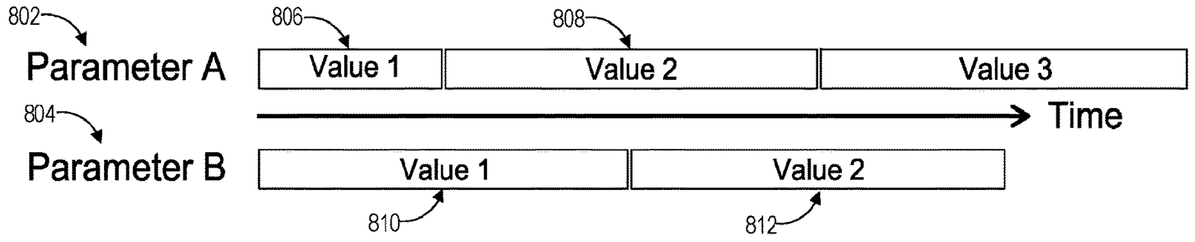
FIG. 8 illustrate an example of how multiple stimulation parameters (e.g., parameters A and B) are varied by alternately changing each parameter between two or more prespecified values as stimulation is applied to a nerve (e.g., median or radial nerve).

FIG. 8 illustrate an example of how multiple stimulation parameters (e.g., parameters A 802 and B 804) are varied by alternately changing each parameter between two or more prespecified values as stimulation is applied to a nerve (e.g., median or radial nerve). As is illustrated in FIG. 8, parameter A 802 has a value 1 806 followed by a value 2 808. Parameter B 804 has a value 1 810 followed by a value 2 812. Parameter A 802 and parameter B 804 alternate changing their respective values. The values of parameter A 802 and parameter B 804 both alternate changing to their respective values 3. In certain embodiment, the values of parameter A 802 and parameter B 804 change asynchronously. Of course, the illustrated embodiment and values are only exemplary. In other embodiments, three or more stimulation patterns are alternately varied.

In certain embodiments, the method of varying multiple stimulation parameters in FIG. 8 is applied to at least one nerve. In other embodiments, the method for varying stimulation parameters in FIG. 8 is applied to multiple nerves. For example, parameters A 802 and B 804 can be varied for a first nerve (e.g., median nerve) accordingly to the method illustrated in FIG. 8 and for a second nerve (e.g., radial nerve) according to the method illustrated in FIG. 8. Of course, the values of the parameters for the first nerve need not be the same as the values of the parameters for the second nerve.

In certain embodiments, the same parameters (e.g., parameters A and B) are varied across at least two nerves. In other embodiments, the parameters varied across the first nerve according to the method illustrated in FIG. 8 are different from the parameters varied across the second nerve according to the method illustrated in FIG. 8.

In certain embodiments, the method of FIG. 8 can be implemented by alternating stimulation between multiple nerves with a specific burst frequency or used to stimulate a single nerve. In certain embodiments where multiple nerves are stimulated, the stimulation parameters can be varied for stimulation of the first nerve but may be fixed for stimulation of the second nerve.

In certain embodiments, the parameter values 806-812 disclosed in FIG. 8 can change over time. For example, in certain embodiments, the parameter values 806-812 change from therapy session to therapy session. As further explained below in certain embodiments, the parameter values 806-812 can be changed based on the learning algorithm 222 to optimize therapy. In certain embodiments, the parameter values are changed based on pre-session measures, such as tremor kinematic characteristics or system impedance.

Figure 9:
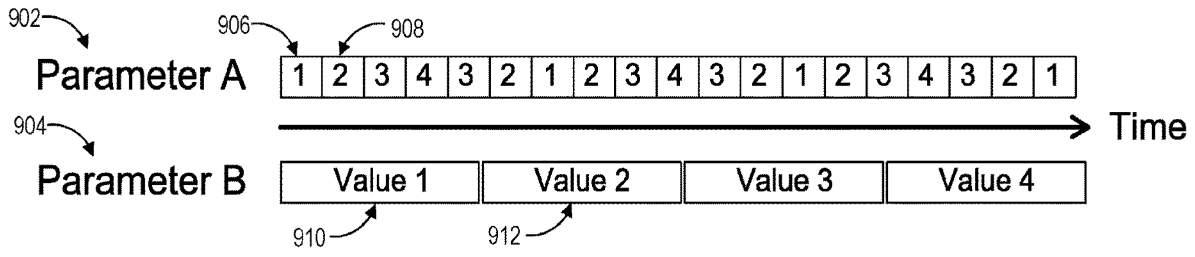
FIG. 9 illustrate an example of how multiple stimulation parameters (e.g., parameters A and B) are varied by applying different timescales to each parameter as stimulation is applied to a nerve (e.g., median or radial nerve).

FIG. 9 illustrate an example of how multiple stimulation parameters (e.g., parameters A and B) are varied by applying different timescales to each parameter as stimulation is applied to a nerve (e.g., median or radial nerve). As is illustrated in FIG. 9, parameter A 902 has a value 1 906 followed by a value 2 908. Parameter B 904 has a value 1 910 followed by a value 2 912. Parameter A 902 and parameter B 904 change their respective values based on different timescales. The values of parameter A 902 and parameter B 904 both change based on their respective timescale. Of course, the illustrated embodiment and values are only exemplary. In other embodiments, three or more stimulation patterns are alternately varied.

In certain embodiments, parameter A 902 (e.g., stimulation amplitude, pulse width) and parameter B 904 (e.g., burst frequency, pulse frequency) are varied on different timescales. For example, in certain embodiments, parameter A 902 may be varied pulse-to-pulse (every few tens of milliseconds or hundreds of milliseconds), whereas parameter B 904 may be varied on a time scale of seconds to minutes.

In certain embodiments, the method of varying multiple stimulation parameters in FIG. 9 is applied to at least one nerve. In other embodiments, the method for varying stimulation parameters in FIG. 9 is applied to multiple nerves. For example, parameters A 902 and B 904 can be varied for a first nerve (e.g., median nerve) accordingly to the method illustrated in FIG. 9 and for a second nerve (e.g., radial nerve) according to the method illustrated in FIG. 9. Of course, the values of the parameters for the first nerve need not be the same as the values of the parameters for the second nerve.

In certain embodiments, the same parameters (e.g., parameters A and B) are varied across at least two nerves. In other embodiments, the parameters varied across the first nerve according to the method illustrated in FIG. 9 are different from the parameters varied across the second nerve according to the method illustrated in FIG. 9.

In certain embodiments, the method of FIG. 9 can be implemented with different timescales for multiple nerves with a specific burst frequency or used to stimulate a single nerve. In certain embodiments where multiple nerves are stimulated, the stimulation parameters can be varied for stimulation of the first nerve but may be fixed for stimulation of the second nerve.

In certain embodiments, the parameter values 906-912 disclosed in FIG. 9 can change over time. For example, in certain embodiments, the parameter values 906-912 change from therapy session to therapy session. As further explained below in certain embodiments, the parameter values 906-912 can be changed based on the learning algorithm 222 to optimize therapy. In certain embodiments, the parameter values are changed based on pre-session measures, such as tremor kinematic characteristics or system impedance.

In certain embodiments, different methods (e.g., methods disclosed in FIGS. 7-9) for varying multiple parameters can be used for different therapy session or during the same therapy session. For example, in certain embodiments, simultaneous variation of parameters as disclosed in FIG. 7 can be used for a first time frame (e.g., 5 minutes) of the therapy session, followed by a braided variation (FIG. 8) for a second time frame (e.g., next 5 minutes) of the therapy session. In certain embodiments, the values or first set of parameters varied during a first time frame are followed by a second set of parameters which are varied during a second time frame.

In certain embodiments, adaptive learning via the learning algorithm 222 is employed in combination with any of the methods illustrated in FIG. 7-9. In certain embodiments, the learning algorithm 222 uses active and/or passive kinematic measurements during or after stimulation sessions to assess how stimulation parameter changes impact real-time therapeutic outcomes (e.g., tremor improvements). For example, if specific parameter values produce greater therapeutic outcomes than other values, then the stimulation method is modified during the same session to only use the corresponding parameter values.

In certain embodiments, the learning algorithm 222 uses satisfaction data during or after stimulation sessions to assess how stimulation parameter changes impact real-time therapeutic outcomes (e.g., tremor improvements). For example, if specific parameter values produce greater therapeutic outcomes than other values, then the stimulation method is modified during the same session to only use the corresponding parameter values.

Figure 10:
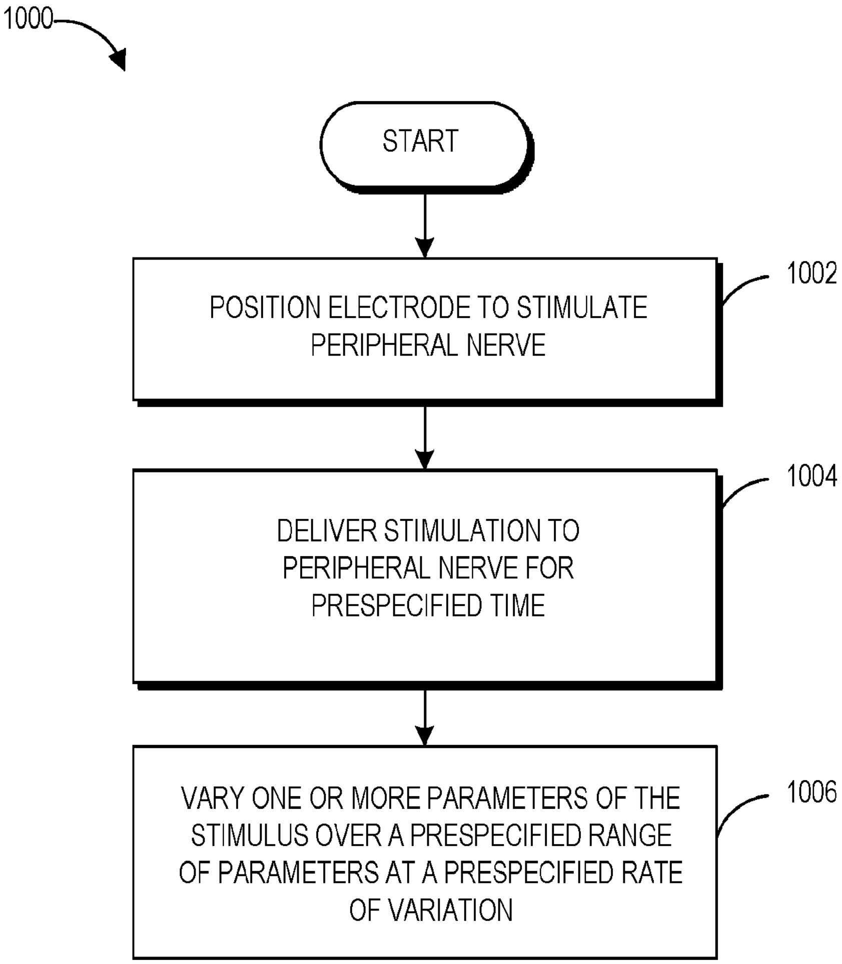
FIG. 10 illustrates a flow chart of an embodiment of a process for varying one or more parameters of a stimulus over a prespecified range of parameters at a prespecified rate of variation.

FIG. 10 illustrates a flow chart of an embodiment of a process 1000 for varying one or more parameters of a stimulus over a prespecified range of parameters at a prespecified rate of variation. The process 100 can be implemented by any of the systems discussed above. The process 100 can be implemented alone or in combination with other processes described herein.

In several embodiments, the process 1000 can begin at block 1002 where the electrode 102 is positioned to stimulate a peripheral nerve. In some instances, the electrode 102 is a component of the device 100. The method moves to block 1004 where the device 100 delivers stimulation to the peripheral nerve for a prespecified time. The method then moves to block 1006 where one or more parameters of the stimulus are varied over a prespecified range of parameter values. In certain embodiments, the one or more parameters are further varied over a prespecified rate of variation.

Variability can be applied to one or more of the following parameters for stimulating a nerve including but not limited to burst frequency or alternating frequency, pulse frequency, pulse width, pulse spacing, intensity, current amplitude, voltage amplitude, duration of stimulation, on/off periods, or amplitude envelope periods. Variability can be applied across multiple stimulation parameters for stimulating a nerve including but not limited to simultaneous variation, braided variation, timescale variation, and adaptive learning. In certain embodiments, adaptive learning is employed in combination with the listed variations as well as other variations to improve outcomes.

Figure 11:
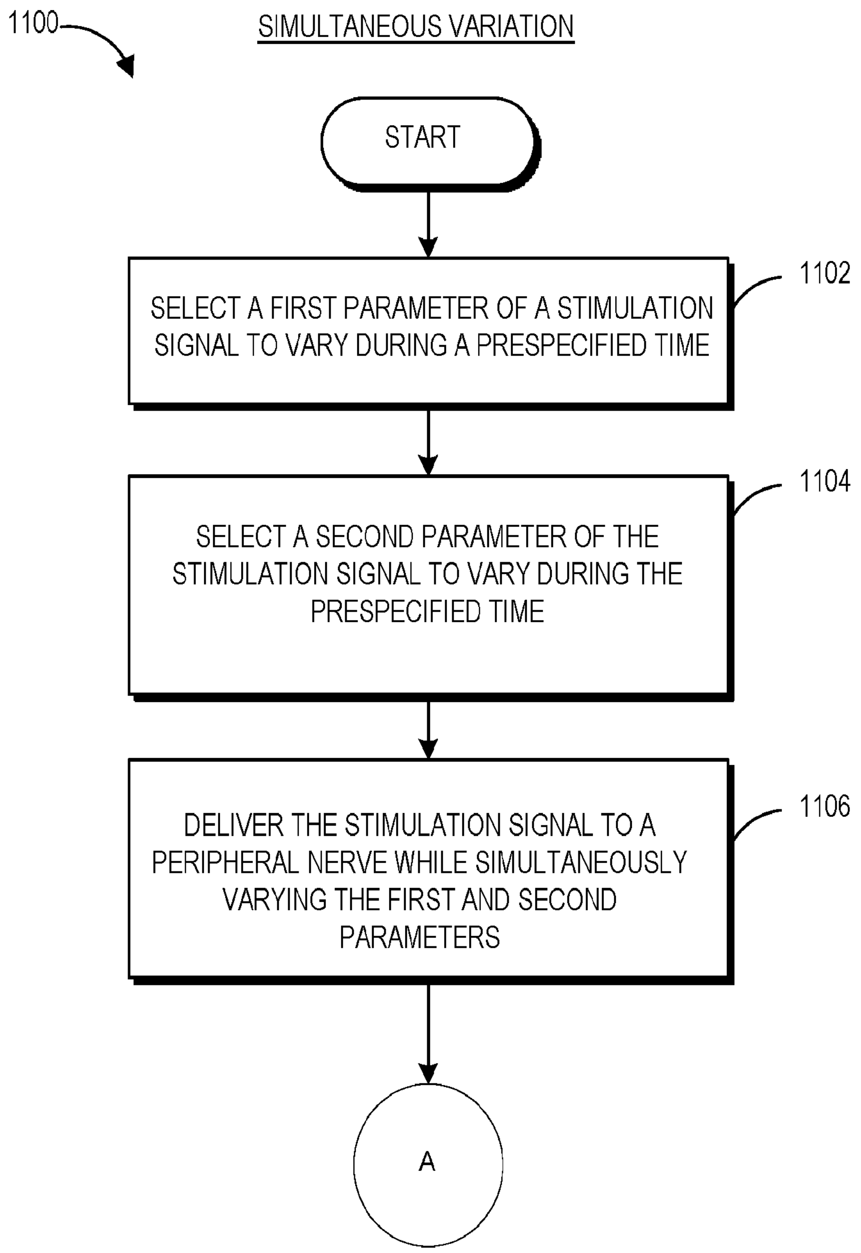
FIG. 11 illustrates a flow chart of an embodiment of a process for simultaneously varying multiple stimulation parameters (e.g., parameters A and B) between two or more prespecified values as stimulation is applied to a nerve (e.g., median or radial nerve).

FIG. 11 illustrates a flow chart of an embodiment of a process 1100 for simultaneously varying multiple stimulation parameters (e.g., parameters A and B) between two or more prespecified values as stimulation is applied to a nerve (e.g., median or radial nerve). The process 1100 can be implemented by any of the systems discussed above. The process 1100 can be implemented alone or in combination with other processes described below.

The process 1100 can begin at block 1102 with selecting a first parameter of a stimulation signal to vary during a prespecified time. Variability can be applied to one or more of the following parameters for stimulating a nerve including but not limited to burst frequency or alternating frequency, pulse frequency, pulse width, pulse spacing, intensity, current amplitude, voltage amplitude, duration of stimulation, on/off periods, or amplitude envelope periods. At block 1104, the method selects a second parameter of the stimulation signal to vary during a prespecified time.

The process moves to block 1106 where the stimulation signal is delivered while simultaneously varying the first and second parameters. The process 1100 can be applied to one or more nerves. For example, parameters A and B can be varied for a first nerve (e.g., median nerve) and for a second nerve (e.g., radial nerve). Of course, the values of the parameters for the first nerve need not be the same as the values of the parameters for the second nerve.

In certain embodiments, the same parameters (e.g., parameters A and B) are varied across at least two nerves. In other embodiments, the parameters varied across the first nerve are different from the parameters varied across the second nerve. In certain embodiments, the process 1100 can be implemented by alternating stimulation between multiple nerves with a specific burst frequency or used to stimulate a single nerve. In certain embodiments where multiple nerves are stimulated, the stimulation parameters can be varied for stimulation of the first nerve but may be fixed for stimulation of the second nerve.

Figure 12:
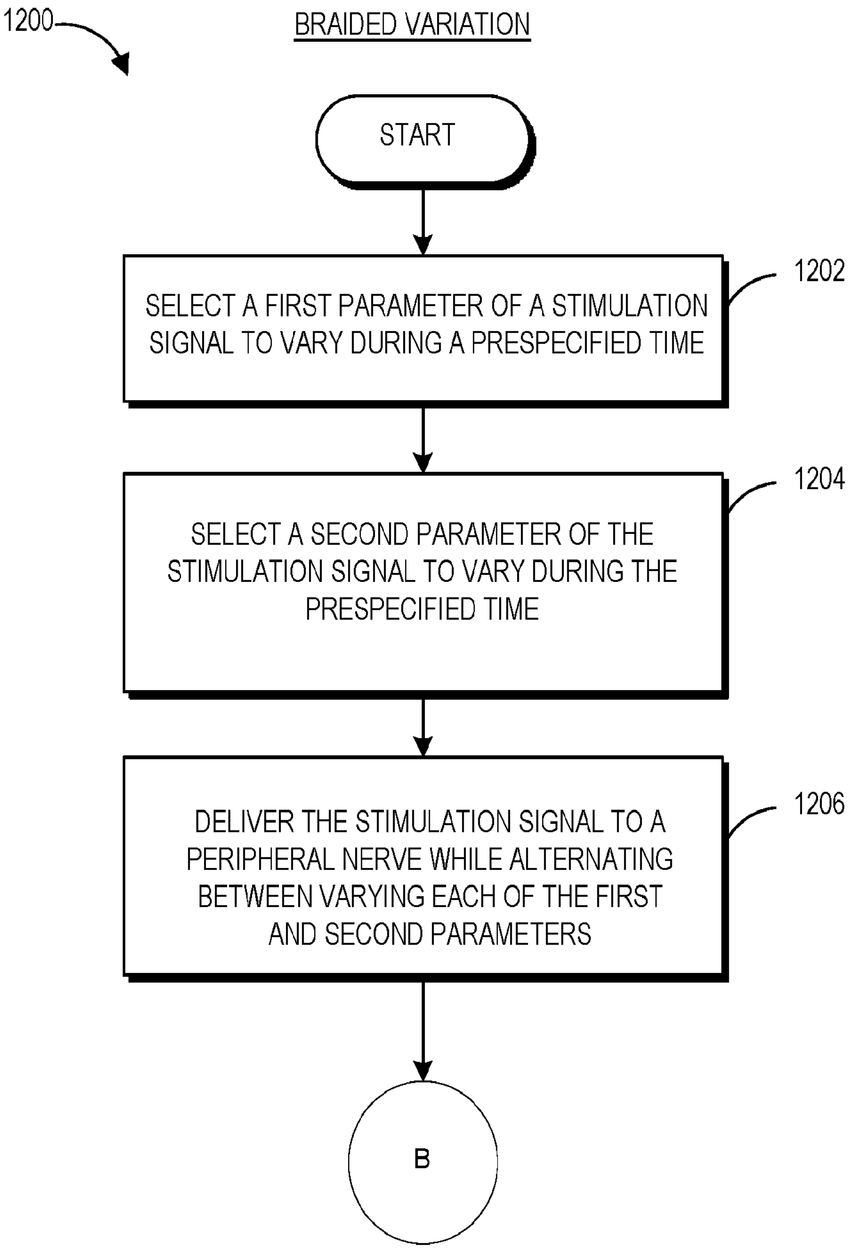
FIG. 12 illustrates a flow chart of an embodiment of a process for alternately varying multiple stimulation parameters (e.g., parameters A and B) between two or more prespecified values as stimulation is applied to a nerve (e.g., median or radial nerve).

FIG. 12 illustrates a flow chart of an embodiment of a process 1200 for alternately varying multiple stimulation parameters (e.g., parameters A and B) between two or more prespecified values as stimulation is applied to a nerve (e.g., median or radial nerve). The process 1200 can be implemented by any of the systems discussed above. The process 1200 can be implemented alone or in combination with other processes described below.

The process 1200 can begin at block 1202 with selecting a first parameter of a stimulation signal to vary during a prespecified time. Variability can be applied to one or more of the following parameters for stimulating a nerve including but not limited to burst frequency or alternating frequency, pulse frequency, pulse width, pulse spacing, intensity, current amplitude, voltage amplitude, duration of stimulation, on/off periods, or amplitude envelope periods. At block 1204, the method selects a second parameter of the stimulation signal to vary during a prespecified time.

The process moves to block 1206 where the stimulation signal is delivered while alternating between varying each of the first and second parameters. The process 1200 can be applied to one or more nerves. For example, parameters A and B can be varied for a first nerve (e.g., median nerve) and for a second nerve (e.g., radial nerve). Of course, the values of the parameters for the first nerve need not be the same as the values of the parameters for the second nerve.

In certain embodiments, the same parameters (e.g., parameters A and B) are varied across at least two nerves. In other embodiments, the parameters varied across the first nerve are different from the parameters varied across the second nerve. In certain embodiments, the process 1200 can be implemented by alternating stimulation between multiple nerves with a specific burst frequency or used to stimulate a single nerve. In certain embodiments where multiple nerves are stimulated, the stimulation parameters can be varied for stimulation of the first nerve but may be fixed for stimulation of the second nerve.

Figure 13:
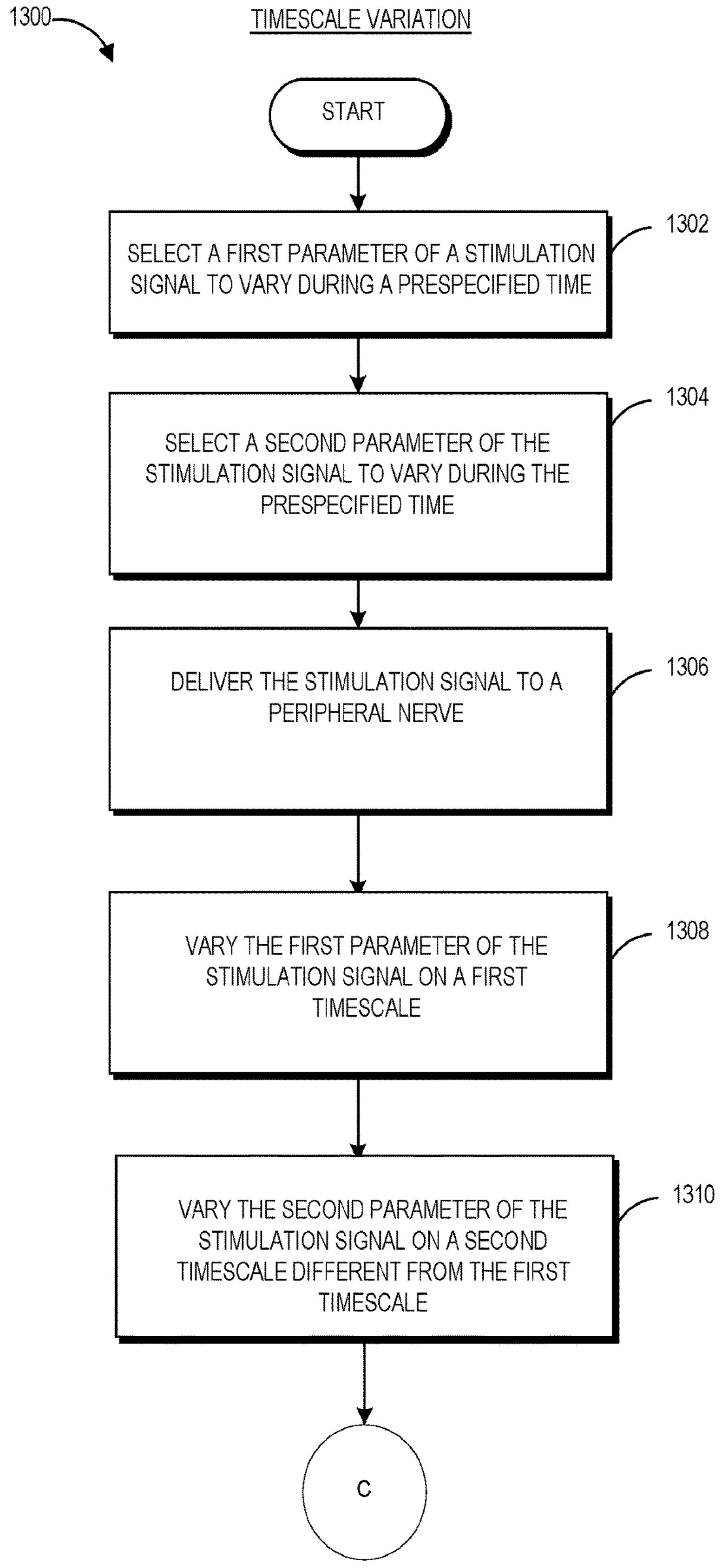
FIG. 13 illustrates a flow chart of an embodiment of a process for varying multiple stimulation parameters (e.g., parameters A and B) between two or more prespecified values by applying different timescales to each parameter as stimulation is applied to a nerve (e.g., median or radial nerve).

FIG. 13 illustrates a flow chart of an embodiment of a process for varying multiple stimulation parameters (e.g., parameters A and B) between two or more prespecified values by applying different timescales to each parameter as stimulation is applied to a nerve (e.g., median or radial nerve). The process 1300 can be implemented by any of the systems discussed above. The process 1300 can be implemented alone or in combination with other processes described below.

The process 1300 can begin at block 1302 with selecting a first parameter of a stimulation signal to vary during a prespecified time. Variability can be applied to one or more of the following parameters for stimulating a nerve including but not limited to burst frequency or alternating frequency, pulse frequency, pulse width, pulse spacing, intensity, current amplitude, voltage amplitude, duration of stimulation, on/off periods, or amplitude envelope periods. At block 1304, the method selects a second parameter of the stimulation signal to vary during a prespecified time.

The process moves to block 1306 where the stimulation signal is delivered to a peripheral nerve. While the stimulation signal is being delivered, the first parameter of the stimulation signal is varied on a first timescale at block 1308 and the second parameter of the stimulation signal is varied on a second timescale at block 1310. The process 1100 can be applied to one or more nerves. In this way, in certain embodiments, blocks 1306,1308, and 1310 are performed concurrently.

In certain embodiments, parameters A and B can be varied for a first nerve (e.g., median nerve) and for a second nerve (e.g., radial nerve). Of course, the values of the parameters for the first nerve need not be the same as the values of the parameters for the second nerve.

In certain embodiments, the same parameters (e.g., parameters A and B) are varied across at least two nerves. In other embodiments, the parameters varied across the first nerve are different from the parameters varied across the second nerve. In certain embodiments, the process 1300 can be implemented by alternating stimulation between multiple nerves with a specific burst frequency or used to stimulate a single nerve. In certain embodiments where multiple nerves are stimulated, the stimulation parameters can be varied for stimulation of the first nerve but may be fixed for stimulation of the second nerve.

Figure 14:
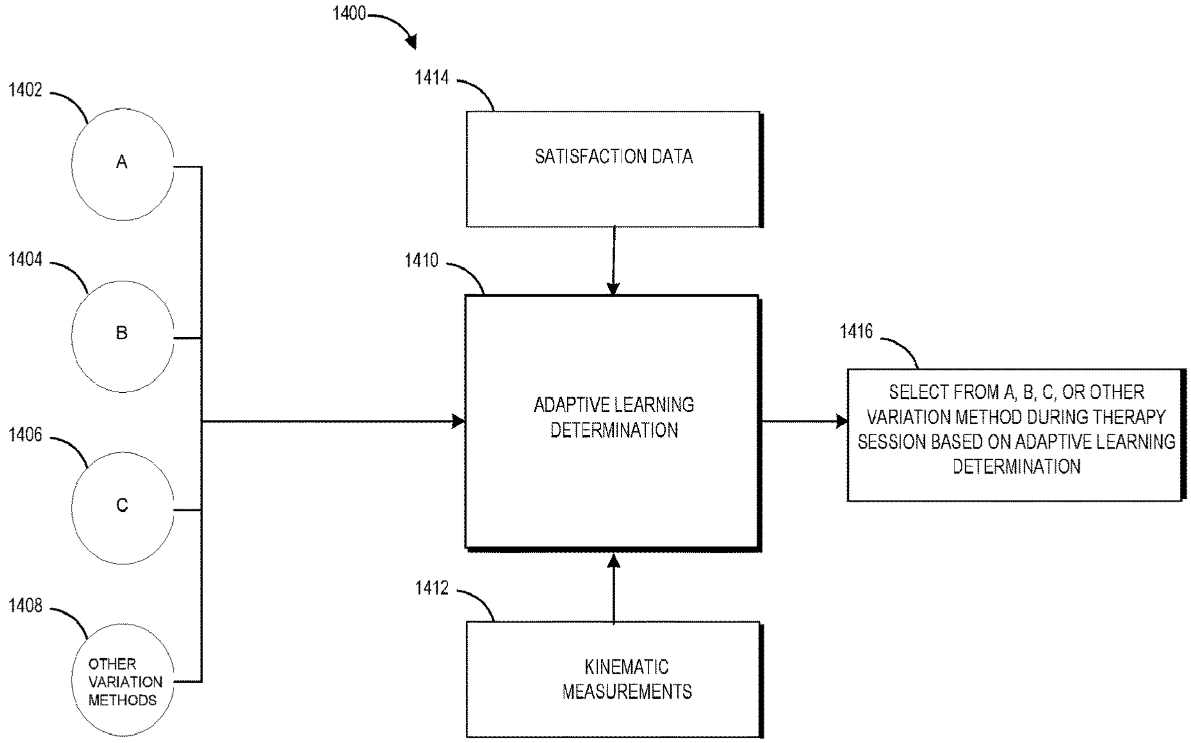
FIG. 14 illustrates an architecture for determining a method that varies multiple stimulation parameters based on adaptive learning.

FIG. 14 illustrates an architecture 1400 for determining a method that varies multiple stimulation parameters based on adaptive learning. The architecture 1400 illustrated in FIG. 14 can be employed in combination with one or more of the processes 1100-1300 discussed above. In certain embodiments, the processes 1100-1300 correspond to blocks 1402, 1404,1406 in FIG. 14, respectively. In certain embodiments, block 1408 can correspond to a method for varying stimulation patterns across a nerve that is not the same as the methods corresponding to blocks 1402,1404,1406. For example, the method associated with block 1408 can begin as one of the methods associated with blocks 1402-1406 but was subsequently adjusted or modified based on blocks 1412 and/or 1414.

The architecture 1400 further includes block 1410 where adaptive learning is employed to select a process from the processes 1402-1408 for use during a therapy session at block 1416. In certain embodiments, the adaptive learning determination 1410 is performed by the learning algorithm 222. The learning algorithm 222 can include programmed instructions for performing processes as discussed herein for detection of input conditions, processing data, and control of output conditions. The learning algorithm 222 can be executed by the one or more hardware processors of the neuromodulation (e.g., neurostimulation) device 100 alone or in combination with the base station 150, the user interface device 150, and/or the cloud 122.

At block 1410, the adaptive learning determination can leverage kinematic measurements 1412 as well as satisfaction data 1414. The kinematic measurements 1412 can include but is not limited to accelerometer or gyroscope data from the sensors 112 (e.g., IMU). In certain embodiments, the kinematic measurements 1412 can include test kinematic data taken during a therapy session. In certain embodiments, the kinematic measurements 1412 can include passive kinematic data. Passive kinematic data is data collected at times outside of the therapy session.

In some embodiments, the neuromodulation, e.g., neurostimulation device 100 or the user interface device 150 with sensors can collect kinematic measurements 1412 (test and/or passive data), or data from other sensors, can measure data over a longer period of time, for example 1, 2, 3, 4, 5, 10, 20, 30 weeks, 1, 2, 3, 6, 9, 12 months, or 1, 2, 3, 5.10 years or more or less, or ranges incorporating any two of the foregoing values, to determine features, or biomarkers, associated with the onset of tremor diseases, such as essential tremor, Parkinson's disease, dystonia, multiple sclerosis, Lyme disease, etc. Biomarkers could include specific changes in one or more features of the data over time, or one or more features crossing a predetermined threshold. In some embodiments, features of tremor inducing tasks have been stored on the neurostimulation device 100 and used to automatically activate sensors when those tremor inducing tasks are being performed, to measure and store data to memory during relevant times.

The devices, systems and methods described above and in the claims are used, in several embodiments to treat depression (including but not limited to post-partum depression, depression affiliated with neurological diseases, major depression, seasonal affective disorder, depressive disorders, etc.). Inflammation is also treated in some embodiments, including but not limited to inflammatory gastrointestinal disorders and skin disorders. In one embodiment, Lyme disease and chronic fatigue syndrome are treated (including chronic inflammatory states and symptoms). Neurological diseases (such as Parkinson's and Alzheimer's) as well their associated symptoms and manifestations are treated in several embodiments (such as depression, tremor, movement disorders, stroke etc.). In some embodiments, rheumatoid arthritis, multiple sclerosis, psoriatic arthritis, osteoarthritis, and psoriasis are treated. Cardiac conditions (such as atrial fibrillation) may also be treated via neuromodulation, as described in several embodiments herein. Headache disorders, such as migraine, are treated in other embodiments. Systems and methods to reduce habituation and/or tolerance to stimulation are provided in several embodiments by, for example, introducing variability in stimulation parameter(s), as described herein. Habituation and/or tolerance to neurostimulation that occur in the treatment of movement, inflammatory, neurological and psychiatric disorders are treated in several embodiments.

The satisfaction data 1414 can include but is not limited to subjective data provided by the user. The subjective data can relate to pre or post treatment and/or patient activities of daily living (ADL). In certain embodiments, the patient inputs a value that reflects a level of satisfaction. The level of satisfaction can be selected from a predetermined range. In certain embodiments, the range is from 1 to 4. Of course, the range can be any range and is not limited to 1 to 4. For example, the user can provide input to the user interface 212 in the form of a patient session impression of improvement (PSII) score and/or a patient satisfaction scope.

In certain embodiments at block 1410, the learning algorithm 222 determines a level of patient therapeutic benefit based on the passive kinematic measurements 1412 without requiring the patient to input a subjective satisfaction level. In certain embodiments, the learning algorithm 222 receives the kinematic measurements 1412 measured during the therapy session along with satisfaction data 1414 input by the user. In this way in certain embodiments, the learning algorithm 222 can determine a level of patient therapeutic benefit based on both the passive kinematic data and the patient provided subjective satisfaction level.

At block 1410, the learning algorithm 222 can select from processes 1402-1408 for varying parameter(s) employed during therapy session based on adaptive learning to improve tremor therapeutic treatment. In certain embodiments, the learning algorithm 222 can select from a plurality of stimulation parameters (e.g., burst frequency and pulse frequency) to vary one parameter across one or more nerves (e.g., median and/or radial nerve) and/or select multiple stimulation parameters to vary across one or more nerves.

In certain embodiments, the plurality of stimulation parameters accessed by the learning algorithm 222 can be a subset of all of the stimulation parameters and or patterns of applying stimulation parameters. For example, in certain embodiments, the learning algorithm 222 selects from the processes 1402-1408 for which a positive outcome is predicted by the learning algorithm 222. In certain embodiments, the learning algorithm 222 modifies the one or more parameters of the selected process based on the individual patient to further personalize the stimulation parameters. In certain embodiments, the learning algorithm 222 can automatically determine a correlation between the satisfaction data 1414 and/or the kinematic measurements 1412 and neurostimulation therapy outcomes to select from the processes 1402-1408.

In several embodiments, neuromodulation, such as neurostimulation, is used to replace pharmaceutical agents, and thus reduce undesired drug side effects. In other embodiments, neuromodulation, such as neurostimulation, is used together with (e.g., synergistically with) pharmaceutical agents to, for example, reduce the dose or duration of drug therapy, thereby reducing undesired side effects. Undesired drug side effects include for example, addiction, tolerance, dependence, GI issues, nausea, confusion, dyskinesia, altered appetite, etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11,12,13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve "includes" instructing the stimulation of an afferent peripheral nerve."

What is claimed:

1. A method of generating jitter variation of nerve stimulation in a non-implantable wrist-worn device to enhance therapeutic response for a user, the method comprising:

measuring a pathological tremor frequency of a tremor of the user;

calculating or setting a treatment frequency that is different from the pathological tremor frequency to avoid exact alignment to the pathological tremor frequency, wherein the treatment frequency comprises a burst frequency and a burst frequency variation, wherein the burst frequency is centered around the pathological tremor frequency of the user, wherein the burst frequency variation varies by less than 6 Hz from the measured pathological tremor frequency of the user; and treating the user's tremor by stimulating at least two nerves, using at least two electrodes, wherein the at least two electrodes are located on the wrist-worn device, wherein the at least two electrodes are non-implantable, wherein the stimulating is performed using the treatment frequency, wherein at least one of (i) the burst frequency is jittered at a rate between 0.01 Hz/s and 0.1 Hz/s or (ii) a pulse frequency of the treatment frequency is jittered at a rate between 1 Hz/s and 10 Hz/s, and wherein the jitter facilitates the treatment of the user's tremor.

2. The method of claim 1, wherein the burst frequency is in a range of 3-12 Hz.

3. The method of claim 1, wherein, if the pathological tremor frequency is low, the burst frequency is not jittered to be lower than the pathological tremor frequency;

wherein, if the pathological tremor frequency is high, the burst frequency is not jittered to be higher than the pathological tremor frequency.

4. The method of claim 1, further comprising stimulating at the pathological tremor frequency of the user.

5. The method of claim 1, wherein the at least two nerves comprises a median nerve.

6. The method of claim 1, wherein the at least two nerves comprises a radial nerve.

7. The method of claim 1, wherein the at least two nerves comprises an ulnar nerve.

8. The method of claim 1, further comprising positioning a first nerve electrode of the at least two electrodes to deliver stimulation to a median nerve.

9. The method of claim 1, further comprising positioning a first nerve electrode of the at least two electrodes to deliver stimulation to a radial nerve.

10. The method of claim 1, further comprising positioning a first nerve electrode of the at least two electrodes to deliver stimulation to an ulnar nerve.

11. The method of claim 1, further comprising:

measuring motion of an extremity of the user using one or more biomechanical sensors to generate motion data; and calculating or setting the treatment frequency based on the motion data.

12. The method of claim 1, wherein the burst frequency is varied at the rate between 0.01 Hz/s and 0.1 Hz/s.

13. A method of generating jitter variation of nerve stimulation in a non-implantable wrist worn device to enhance therapeutic response for a user, the method comprising:

measuring a pathological frequency of a user;

calculating or setting a treatment frequency that is different from the pathological frequency to avoid exact alignment to the pathological frequency; and treating the user by stimulating at least two nerves, using at least two electrodes;

wherein the at least two electrodes are located on the wrist-worn device, wherein the at least two electrodes are non-implantable, wherein the stimulating is performed using the treatment frequency, wherein the treatment frequency is jittered at a rate less than 100 Hz/s, wherein the treatment frequency comprises one or more of: (i) a burst frequency and a burst frequency variation and (ii) a pulse frequency and a pulse frequency variation, wherein if the treatment frequency comprises the burst frequency, the burst frequency is centered around the pathological frequency of the user and the burst frequency variation varies by less than 6 Hz from the measured pathological tremor frequency of the user, wherein if the treatment frequency comprises the pulse frequency, the pulse frequency is varied in a range of 50-150 Hz, wherein at least one of (i) the burst frequency is jittered at a rate between 0.01 Hz/s and 0.1 Hz/s or (ii) the pulse frequency is jittered at a rate between 1 Hz/s and 10 Hz/s, and wherein the jitter is therapeutically effective to reduce habituation to a therapy for the user.

14. The method of claim 13, wherein the treatment frequency is a burst frequency in a range of 3-12 Hz.

15. The method of claim 13, wherein the treatment frequency is the burst frequency, and wherein the burst frequency varies by less than 3 Hz from the measured tremor frequency of the user.

16. The method of claim 13, further comprising stimulation at the pathological frequency of the user.

17. The method of claim 13, wherein the at least two nerves comprises a median nerve.

18. The method of claim 13, wherein the at least two nerves comprises a radial nerve.

19. The method of claim 13, wherein the at least two nerves comprises an ulnar nerve.

20. The method of claim 13, for the treatment of tremor, depression, inflammation, headache, gastrointestinal disorder, or cardiac disease.

21. The method of claim 13, wherein the burst frequency is varied at the rate between 0.01 Hz/s and 0.1 Hz/s and wherein the pulse frequency is varied at the rate between 1-10 Hz/s.

* * * * *